(12) United States Patent
Gutman et al.

(10) Patent No.: US 7,166,730 B2
(45) Date of Patent: *Jan. 23, 2007

(54) PROCESS FOR THE PREPARATION OF PROSTAGLANDIN DERIVATIVES

(75) Inventors: Arie Gutman, Haifa (IL); Gennady Nisnevich, Haifa (IL); Marina Etinger, Nesher (IL); Igor Zaltzman, Haifa (IL); Lev Yudovich, Haifa (IL); Boris Pertsikov, Nesher (IL); Boris Tishin, Haifa (IL)

(73) Assignee: Fine Tech Laboratories, Ltd, Nesher (IL)

(*) Notice: Subject to any disclaimer, the term of this patent is extended or adjusted under 35 U.S.C. 154(b) by 0 days.

This patent is subject to a terminal disclaimer.

(21) Appl. No.: 11/125,164

(22) Filed: May 10, 2005

(65) Prior Publication Data

US 2005/0209337 A1    Sep. 22, 2005

Related U.S. Application Data

(63) Continuation-in-part of application No. 10/181,523, filed as application No. PCT/IL01/00076 on Jan. 26, 2001, now Pat. No. 6,927,300, application No. 11/125,164, which is a continuation-in-part of application No. 10/478,849, filed as application No. PCT/IL02/00422 on May 30, 2002.

(30) Foreign Application Priority Data

Jan. 27, 2000  (IL)  .................................. 134241
May 31, 2001  (IL)  .................................. 143477

(51) Int. Cl.
*C07C 51/363* (2006.01)

(52) U.S. Cl. ................. 554/159; 554/142; 554/221; 554/222

(58) Field of Classification Search ........... 554/222, 554/142, 159, 221
See application file for complete search history.

(56) References Cited

U.S. PATENT DOCUMENTS

| | | | | |
|---|---|---|---|---|
| 5,151,444 | A | * | 9/1992 | Ueno et al. ............. 514/530 |
| 5,688,819 | A | * | 11/1997 | Woodward et al. ........ 514/357 |
| 5,849,792 | A | * | 12/1998 | Schneider ............... 514/530 |
| 6,927,300 | B1 | * | 8/2005 | Gutman et al. .......... 554/222 |

OTHER PUBLICATIONS

Nanno, Chem. Abstr, 134:110001, 2000.*
Takagi et al, Journal of Experimental Research, vol. 78, pp. 767-776, 2004.*
Chem. Abstrs. of cited patent using compounds and registry numbers.*
Woodward et al. Chem. Abstr, 127:243271, 1997, shows compounds and registry numbers.*
Ueno et al., Chem. Abstr., 110:212479, 1989, shows compound and registry niumbers.*
Schneider et al., Chem. Abstr., 132:69332,2000, shows compounds and regisrty numbers.*

* cited by examiner

*Primary Examiner*—Deborah D. Carr
(74) *Attorney, Agent, or Firm*—Pearl Cohen Zedek Latzer, LLP; Mark S. Cohen

(57) ABSTRACT

The invention provides a novel process for the preparation of prostaglandins and analogues thereof, and new crystalline intermediates in the process.

22 Claims, 25 Drawing Sheets

PROCESS FOR THE PREPARATION OF PROSTAGLANDIN DERIVATIVES

CROSS REFERENCE TO RELATED APPLICATIONS

This application is a Continuation in Part application of U.S. patent application Ser. No. 10/181,523, filed Oct. 25, 2002 now U.S. Pat. No. 6,927,300; which is a National Phase Application of PCT International Application No. PCT/IL01/00076, International Filing Date Jan. 26, 2001, claiming priority of IL 134241 Patent Application, filed Jan. 27, 2000. And of U.S. patent application Ser. No. 10/478,849, filed Apr. 28, 2004, which is a National Phase Application of PCT International Application No. PCT/IL02/00422 International Filing Date May 30, 2002, claiming priority of IL 143477 Patent Applications, filed May 31, 2001 which is hereby incorporated by reference.

FIELD OF THE INVENTION

This invention relates to a novel process for the preparation of prostaglandins and analogues thereof.

BACKGROUND OF THE INVENTION

Elevated intraocular pressure (IOP) is the major risk factor associated with the etiology of glaucoma, a progressive optic neuropathy that can ultimately cause blindness. Prostaglandin (PG) analogs represent the most potent therapeutic agents in the clinical management of ocular hypertension and glaucoma today. The marketed PG analogs used to reduce IOP include Travatan™ ((9S,11R,15R)-9,11,15-trihydroxy-16-[3-(trifluoromethyl)phenoxy]-17,18,19,20-tetranor-5Z,13E-prostadienoic acid, isopropyl ester)

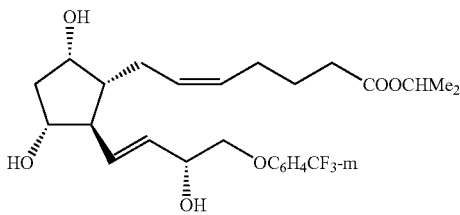

travoprost;

Xalatan™ ((9S,11R,15R)-9,11,15-trihydroxy-17-phenyl-18,19,20-trinor-5Z-prostenoic acid, isopropyl ester)

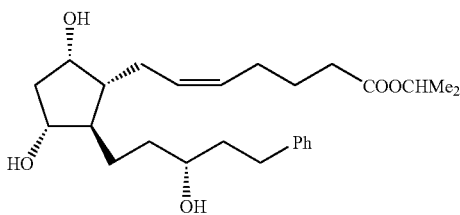

latanoprost;

Rescula™ ((9S,11R)-9,11-dihydroxy-15-keto-20-ethyl-5Z-prostenoic acid, isopropyl ester)

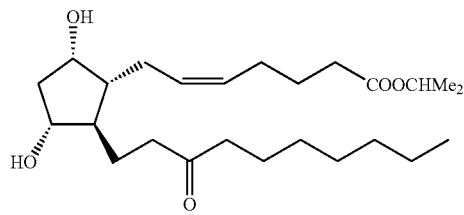

unoprostone isopropyl ester;

Lumigan™ ((9S, 11R, 15S)-9,11,15-trihydroxy-17-phenyl-18,19,20-trinor-5Z,13E-prostadienoic acid, ethylamide)

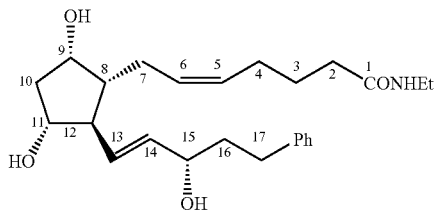

bimatoprost (J. Ocular Pharmacol. Therap., 2003, v. 19, 501). The conventional numbering of prostaglandins and like structures is indicated in connection with the formula of bimatoprost. It should be noted that bimatoprost may be easily prepared by reaction of methyl (9S,11R,15R)-9,11,15-trihydroxy-17-phenyl-18,19,20-trinor-5Z,13E-prostadienoate

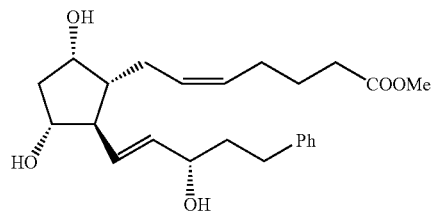

with ethylamine.

Newly synthesized PGF$_{2\alpha}$ analogue (9S,11R)-9,11-dihydroxy-16-phenoxy-15,15-difluoro-17,18,19,20-tetranor-5Z,13E-prostadienoic acid, isopropyl ester

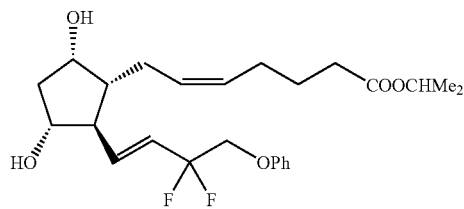

tafluprost is under development as an ocular hypotensive drug in the USA, Europe, and Japan (Exp. Eye Res., 2004, v. 78, 767).

The known methods for the synthesis of alkyl 5Z-prostenoates of formula [1]

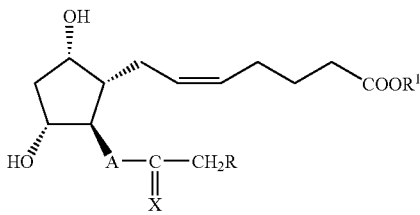

wherein
R is 3-$CF_3C_6H_4O$—, 3-$ClC_6H_4O$—, PhO—, Bn—, Bu—, Me($CH_2$)$_5$—; A is —$CH_2CH_2$— or —CH=CH—; X is $X^1$, O or (α-OH, H); $X^1$ is (α-$OR^3$, H); —$OCH_2CH_2O$— or (F, F); $R^1$ is $C_1$–$C_{10}$ alkyl group; $R^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down;

(see U.S. Pat. Nos. 3,931,279; 5,223,537; 5,698,733; and 5,688,819; WO95/26729, Prostaglandins, v. 9, 5 1975, J. Med. Chem., 1993, 36, 243) are shown in Scheme 1 below and include the stages of phosphonate Horner-Emmons-Wadsworth reaction with Corey aldehyde in anhydrous condition using BuLi, NaH or $Et_3$N/LiCl as base to yield enone, reducing lactone to lactol with diisobutylaluminum hydride at temperature –70 to –80° C. and alkylation of acid [3] in the presence of DBU or $K_2CO_3$ to the desired compound [1].

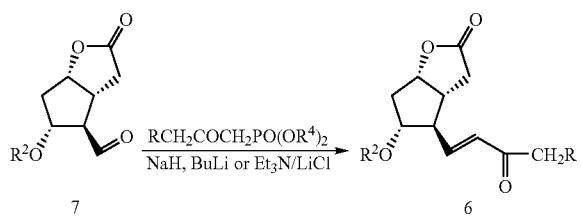

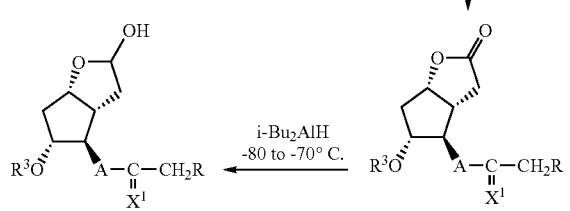

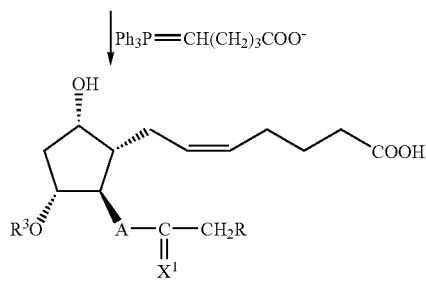

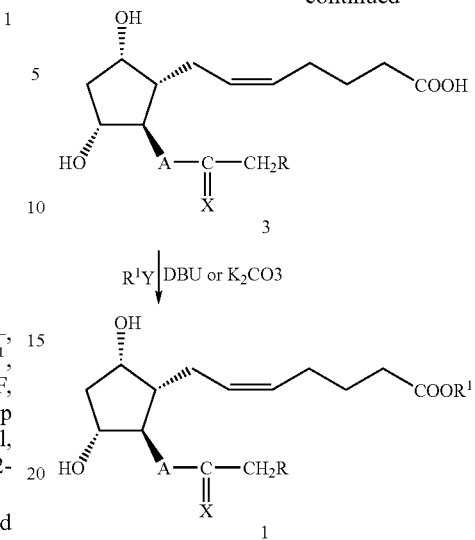

wherein
R is 3-$CF_3C_6H_4O$—, 3-$ClC_6H_4O$—, PhO—, Bn—, Bu—, Me($CH_2$)$_5$—; A is —$CH_2CH_2$— or —CH=CH—; X is $X^1$, O or (α-OH, H); $X^1$ is (α-$OR^3$, H); —$OCH_2CH_2O$— or (F, F); $R^1$ is $C_1$–$C_{10}$ alkyl group; $R^2$ is arylcarbonyl group; $R^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; $R^4$ is $C_1$-$C_4$ alkyl, Ph or Bn; Y is a leaving group; α is down;

The described Horner-Emmons-Wadsworth and alkylation reactions give low yield of desired products. On the other hand it is difficult to scale-up the highly exothermic reduction with diisobutylaluminum hydride at such low temperature conditions.

SUMMARY OF THE INVENTION

It is an object of this invention to provide a novel process for the preparation of alkyl 5Z-prostenoates in good yield, in large amounts and with desired purity.

It is a further object of this invention to provide novel intermediates for the above process.

The above objects are achieved by the present invention, which provides a process for the preparation of alkyl 5Z-prostenoates of formula [1]

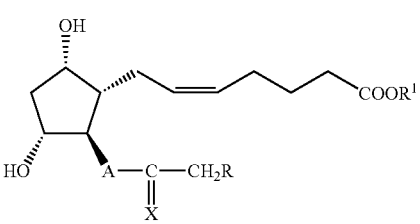

wherein R is 3-$CF_3C_6H_4O$—, 3-$ClC_6H_4O$—, PhO—, Bn—, Bu—, Me($CH_2$)$_5$—; A is —$CH_2CH_2$— or —CH=CH—; X is $X^1$, O or (α-OH, H); $X^1$ is (α-$OR^3$, H); —$OCH_2CH_2O$— or (F, F); $R^1$ is $C_1$–$C_{10}$ alkyl group; $R^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down;

such process comprising:
(a) contacting Corey aldehyde of formula [7]

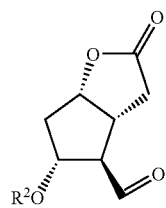

wherein $R^2$ is arylcarbonyl group, with a β-ketophosphonate of formula [8]

wherein $R^4$ is $C_1$–$C_4$ alkyl, Ph or Bn and where R is as defined above, in the presence of an aqueous alkali;
(b) converting the compound of formula [6]

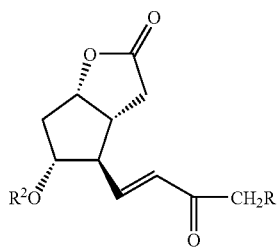

prepared in the step (a), to compound of formula [5]

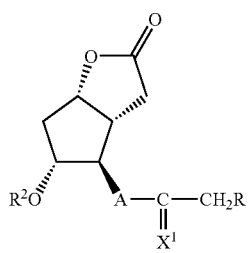

wherein $X^1$, A, R and $R^2$ are as defined above;
(c) reducing the compound [5] with diisobutylaluminum hydride at a temperature range from −30 to +20° C. to give the compound [4]

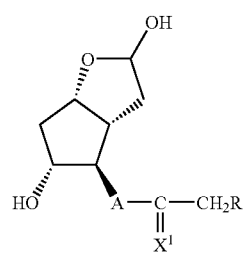

wherein A, R and $X^1$ are as defined above;

(d) reacting compound [4] with a metal salt of 5-(triphenylphosphoranylidene)pentanoic acid, to obtain the acid of formula [3]

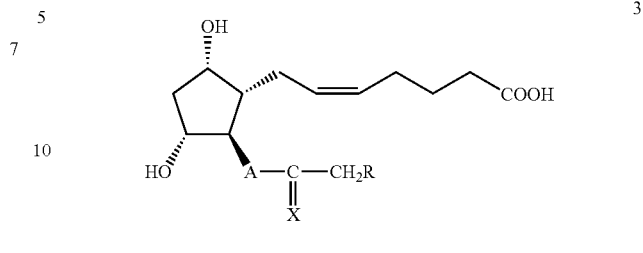

wherein A, R and X are as defined above;
(e) converting compound [3] to cesium salt of formula [2]

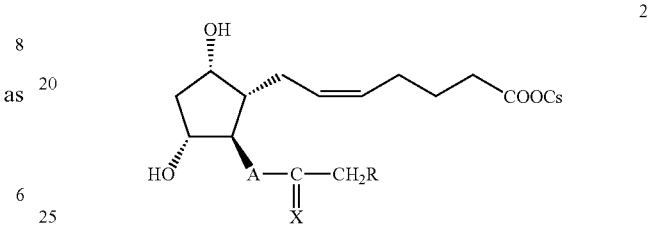

wherein A, R and X are as defined above; and
(f) esterifying the cesium salt [2] with compound $$R^1Y$$

wherein Y is a leaving group and $R^1$ is as defined above; to give the desired compound [1].

In another embodiment, the invention provides a process for the preparation of compound of formula

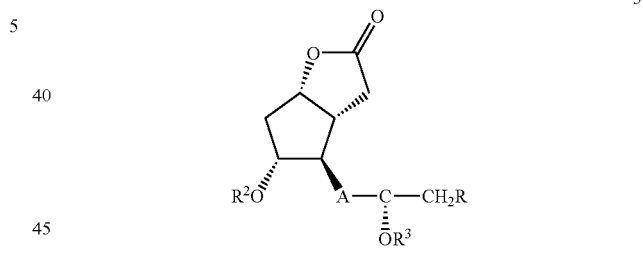

[X=(α-$OR^3$, H)]

wherein A, R, $R^2$ and $R^3$ are as defined above;
which process comprising the steps of
stereoselective reduction of the carbonyl group of the compound [6]

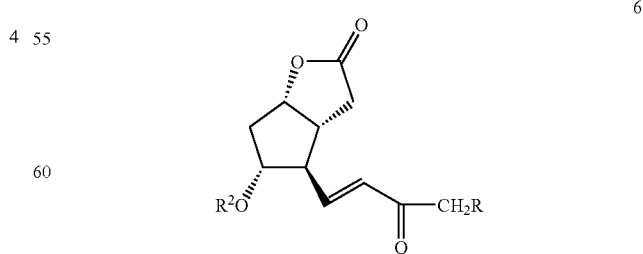

wherein R and $R^2$ are as defined above,
to yield a mixture of compounds of formulae [5-1] and [9-1]

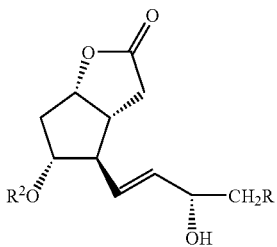

5-1

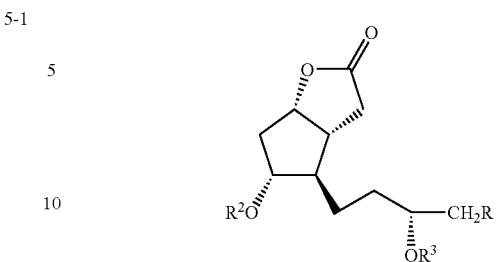

5

[A=—CH$_2$CH$_2$—; X$^1$=(α-OR$^3$, H)]

wherein R, R$^2$ and R$^3$ are as defined above.

Some of the new compounds [4] and [5] wherein X is α-OSiMe$_2$Bu$^t$, H; R is Bn, 3-CF$_3$C$_6$H$_4$O— and R$^2$ is PPB, which are obtained as intermediates in the process of the present invention, may be purified by crystallization from organic solvents. These new compounds represent a further aspect of the invention.

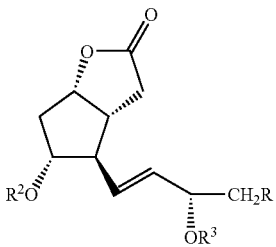

wherein R and R$^2$ are as defined above, and where [5-1] is the predominant isomer, which are subsequently converted into a mixture of compounds of formulae [5] [A=—CH=CH—; X=(α-OR$^3$, H)]

9-1

9-2

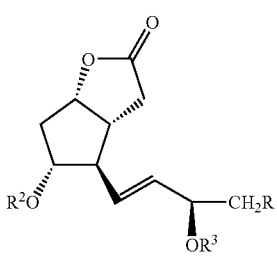

[A=—CH=CH—; X=(α-OR$^3$, H)]
and [9-2]

followed by isolation of the compound [5] [A=—CH=CH—; X=(α-OR$^3$, H)] from the mixture and, if desired, catalytic hydrogenation of the compound [5] [A=—CH=CH—; X$^1$=(α-OR$^3$, H)] to give compound of formula [5] [A=—CH$_2$CH$_2$—; X$^1$=(α-OR$^3$, H)]

DETAILED DESCRIPTION OF THE INVENTION

Figure 1:
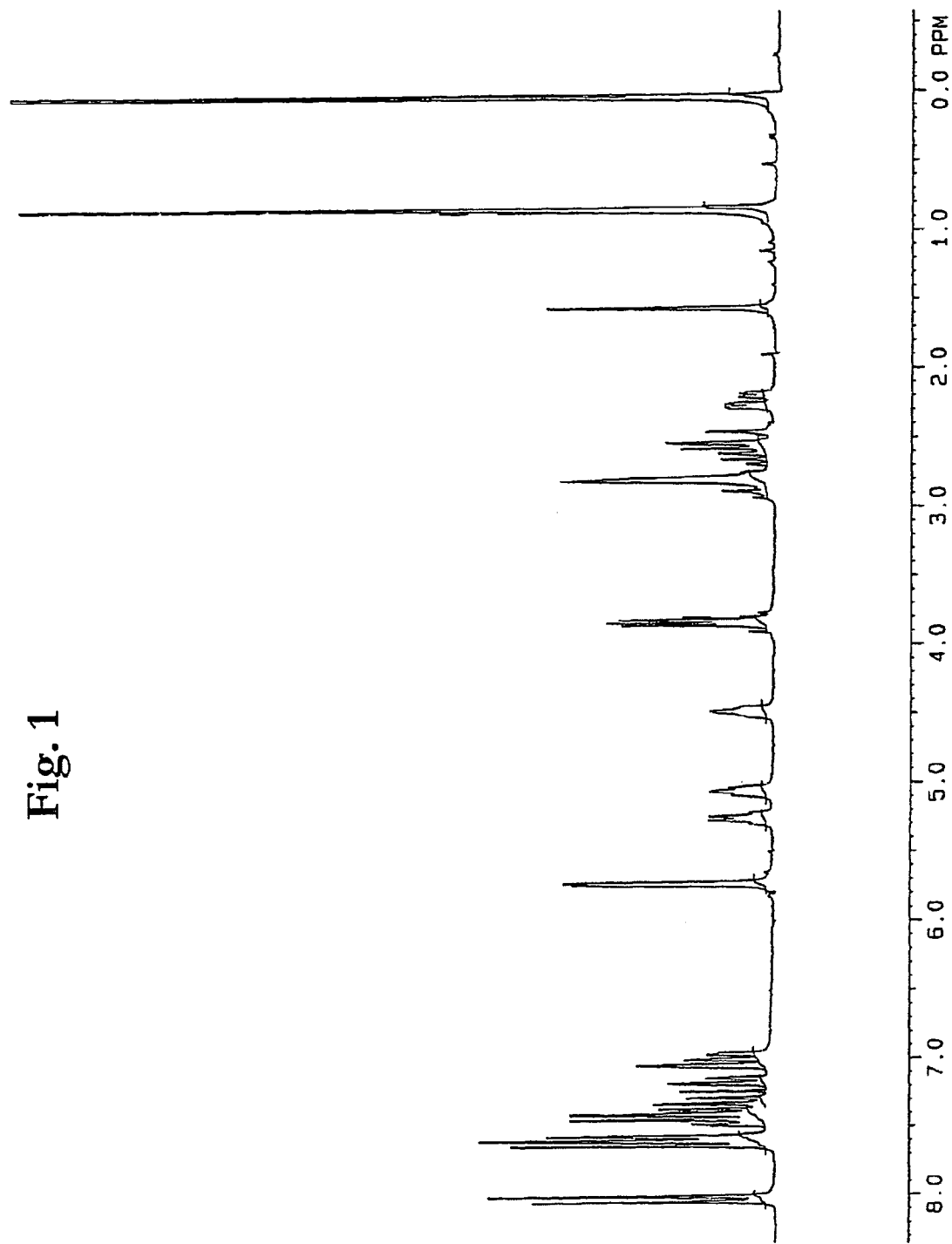
FIG. 1 shows the $^1$H nuclear magnetic resonance (NMR) spectrum of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one in CDCl$_3$.
Figure 2:
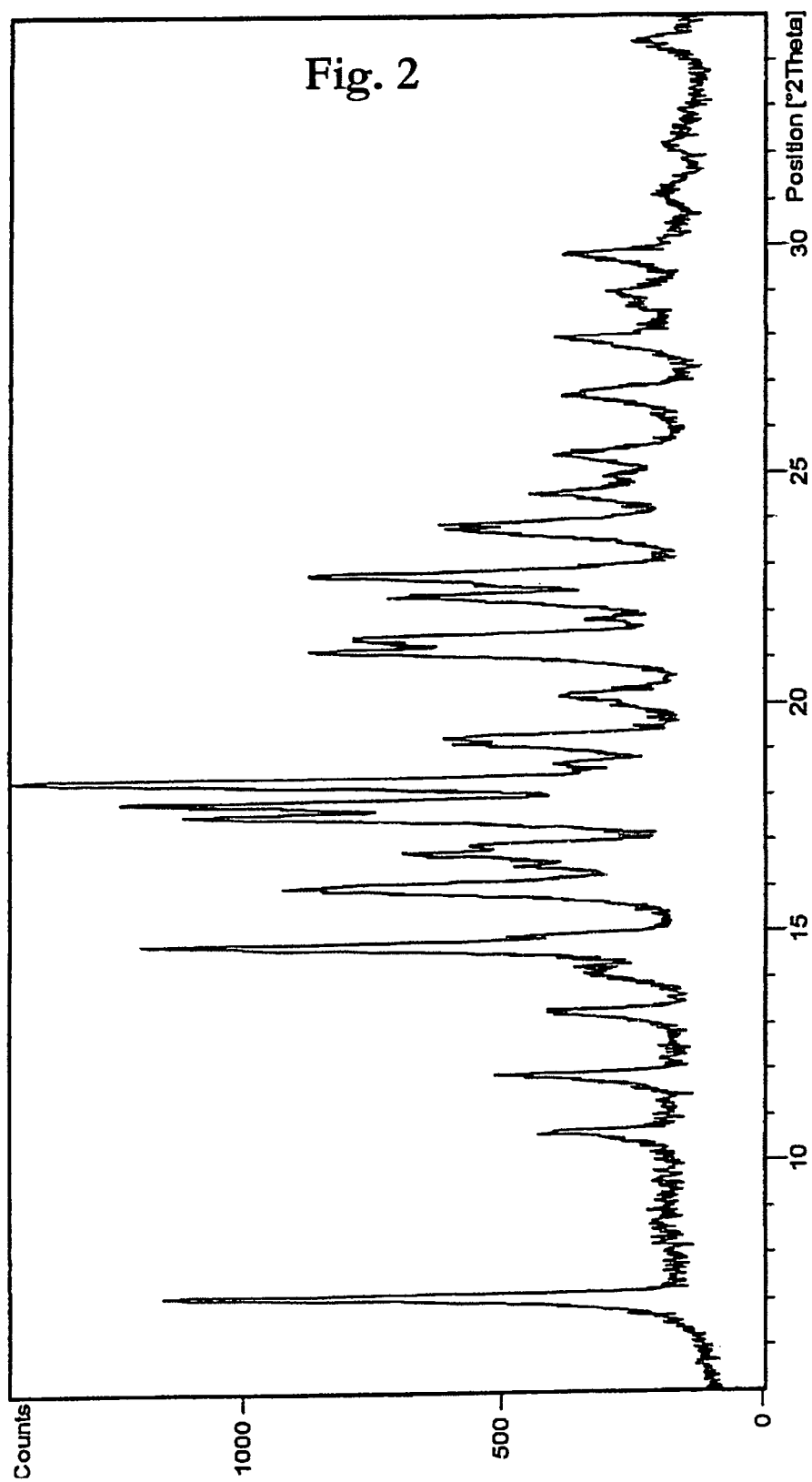
FIG. 2 shows a characteristic x-ray powder diffraction pattern of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one, according to embodiments of the present invention. Vertical axis: intensity (counts per second); Horizontal axis: 2θ (degrees).
Figure 3:
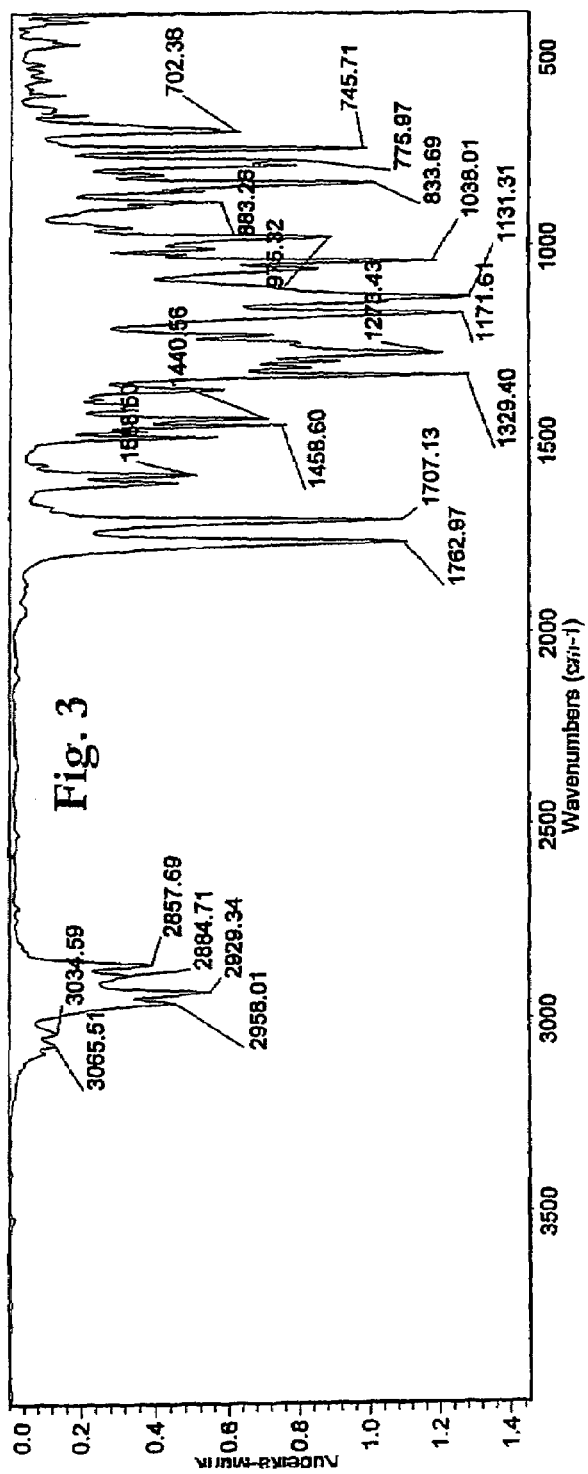
FIG. 3 shows the infrared spectrum (diffuse reflectance, DRIFTS) of (3aR,4R,5R,6aS)-4-[3R-(t-butyldimethylsiloxy)-4-[3-trifluoromethyl)phenoxy]-1E-butenyl]-5-(4-phenylbenzoyloxy)-hexahydro-2H-cyclopenta[b]furan-2-one in potassium bromide, according to embodiments of the invention.
Figure 4:
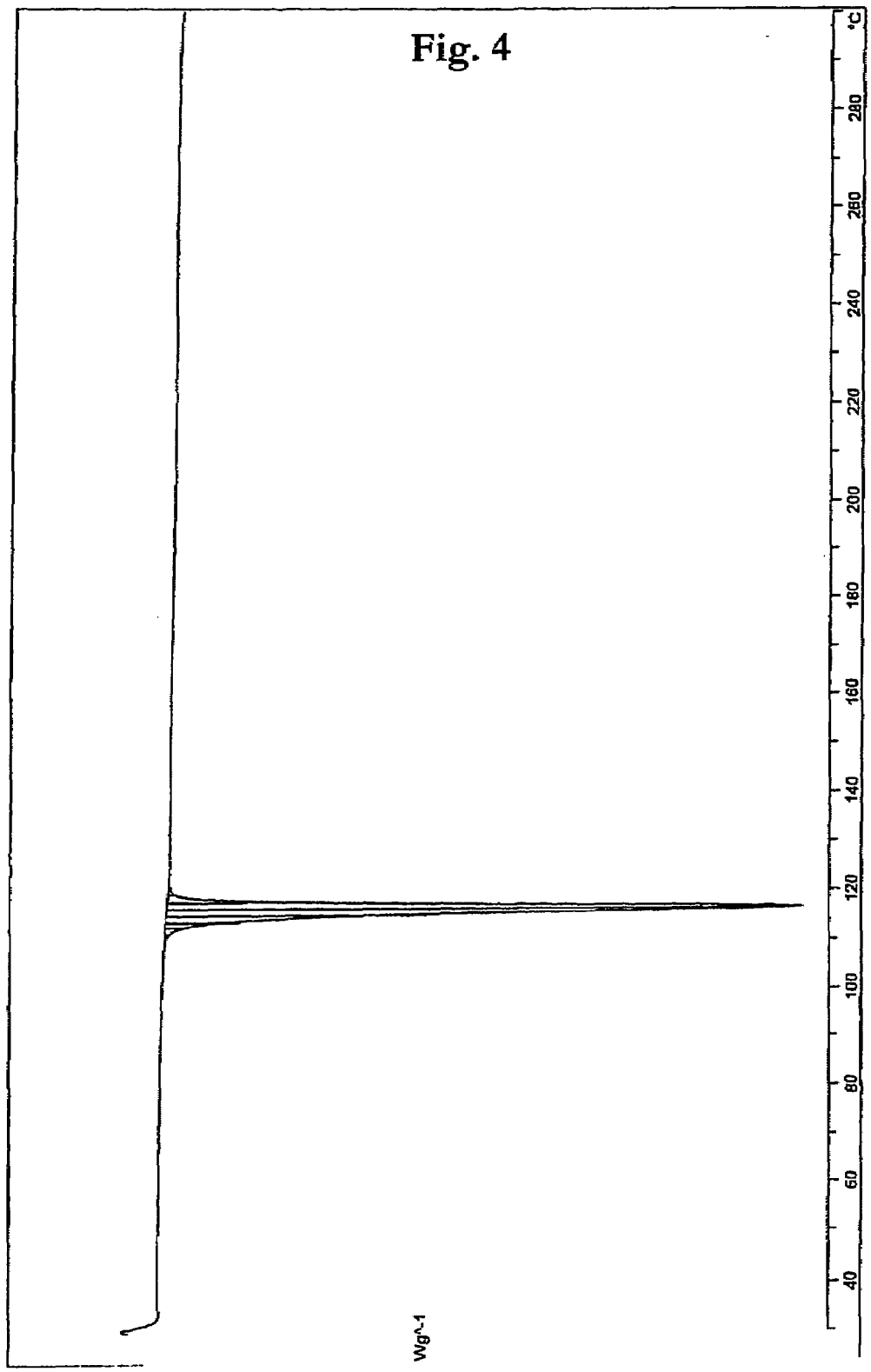
FIG. 4 shows the differential scanning calorimetry (DSC) curve of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one, according to embodiments of the invention.
Figure 5:
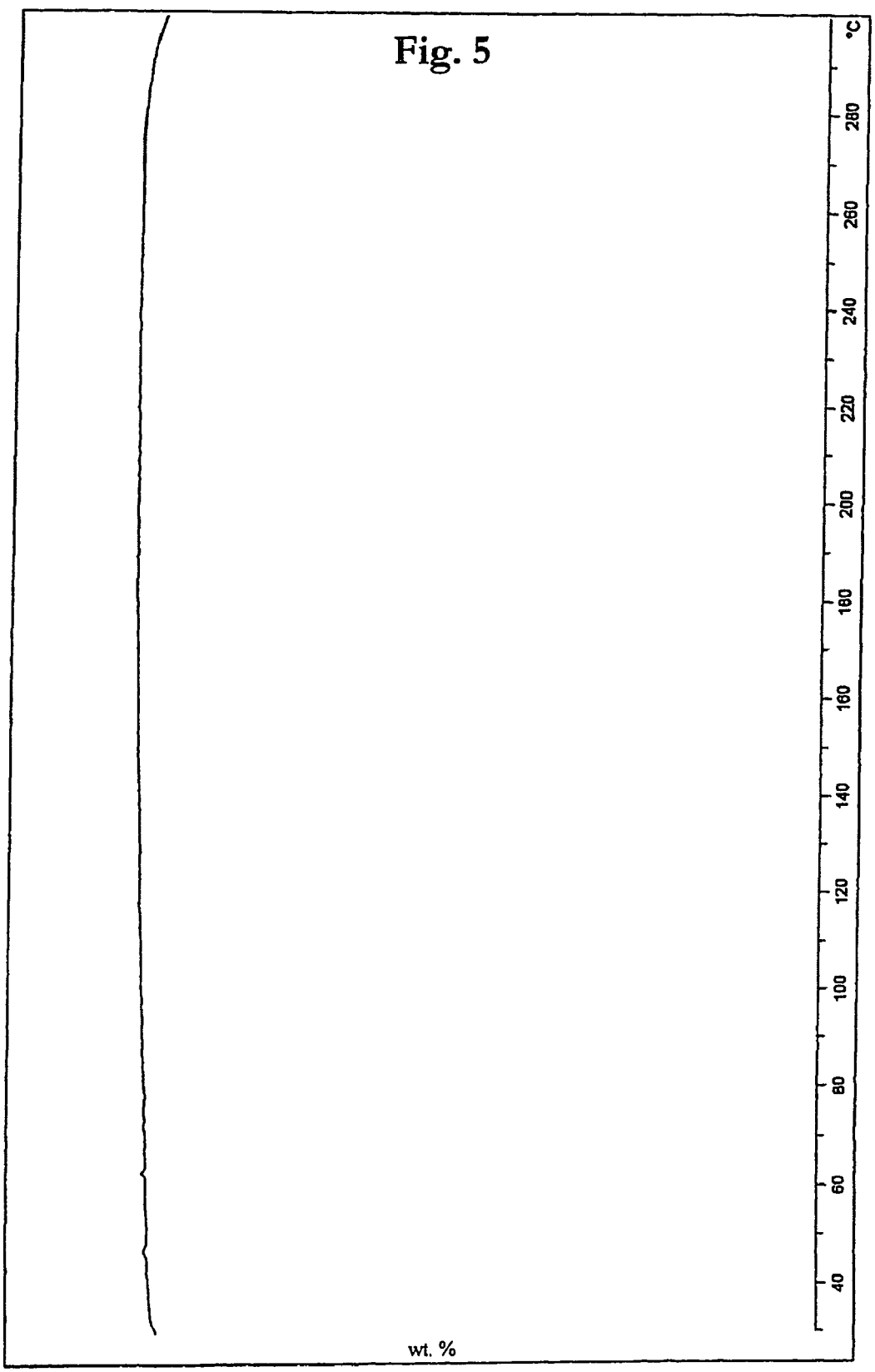
FIG. 5 shows the thermograviometric (TGA) curve of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one, according to embodiments of the invention.

The benefits of the process of the present invention are, inter alia, the following: (a) unexpected highly effective and pure Horner-Emmons-Wadsworth reaction of Corey aldehyde [7] with a β-ketophosphonate [8] in the presence of an aqueous alkali; (b) the selective reduction of the lactone-group of the compound [5] with diisobutylaluminum hydride may proceed at industrially acceptable temperature range from −50 to +20° C., preferably from −30 to 0° C. and (c) highly effective reaction of cesium 5Z-prostenoates with alkylation agents.

Alkyl 5Z-prostenoates of formula [1]

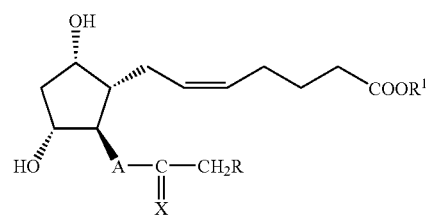

wherein R is 3-CF$_3$C$_6$H$_4$O—, 3-ClC$_6$H$_4$O—, PhO—, Bn—, Bu—, Me(CH$_2$)$_5$—; A is —CHCH$_2$— or —CH=CH—; X is X$^1$, O or (α-OH, H); X$^1$ is (α-OR$^3$, H); —OCH$_2$CH$_2$O— or (F, F); R$^1$ is C$_1$–C$_{10}$ alkyl group; R$^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down;

may be prepared by reacting of 5Z-prostenoic acid [3]

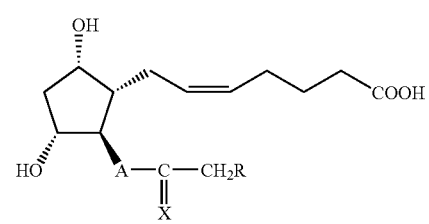

with alkylation agent

R$^1$Y wherein Y is a leaving group and R$^1$ is as defined above, in the presence of base.

Preferably, the alkylation agent is alkyl iodide, bromide, methanesulfonate, p-toluenesulfonate, 2,4-dinitrophenylsulfonate or triflate. Preferably the alkyl group is isopropyl or methyl group.

Optionaly, the base is 1,8-diazabicyclo[5.4.0]undec-7-ene (DBU). Preferably, the base is $K_2CO_3$. Most preferably, the base is cesium carbonate, hydrogencarbonate, hydroxide or fluoride or mixture thereof. If cesium alkali is used as base in the alkylation reaction cesium salt of 5Z-prostenoic acid

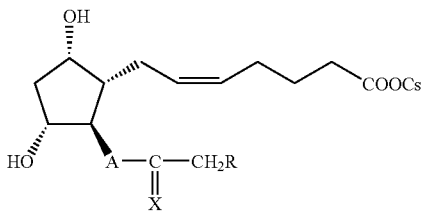

2 is obtained as intermediate in the reaction.

Preferably, the alkylation reaction of 5Z-prostenoic acid [3] is provided in the presence of solvent. Preferably, the solvent is aprotic organic solvent. More preferably, the solvent is polar organic solvent. For example, the polar organic solvent is N,N-dimethylformamide (DMF), N,N-dimethylacetamide, 1-methyl-2-pyrrolidinone (NMP), dimethyl sulfoxide (DMSO), sulfolane or HMPA. Preferably the solvent is DMF.

The $PGF_{2\alpha}$ derivatives of formula [1] prepared by the reaction may be purified by flash chromatography. Preferably the purification is provided by preparative LC on silica gel or Phenomenex™ Luna CN silica gel.

According to embodiment of the invention, the 5Z-prostenoic acid [3] is prepared by Wittig reacting of lactol

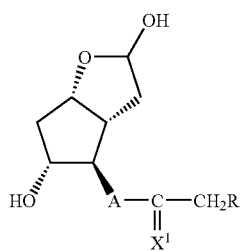

4 with a metal salt of 5-(triphenylphosphoranylidene)pentanoic acid. Preferably, the reaction is provided in the presence of aprotic organic solvent. More preferably, the solvent is ether-type solvent. Most preferably the solvent is THF.

The lactol [4] may be prepared by reducing compound of formula

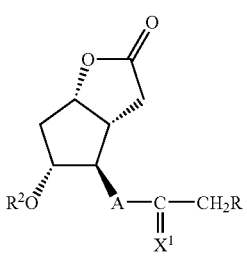

5 wherein $X^1$ is ($\alpha$-$OR^4$, H), —$OCH_2CH_2O$— or (F, F); A, R, $R^2$ and $R^4$ are as defined above; with diisobutylaluminum hydride at temperature range from −80 to −50° C. Preferably, the reaction temperature range is −50 to +20° C., more preferably −30 to 0° C. To increase the yield of lactol [4] it is desirable to add diisobutylaluminum hydride to compound [5] at −50 to +20° C. (preferably at −30 to 0° C.) to attain about 95–99% conversion of lactone group. Preferably, the reaction is provided in the presence of aprotic organic solvent. More preferably, the solvent is toluene, $CH_2Cl_2$, THF, ether or mixture thereof.

In another embodiment of the invention, the invention provides (3aR,4R,5R,6aS)-4-[3S-(t-butyldimethylsiloxy)-5-phenyl-1E-pentenyl]-5-hydroxy-hexahydro-2H-cyclopenta[b]furan-2-ol of the formula

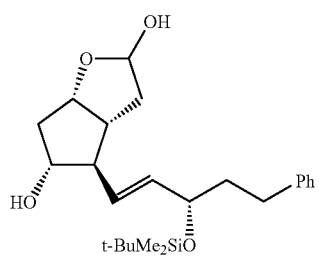

In another embodiment of the invention, the invention further provides crystalline (3aR,4R,5R,6aS)-4-[3S-(t-butyldimethylsiloxy)-5-phenyl-1E-pentenyl]-5-hydroxy-hexahydro-2H-cyclopenta[b]furan-2-ol.

In another embodiment of the invention, the invention provides (3aR,4R,5R,6aS)-4-[3R-(t-butyldimethylsiloxy)-5-phenylpentyl]-5-hydroxy-hexahydro-2H-cyclopenta[b]furan-2-ol of the formula

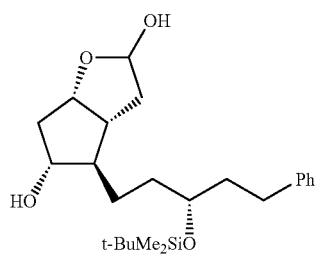

In another embodiment of the invention, the invention further provides crystalline (3aR,4R,5R,6aS)-4-[3R-(t-butyldimethylsiloxy)-5-phenylpentyl]-5-hydroxy-hexahydro-2H-cyclopenta[b]furan-2-ol.

In another embodiment of the invention, the invention further provides crystalline (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol of the formula

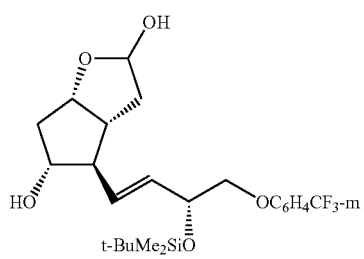

In another embodiment of the invention, the compound 5

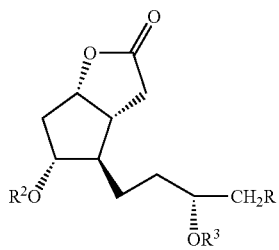

[A=—CH$_2$CH$_2$—; X$^1$=(α-OR$^3$, H)]

wherein R, R$^2$ and R$^3$ are as defined above; is prepared by catalytic hydrogenation of compound 5

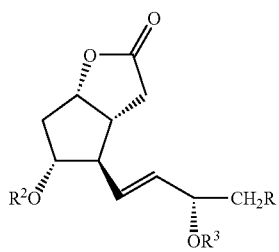

[A=—CH=CH—; X$^1$=(α-OR$^3$, H)]

Preferably the catalyst for hydrogenation of compound 5 [A —CH=CH—; X$^1$=(α-O R$^3$, H)] to compound 5 [A=—CH$_2$CH$_2$—; X$^1$=(α-OR$^3$, H)] contains palladium, platinum or nickel. More preferably the catalyst is palladium-on-carbon, platinum oxide or platinum-on-carbon. Preferably the hydrogenation is carried out in the presence of solvents and bases or salts. Preferably the bases are selected from the group consisting of tertiary and secondary amines. Preferably the salts are selected from the group consisting of metal nitrites, metal alkanoates and metal benzoates.

In another embodiment of the invention, the invention provides (3aR,4R,5R,6aS)-4-[3R-(t-butyldimethylsiloxy)-5-phenylpentyl]-5-hydroxy-hexahydro-2H-cyclopenta[b]furan-2-one of the formula

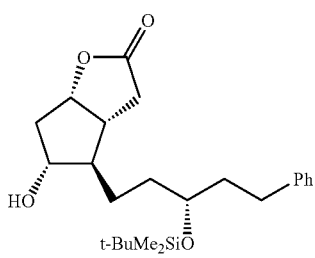

In one embodiment of the invention, the compound of formula 5

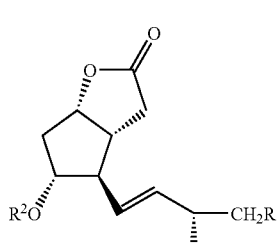

(A=—CH=CH—; X=α-OR$_3$, H)]

is prepared by process comprising:
stereoselective reduction of the carbonyl group of the compound [6]

6

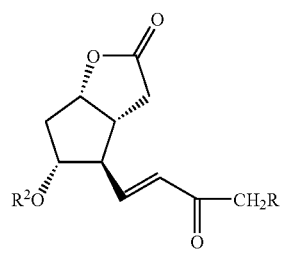

wherein R and R$^2$ are as defined above,
to yield a mixture of compounds of formulae [5-1] and [9-1]

5-1

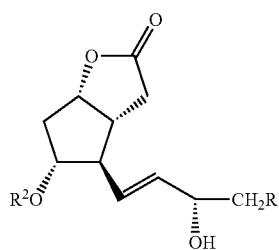

9-1

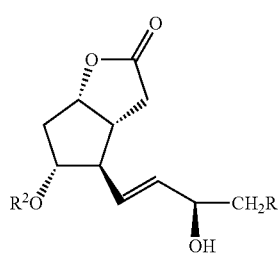

wherein R and R$^2$ are as defined above, and where [5-1] is the predominant isomer, which are subsequently converted into a mixture of compounds of formulae 5 [(—A=—CH=CH—; X$^1$=(α-OR$^3_3$, H)] and 9-2

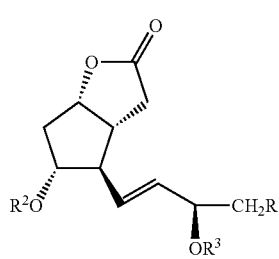

followed by isolation of the compound [5] [A=—CH=CH—; X$^1$=(α-OR$^3$, H)] from the mixture.

The process for the synthesis of compound [5] [A=—CH=CH—; X$^1$=(α-OR$^3$, H)] from enone [6] may be summarized by the following Scheme 2:

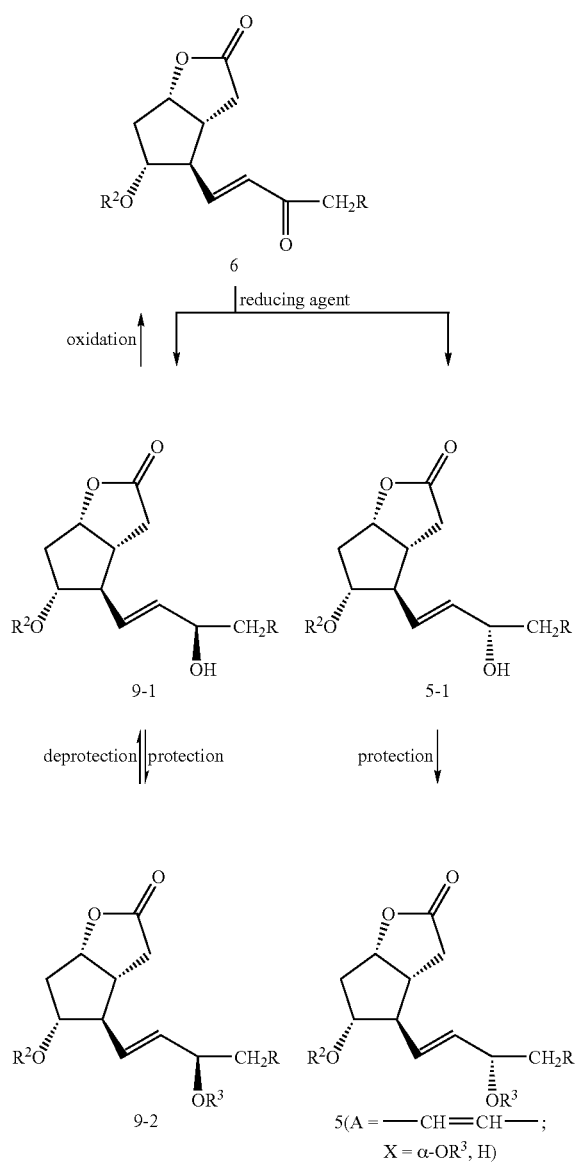

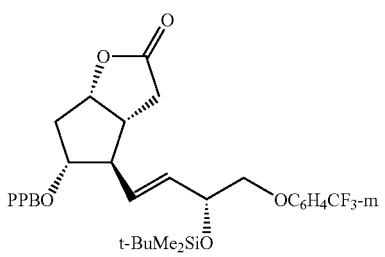

In another embodiment of the invention, the invention further provides crystalline MTBE solvate of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one.

In another embodiment of the invention, the invention further provides crystalline (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one of the formula

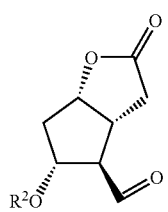

In another embodiment of the invention, it is proposed process for utilization of undesired compound [9-2] to compound [6] which process comprises the steps of converting compound [9-2] into compound [9-1] and oxidizing the hydroxyl group of the compound [9-1].

According to embodiment of the invention, the compound of the formula [6] may be prepared by Horner-Emmons-Wadsworth reaction of Corey aldehyde of formula [7]

7

wherein R is 3-CF$_3$C$_6$H$_4$O—, 3-ClC$_6$H$_4$O—, PhO—, Bn—, Bu—, Me(CH$_2$)$_5$—; R$^2$ is arylcarbonyl group; R$^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group.

Preferably the stereoselective reduction of the compound [6] is carried out with (−)-B-chlorodiisopinocamphenylborane or with borane in the presence of 2-alkyl-CBS-oxazaborolydines. More preferably the reduction is carried out with (−)-B-chlorodiisopinocamphenylborane in organic solvent. Preferably the organic solvent is THF, ether, 1,2-dimethoxyethane, toluene, hexane, CH$_2$Cl$_2$ or mixtures of these solvents.

In another embodiment of the invention, the invention provides (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one of the formula with a β-ketophosphonate of formula [8]

RCH$_2$COCH$_2$PO(OR$^4$)$_2$      8 wherein R$^4$ is C$_1$–C$_4$ alkyl, Ph or Bn and where R is as defined above, in the presence of base. Preferably, the base is BuLi, NaH or Et$_3$N/LiCl. More preferably, the base is alkali. For example the alkali is LiOH, NaOH, KOH, CsOH, Na$_2$CO$_3$, K$_2$CO$_3$ or Cs$_2$CO$_3$. Most preferably, the base is an aqueous alkali. Preferably, the Horner-Emmons-Wadsworth reaction is provided in the presence of organic solvents. For example, the solvent is $CH_2Cl_2$, $CHCl_3$, toluene, TUF, MTBE, ether or mixture thereof.

The process of the present invention for the synthesis of $PGF_{2\alpha}$ derivatives of formula [1] may be summarized by the following Scheme 3

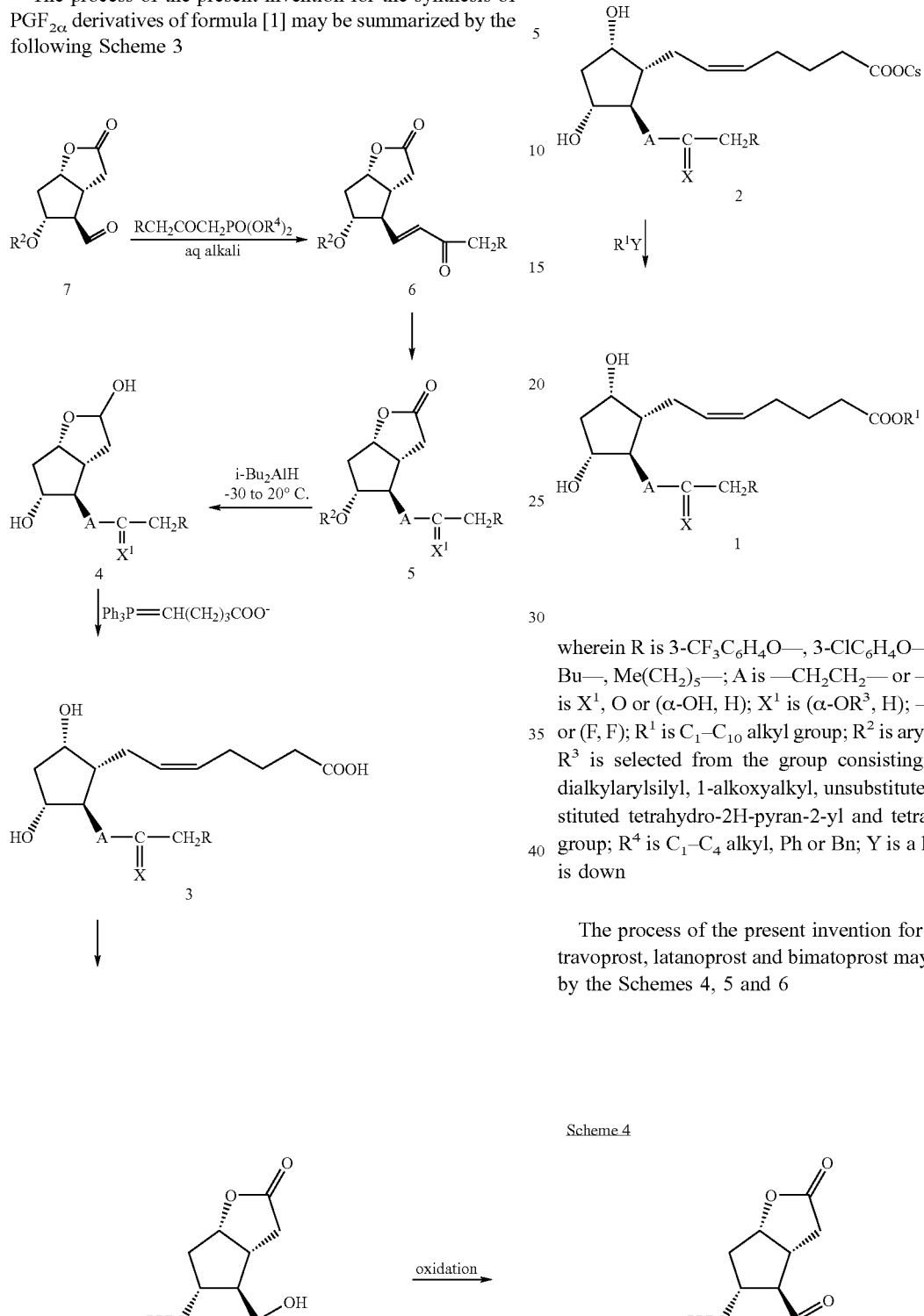

wherein R is 3-$CF_3C_6H_4O$—, 3-$ClC_6H_4O$—, PhO—, Bn—, Bu—, Me$(CH_2)_5$—; A is —$CH_2CH_2$— or —CH=CH—; X is $X^1$, O or ($\alpha$-OH, H); $X^1$ is ($\alpha$-$OR^3$, H); —$OCH_2CH_2O$— or (F, F); $R^1$ is $C_1$–$C_{10}$ alkyl group; $R^2$ is arylcarbonyl group; $R^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; $R^4$ is $C_1$–$C_4$ alkyl, Ph or Bn; Y is a leaving group; $\alpha$ is down The process of the present invention for the synthesis of travoprost, latanoprost and bimatoprost may be summarized by the Schemes 4, 5 and 6

Scheme 4

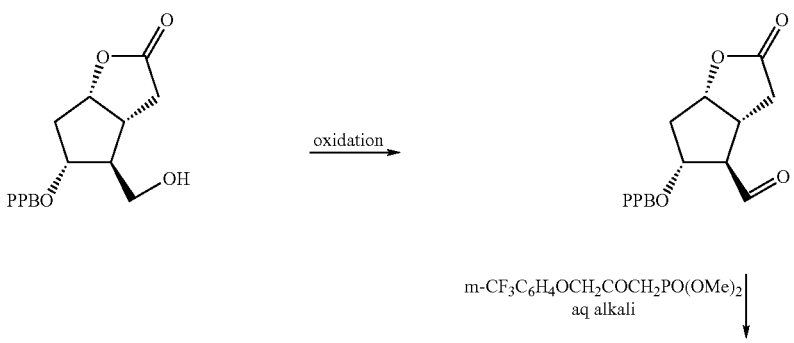

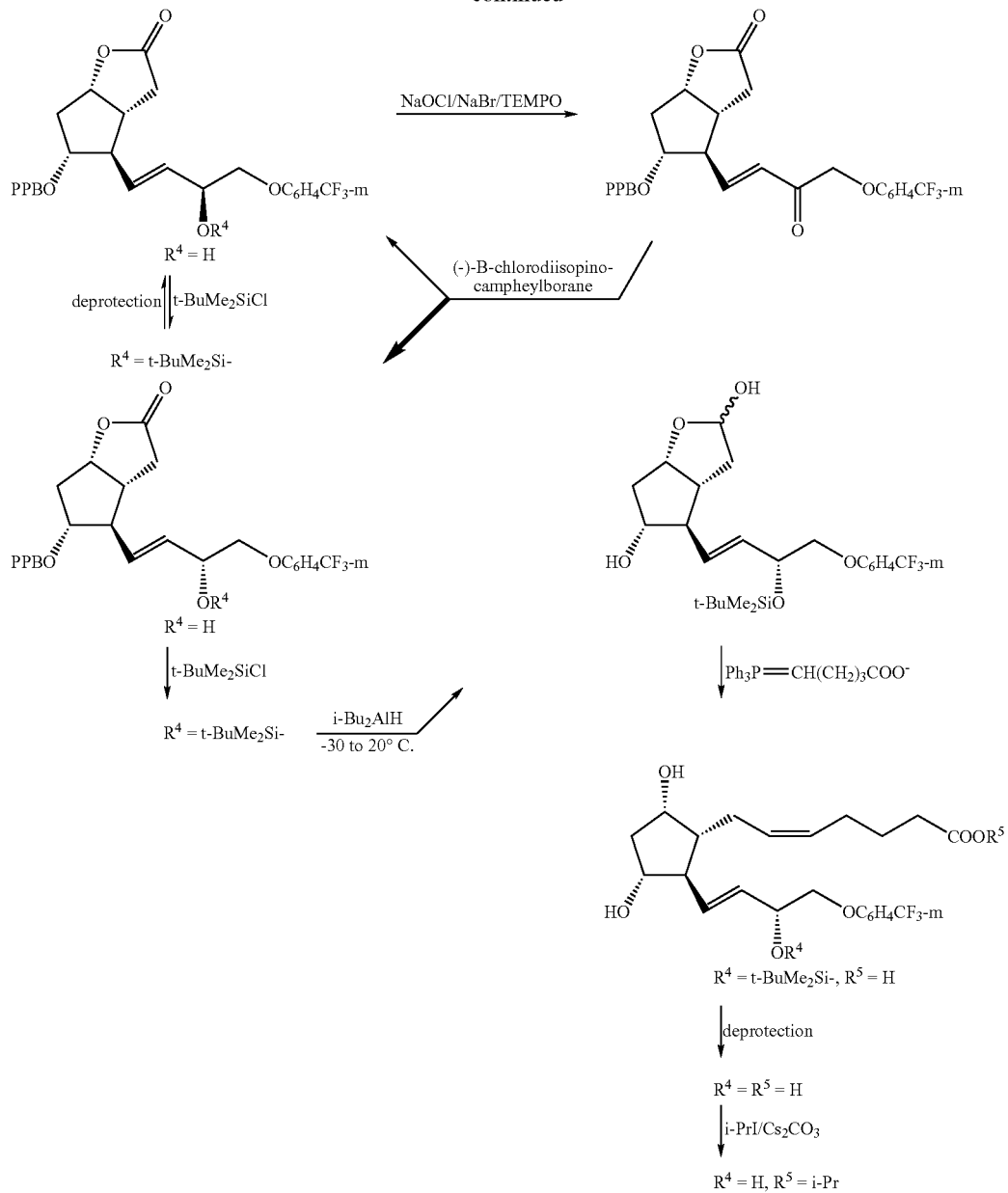
Scheme 5
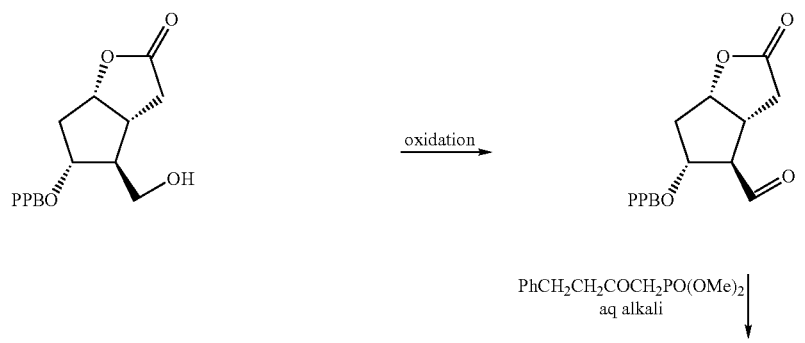

-continued
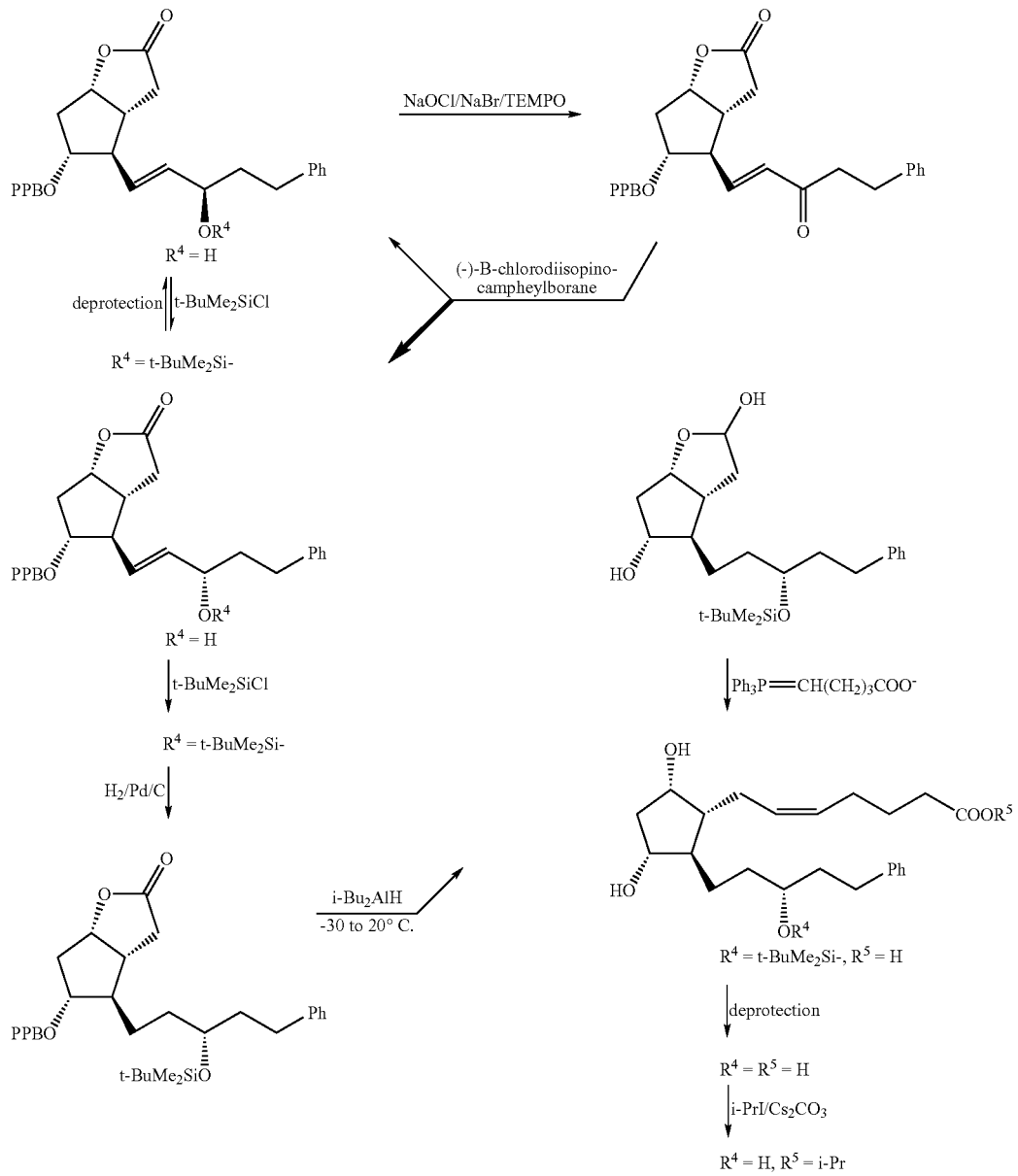
Scheme 6
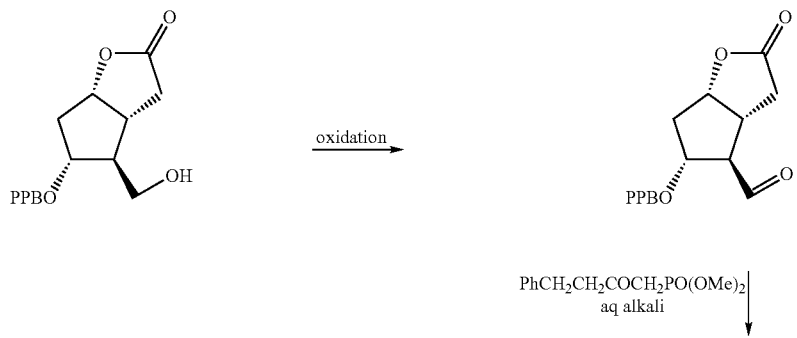

-continued

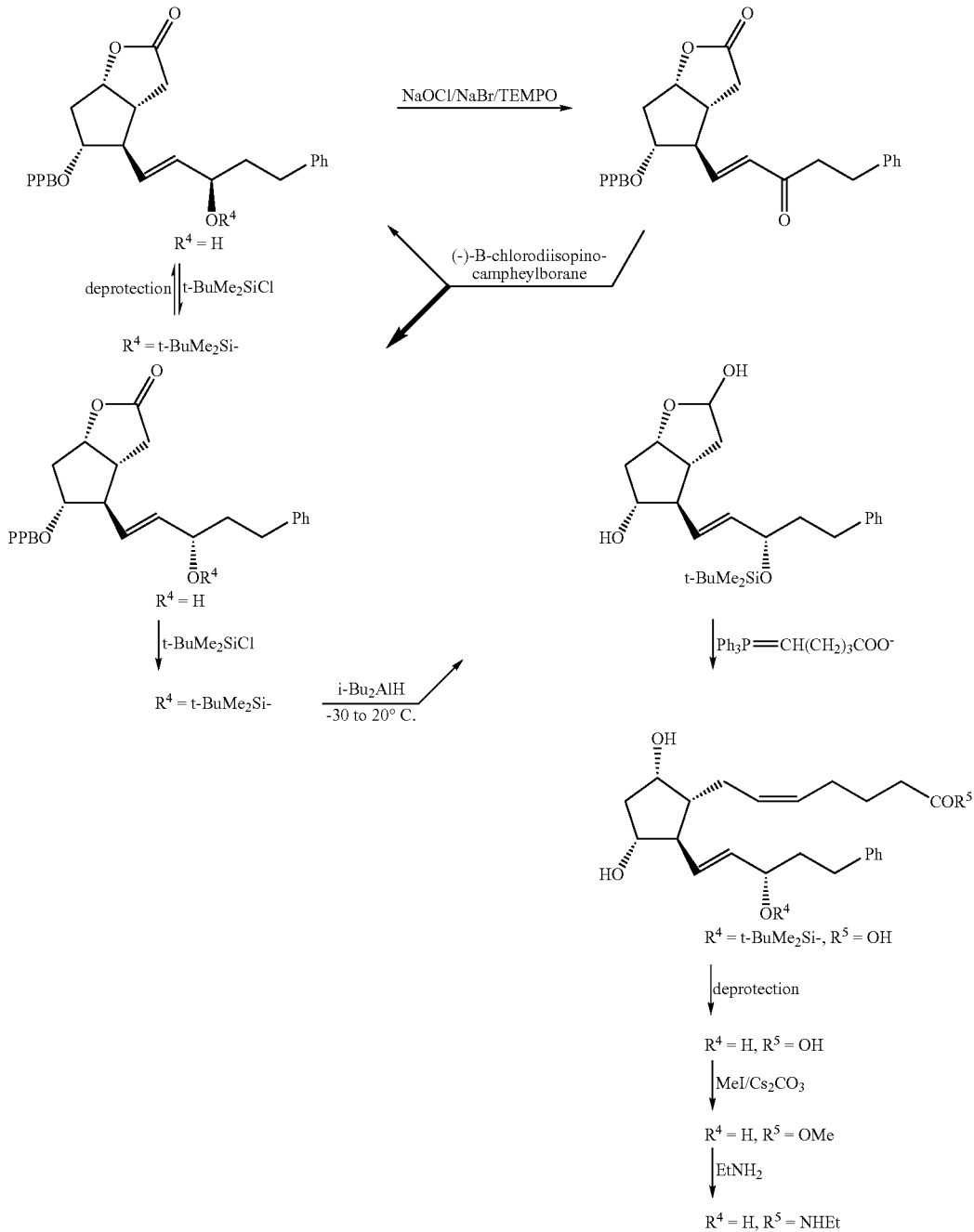

The following abbreviations are used:
α=down;
β=up;
Bn=benzyl;
br.=broad;
Bu=n-butyl;
d=doublet;
DBU=1,8-diazabicyclo[5.4.0]undec-7-ene;
DIBAL-H=diisobutylaluminium hydride;
(−)-DIP-Chloride™=(−)-B-chlorodiisopincampheylborane;
DMAP=4-N,N-dimethylaminopyridine;
DMF=N,N-dimethylformamide;
DMSO=dimethyl sulfoxide;
DRIFTS=diffuse reflectance infrared Fourier-transform spectrum (spectroscopy);
DSC=differential scanning calorimetry;
FT-IR=Fourier-transform infrared;
GC=gas chromatography;
HPLC=high performance liquid chromatography;
HMPA=hexamethylphosphoramide;
INN=International Nonproprietary Name;
IOP=intraocular pressure;
IPA=isopropanol;

IR=infrared;
LC=liquid chromatography
m=multiplet;
MTBE=tert-butyl methyl ether;
NMP=1-methyl-2-pyrrolidinone;
NMR=nuclear magnetic resonance;
PPB=4-phenylbenzoyl;
PPTS=pyridinium p-toluenesulfonate;
rt=room temperature;
s=singlet;
t=triplet;
TEMPO=2,2,6,6-tetramethyl-1-piperidinyloxy, free radical;
THF=tetrahydrofuran;
TGA=thermogravimetric analysis;
USAN=United States Adopted Name;
XRPD=x-ray powder diffraction;

EXAMPLES

Experimental Details:

All reagents and solvents were purchased from Aldrich Chemical Company unless specified otherwise and used without further purification. All reactions were provided under argon or nitrogen atmosphere.

NMR spectra were recorded on a Bruker AM-200 ($^1$H at 200 MHz, $^{13}$C at 50 MHz) and Bruker AM-400 ($^1$H at 400 MHz) instruments using CDCl$_3$ (unless otherwise stated) as a solvent, and chemical shifts are in δ (ppm) relative to internal TMS.

Infrared (IR) absorption spectra were obtained on a Nicolet Impact 410 FT-IR spectrophotometer using a neat liquid sample or dispersion of solid sample material in KBr or Nujol. Infrared DRIFTS spectra were obtained on a Nicolet Impact 410 FT-IR spectrophotometer equipped with Pike Technologies EasiDiff Diffuse Reflectance Accessory using a dispersion of solid sample material in KBr.

Powder x-ray diffraction patterns were obtained by methods known in the art using PANALYTICAL (Philips) X'Pert Pro MPD x-ray powder diffraction system (CuK$_\alpha$ radiation, PW3050/60 goniometer, PW3015/20 X'Celerator detector). The Bragg-Brentano scheme was used for beam focusing.

Melting points were determined in open capillary tubes with Buchi B-545 capillary melting point apparatus or Mettler-Toledo FP-900 Thermosystem with FP-81 HT Melting Point Cell and FP-90 central processor, or Electrothermal IA 9300 digital melting point apparatus and are uncorrected. The melting points generally depend upon level of purity of the samples.

Measurements of difference between the heat flows to a sample and a reference pan that are subject to the same temperature program (differential scanning calorimetry, DSC) were obtained on a Mettler-Toledo DSC 822e Differential Scanning Calorimeter.

Measurements of mass of a sample which is subject to a temperature program (thermogravimetric analysis, TGA) were obtained on a Mettler-Toledo TGA/SDTA 851e Thermogravimetric analyser.

Example 1

1-Chloro-3-[3-(trifluoromethyl)phenoxy]-2-propanol

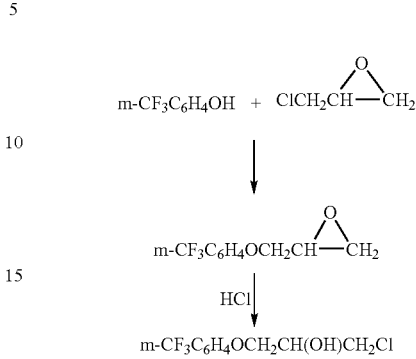

A mixture of m-CF$_3$C$_6$H$_4$OH (48.6 g, 0.30 mol), epichlorohydrin (138.8 g, 1.50 mol) and K$_2$CO$_3$ (20.7 g, 0.15 mol) was stirred at 70° C. for 2 h. Epichlorohydrin was evaporated in vacuo. Water (250 mL) was added and the resulting mixture was extracted with CH$_2$Cl$_2$ (2×50 mL). The combined organic extract was stirred with 32% HCl (50 mL) for 0.5 h at rt. The organic layer separated, dried over Na$_2$SO$_4$, filtered and concentrated in vacuo to give 76.2 g of crude 1-chloro-3-[3-(trifluoromethyl)phenoxy]-2-propanol which was used in next step without additional treatment.

$^1$H NMR (CDCl$_3$) δ: 7.39 (t, J=8.0 Hz, 1H), 7.22 (d, J=8.0 Hz, 1H), 7.13 (s, 1H), 7.07 (d, J=8.0 Hz, 1H), 4.21 (m, 1H), 4.10 (d, J=5.0 Hz, 2H), 3.75 (m, 2H), 2.65 (d, J=6.0 Hz, 1H).

Example 2

1-Chloro-3-[3-(trifluoromethyl)phenoxy]-2-propanone

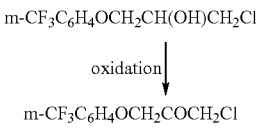

10% aq. NaOCl (900 mL) was added dropwise to a stirred mixture of NaBr (30.9 g, 0.30 mol), NaHCO$_3$ (50.4 g, 0.60 mol), water (200 mL) and a solution of 1-chloro-3-[3-(trifluoromethyl)phenoxy]-2-propanol (80.0 g from Example 1) and TEMPO (0.94 g, 6 mmol) in CH$_2$Cl$_2$ (100 mL) at 0 to 5° C. The mixture was stirred for 0.5 h at the same temperature and 10% aq. Na$_2$S$_2$O$_3$.5H$_2$O (150 mL) was added. The aqueous layer was separated and extracted with CH$_2$Cl$_2$. The combined organic layer was dried over Na$_2$SO$_4$, filtered trough thin layer of silica gel and concentrated in vacuo. A mixture of the residue and hexane (300 mL) was stirred for 1 h at rt and for 1 h at 0 to 5° C. The precipitate was filtered, washed on the filter with cold hexane and dried in vacuo to give 60.5 g of 1-chloro-3-[3-(trifluoromethyl)phenoxy]-2-propanone as off-white crystals: mp 38–39° C. $^1$H NMR (CDCl$_3$) δ: 7.41 (t, J=8.0 Hz, 1H), 7.26 (d, J=8.0 Hz, 1H), 7.13 (s, 1H), 7.0 (d, J=8.0 Hz, 1H), 4.82 (s, 2H), 4.37 (s, 2H).

Example 3

1-Chloro-3-[3-(trifluoromethyl)phenoxy]-2-propanone semicarbazone

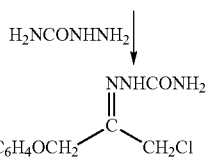

A solution of 1-chloro-3-[3-(trifluoromethyl)phenoxy]-2-propanone (30.3 g, 0.12 mol) in MeOH (100 mL) was added dropwise to a stirred solution of $H_2NCONH_2NH_2 \cdot HCl$ (16.4 g, 0.15 mol) and KOAc (14.7 g, 0.15 mol) in water (250 mL). The mixture was stirred for 1 h. MeOH was evaporated from the mixture at 40° C. (water bath) in vacuo. The obtained mixture was extracted with EtOAc. The combined organic layer was washed with brine, dried over $Na_2SO_4$ and concentrated in vacuo to give 36.8 g (99%) of 1-chloro-3-[3-(trifluoromethyl)phenoxy]-2-propanone semicarbazone as off-white solid.

Example 4

Dimethyl 3-[3-(trifluoromethyl)phenoxy]-2-semicarbazonopropylphosphonate

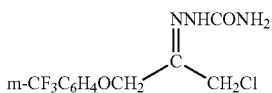

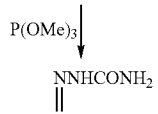

A mixture of 1-chloro-3-[3-(trifluoromethyl)phenoxy]-2-propanone semicarbazone (36.5 g, 0.12 mol), $P(OMe)_3$ (18.6 g, 0.15 mol) and toluene (100 mL) was refluxed for 3 h and cooled to 0° C. The precipitate was filtered off, washed on the filter with cold toluene and recrystallized from toluene to afford 26.8 g (59%) of dimethyl 3-[3-(trifluoromethyl)phenoxy]-2-semicarbazonopropylphosphonate as about 10:1 mixture of two isomers: mp 132–133° C. $^1H$ NMR ($CDCl_3$) (major isomer) δ: 9.40 (s, 1H), 7.37 (t, J=8.0 Hz, 1H), 7.19 (d, J=8.0 Hz, 1H), 7.15 (s, 1H), 7.07 (d, J=8.0 Hz, 1H), 5.80 (br.s, 2H), 4.68 (s, 2H), 3.76 (s, 3H), 3.73 (s, 3H), 3.11 (d, J=12 Hz, 2H).

Example 5

Dimethyl 3-[3-(trifluoromethyl)phenoxy]-2-oxopropylphosphonate

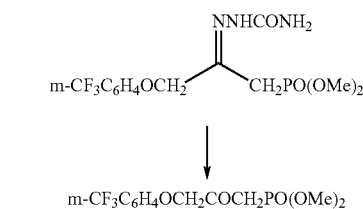

A mixture of dimethyl 3-[3-(trifluoromethyl)phenoxy]-2-semicarbazonopropylphosphonate (19.2 g, 50 mmol), $CH_2Cl_2$ (50 mL) and 6 N HCl (50 mL) was stirred for 2 h at rt. Water (50 mL) was added to the mixture. The organic layer was separated, washed with brine, dried over $Na_2SO_4$, filtered through short column of silica gel and concentrated in vacuo to give 15.1 g (93%) of dimethyl 3-[3-(trifluoromethyl)phenoxy]-2-oxopropylphosphonate as light yellow oil. $^1H$ NMR ($CDCl_3$) δ: 7.42 (t, J=8.0 Hz, 1H), 7.22 (d, J=8.0 Hz, 1H), 7.11 (s, 1H), 7.07 (d, J=8.0 Hz, 1H), 4.77 (s, 2H), 3.80 (s, 3H), 3.74 (s, 3H), 3.23 (d, J=12 Hz, 2H).

Example 6

(3aR,4R,5R,6aS)-4-[3-Oxo-4-[3-(trifluoromethyl)phenoxy]-1E-butenyl]-5-(4-phenylbenzoyloxy)-hexahydro-2H-cyclopenta[b]furan-2-one

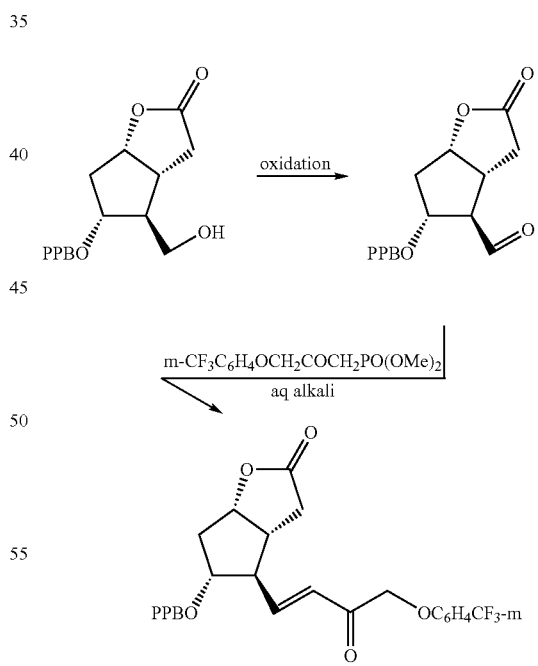

A solution of (−)-Corey lactone 5-(4-phenylbenzoate) (17.6 g, 50.0 mmol) and TEMPO (0.16 g, 1.0 mmol) in $CH_2Cl_2$ (100 mL) was added to a mixture of NaBr (0.5 g, 5.0 mmol), $NaHCO_3$ (12.6 g, 150.0 mmol) and IPA (6.0 g, 100.0 mmol) in water (100 mL). 5% aq. NaOCl (about 150 mL) was added dropwise to the stirred mixture at −5 to 0° C. until disappearance of Corey lactone (TLC monitoring). The obtained mixture was stirred for 0.5 h at the same temperature. The aqueous layer was separated and extracted with CH$_2$Cl$_2$ (50 mL). The combined organic layer was added dropwise over 1 hour to a stirred mixture of a solution of m-CF$_3$C$_6$H$_4$OCH$_2$COCH$_2$PO(OMe)$_2$ (19.6 g, 60.0 mmol) in CH$_2$Cl$_2$ (20 mL) and 30% NaOH (8.0 g, 60.0 mmol) at 0 to −5° C. The mixture was stirred 1 h at the same temperature and treated with 10% aq. citric acid (100 mL). The aqueous layer was separated and extracted with CH$_2$Cl$_2$ (50 mL). The combined organic layer was dried over Na$_2$SO$_4$, filtered through short silica gel column and concentrated in vacuo. The oily residue (26.96 g) was dissolved in refluxed MeOH (150 mL) and cooled in ice bath. The precipitate was filtered off, washed with cold MeOH and dried in vacuo to give 22.1 g (80%) of (3aR,4R,5R,6aS)-4-[3-oxo-4-[3-(trifluoromethyl)phenoxy]-1E-butenyl]-5-(4-phenylbenzoyloxy)-hexahydro-2H-cyclopenta[b]furan-2-one with 99.1% purity by HPLC: mp 115–116° C.; [α]$_D^{20}$ −118.4° (c 1.0, CHCl$_3$). $^1$H NMR (CDCl$_3$) δ: 8.02 (d, J=8 Hz, 2H), 7.58 (m, 4H), 7.40 (m, 4H), 7.22 (d, J=8 Hz, 1H), 7.10 (s, 1H), 6.94 (m, 2H), 6.57 (d, J=15.7 Hz, 1H), 5.35 (q, J=5.5 Hz, 1H), 5.09 (t, J=5.5 Hz, 1H), 4.71 (s, 2H), 2.92 (m, 3H), 2.56 (m, 3H).

The x-ray powder diffraction pattern of crystalline (3aR, 4R,5R,6aS)-4-[3-oxo-4-[3-(trifluoromethyl)phenoxy]-1E-butenyl]-5-(4-phenylbenzoyloxy)-hexahydro-2H-cyclopenta[b]furan-2-one has characteristic peaks expressed in degrees 2θ at approximately 8.5, 8.6, 14.5, 15.6, 16.3, 17.3, 18.3, 18.7, 19.6, 19.9, 20.9, 22.1, 22.3, 22.9, 23.8, 24.2, 24.4, 25.0, 26.5, 27.0, 29.3 and 30.5.

IR DRIFTS (KBr): 2984, 2945, 2900, 1772, 1706, 16367, 1605, 1487, 1451, 1331, 1281, 1225, 1171, 1124, 1062, 977, 899, 878, 811, 746, 703, 600 and 572 cm$^{-1}$.

Example 7

(3aR,4R,5R,6aS)-4-(3-Oxo-5-phenyl-1E-pentenyl)-5-(4-phenylbenzoyloxy)-hexahydro-2H-cyclopenta[b]furan-2-one A solution of (−)-Corey lactone 5-(4-phenylbenzoate) (17.6 g, 50.0 mmol) and TEMPO (0.16 g, 1.0 mmol) in CH$_2$Cl$_2$ (100 mL) was added to a solution of NaBr (0.5 g, 5.0 mmol), NaHCO$_3$ (12.6 g, 150.0 mmol) and IPA (6.0 g, 100.0 mmol) in water (100 mL). 5% aq. NaOCl (about 150 mL) was added dropwise to the stirred mixture at −5 to 0° C. until disappearance of Corey lactone (TLC monitoring). The obtained mixture was stirred for 0.5 h at the same temperature. The aqueous layer was separated and extracted with CH$_2$Cl$_2$ (50 mL). The combined organic layers was added dropwise over 1 h to a stirred mixture of a solution of PhCH$_2$CH$_2$COCH$_2$PO(OMe)$_2$ (15.4 g, 60.0 mmol) in CH$_2$Cl$_2$ (20 mL) and 30% NaOH (8.0 g, 60.0 mmol) at 0–5° C. The mixture was stirred 0.5 h at the same temperature and treated with 10% aq. citric acid (100 mL). The aqueous layer was separated and extracted with CH$_2$Cl$_2$ (50 mL). The combined organic layers were dried over Na$_2$SO$_4$, filtered through short silica gel column and concentrated in vacuo. The oily residue (24.2 g) was dissolved in refluxed EtOH (150 mL) and cooled in ice bath. The precipitate was filtered off, washed with cold EtOH and dried in vacuo to give 20.1 g (84%) of (3aR,4R,5R,6aS)-4-(3-oxo-5-phenyl-1E-pentenyl)-5-(4-phenylbenzoyloxy)-hexahydro-2H-cyclopenta[b]furan-2-one with 99.4% purity by HPLC: mp 129–130° C., [α]$_D^{20}$ −142° (c 1.0, CHCl$_3$); $^1$H NMR spectrum confirms the structure.

The x-ray powder diffraction pattern of crystalline (3aR, 4R,5R,6aS)-4-(3-oxo-5-phenyl-1E-pentenyl)-5-(4-phenylbenzoyloxy)-hexahydro-2H-cyclopenta[b]furan-2-one has characteristic peaks expressed in degrees 2θ at approximately and IR DRIFTS (KBr): and cm$^{-1}$.

Example 8

(3aR,4R,5R,6aS)-4-[3R-3-(t-Butyldimethylsiloxy)-4-[3-(trifluoromethyl)phenoxy]-1E-butenyl]-5-(4-phenylbenzoyloxy)-hexahydro-2H-cyclopenta[b]furan-2-one

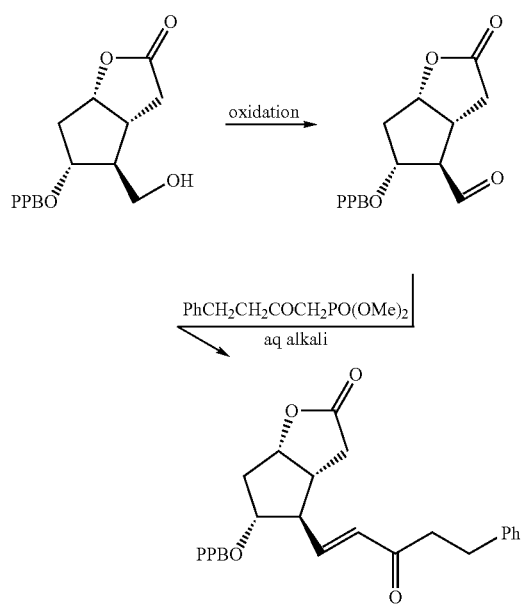

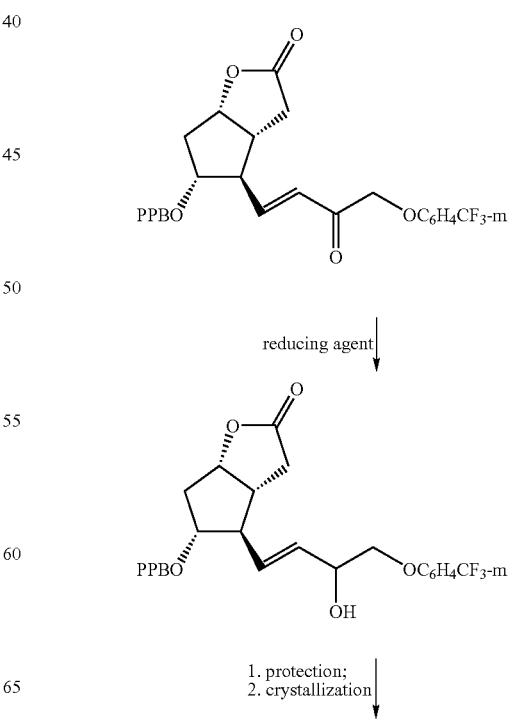

-continued

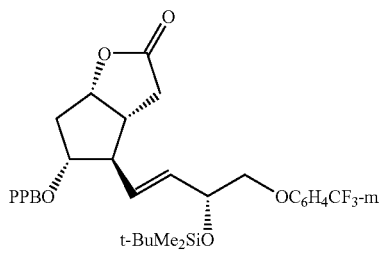

A solution of (−)-B-chlorodiisopinocampheylborane (32.1 g, 100.0 mmol) in THF (50 mL) was added dropwise during 1 h to a stirred solution of (3aR,4R,5R,6aS)-4-[3-oxo-4-[3-(trifluoromethyl)phenoxy]-1E-butenyl]-5-(4-phenylbenzoyloxy)-hexahydro-2H-cyclopenta[b]furan-2-one 7 (27.5 g, 50.0 mmol) in THF (120 mL) at −25 to −30° C. The mixture was stirred overnight at the same temperature and treated with MeOH (30 mL) at rt. The obtained mixture was stirred for 0.5 h and concentrated in vacuo. A solution of the residue in $CH_2Cl_2$ (150 mL) was washed with 10% aq. $NH_4Cl$ (200 mL), dried over $Na_2SO_4$, filtered and concentrated in vacuo. The oily residue contained about 7:1 (HPLC) mixture of 3R/3S isomers of (3aR,4R,5R,6aS)-4-[3R- and 3S-3-hydroxy-4-[3-(trifluoromethyl)phenoxy]-1E-butenyl]-5-(4-phenylbenzoyloxy)-hexahydro-2H-cyclopenta[b]furan-2-one was mixed with t-BuMe₂SiCl (22.6 g, 150.0 mmol), imidazole (20.4 g, 300.0 mmol) and THF (100 mL). The obtained mixture was refluxed for 1 h and concentrated in vacuo. The residue was mixed with $CH_2Cl_2$ (150 mL) and 10% aq. citric acid (200 mL). The aqueous layer was separated and extracted with $CH_2Cl_2$ (2×50 mL). The combined organic layers were dried over $Na_2SO_4$, filtered through short silica gel column and concentrated in vacuo. The residue was crystallized from MeOH to give 23.3 g (70%) of (3aR,4R,5R,6aS)-4-[3R-(t-butyldimethylsiloxy)-4-[3-(trifluoromethyl)phenoxy]-1E-butenyl]-5-(4-phenylbenzoyloxy)hexahydro-2H-cyclopenta[b]furan-2-one as white crystals with 99.9% purity by HPLC: mp 113–115° C.; $[\alpha]_D^{20}$ −89.1° (c 1.0, $CHCl_3$); m/z 689.3 (M+Na⁺). ¹H NMR ($CDCl_3$) δ: 8.03 (d, J=8 Hz, 2H), 7.60 (m, 4H), 7.46 (m, 3H), 7.25 (m, 1H), 7.16 (d, J=8 Hz, 1H), 7.00 (m, 2H), 5.72 (m, 2H), 5.25 (q, J=5.5 Hz, 1H), 5.07 (t, J=5.5 Hz, 1H), 4.48 (m, 1H), 3.82 (m, 2H), 2.81 (m, 3H), 2.54 (m, 2H), 2.23 (m, 1H), 0.84 (s, 9H), 0.03 (d, J=3 Hz, 6H).

The x-ray powder diffraction pattern of crystalline (3aR, 4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one has characteristic peaks expressed in degrees 2θ at approximately 7.1, 10.6, 11.9, 13.2, 14.7, 16.0, 16.4, 16.7, 16.9, 17.6, 17.8, 18.3, 18.7, 19.2, 20.1, 21.4, 22.3, 22.8, 23.7, 23.9, 24.5, 25.4, 26.7, 27.9 and 29.8.

IR DRIFTS (KBr): 3066, 3035, 2958, 2929, 2885, 2858, 1163, 1707, 1588, 1459, 1441, 1329, 1273, 1172, 1131, 1038, 975, 883, 834, 776, 746 and 702 cm⁻¹.

(3aR,4R,5R,6aS)-4-[3R-(t-Butyldimethylsiloxy)-4-[3-(trifluoromethyl)phenoxy]-1E-butenyl]-5-(4-phenylbenzoyloxy)-hexahydro-2H-cyclopenta[b]furan-2-one was characterized by ¹H NMR ($CDCl_3$), powder x-ray diffractometry, IR DRIFTS (KBr) spectroscopy, DSC and TGA as set forth above and in FIGS. 1, 2, 3, 4 and 5.

Example 9

(3aR,4R,5R,6aS)-4-[3R- and 3S-hydroxy-5-phenyl-1E-pentenyl]-5-(4-phenylbenzoyloxy)-hexahydro-2H-cyclopenta[b]furan-2-ones (mixture of 3R- and 3S-isomers)

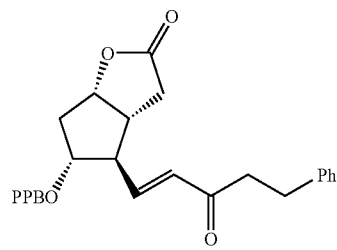

reducing agent ↓

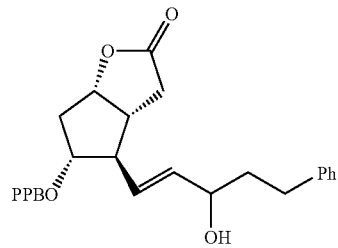

A solution of (−)-B-chlorodiisopinocampheylborane (77.0 g, 0.24 mol) in THF (150 mL) was added dropwise during 2 h to a stirred solution of (3aR,4R,5R,6aS)-4-(3-oxo-5-phenyl-1E-pentenyl)-5-(4-phenylbenzoyloxy)-hexahydro-2H-cyclopenta[b]furan-2-one (57.7 g, 0.12 mol) in THF (300 mL) at −25 to −30° C. The mixture was stirred overnight at the same temperature and treated with MeOH (100 mL) at rt. The obtained mixture was stirred for 0.5 h and concentrated in vacuo. A solution of the residue in $CH_2Cl_2$ (250 mL) was washed with 20% aq. $NH_4Cl$ (250 mL). The aqueous layer was separated and extracted with $CH_2Cl_2$ (2×100 mL). The combined organic layers were dried over $Na_2SO_4$, filtered and concentrated in vacuo. The residue was crystallized from MeOH to give 49.8 g (86%) of (3aR,4R,5R,6aS)-4-[3S- and 3R-hydroxy-5-phenyl-1E-pentenyl]-5-(4-phenylbenzoyloxy)-hexahydro-2H-cyclopenta[b]furan-2-one where 3S/3R was about 97:3 by HPLC.

Example 10

(3aR,4R,5R,6aS)-4-[3S-(t-Butyldimethylsiloxy)-5-phenyl-1E-pentenyl]-5-(4-phenylbenzoyloxy)-hexahydro-2H-cyclopenta[b]furan-2-one

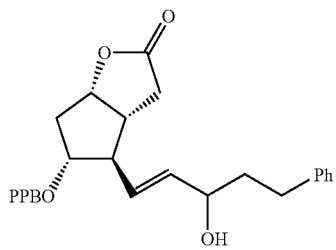

1. protection;
2. crystallization

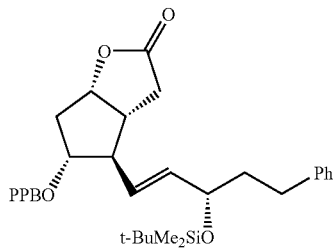

A mixture of (3aR,4R,5R,6aS)-4-[3S- and 3R-hydroxy-5-phenyl-1E-pentenyl]-5-(4-phenylbenzoyloxy)-hexahydro-2H-cyclopenta[b]furan-2-ones where 3S/3R is 97:3 by HPLC (15.4 g, 32.0 mmol), THF (75 mL), t-BuMe$_2$SiCl (7.2 g, 48.0 mmol) and imidazole (6.5 g, 96.0 mmol) was refluxed for 1 h and concentrated in vacuo. The residue was mixed with CH$_2$Cl$_2$ (100 mL) and 10% aq. citric acid (50 mL). The aqueous layer was separated and extracted with CH$_2$Cl$_2$ (50 mL). The combined organic layers were dried over Na$_2$SO$_4$, filtered through the column with silica gel (30 g) and concentrated in vacuo. The residue was crystallized from MTBE to give 16.2 g (76%) of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one as MTBE solvate with 99.8% purity by HPLC: mp 60–64° C.; $[\alpha]^{20}_D$ –84° (c 1, MeCN); $^1$H NMR (CDCl$_3$) δ 8.04 (d, J=8 Hz, 2H), 7.60 (m, 4H), 7.42 (m, 3H), 7.15 (m, 5H), 5.58 (m, 2H), 5.22 (q, J=5.5 Hz, 1H), 5.01 (t, J=5.5 Hz, 1H), 4.12 (q, J=5.5 Hz, 1H), 3.18 (s, 3H), 2.69 (m, 7H), 2.20 (m, 1H), 1.79 (m, 2H), 1.17 (s, 9H), 0.85 (s, 9H), –0.02 (d, J=12 Hz, 6H).

The x-ray powder diffraction pattern of crystalline MTBE solvate of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one has characteristic peaks expressed in degrees 2θ at approximately 6.5, 7.1, 12.2, 12.5, 13.1, 13.6, 14.6, 15.0, 15.8, 16.2, 16.3, 17.0, 17.3, 18.0, 18.2, 18.8, 19.5, 19.7, 20.5, 20.8, 21.0, 21.8, 22.2, 23.0, 23.3, 24.2, 25.5, 26.5 and 26.7.

IR DRIFTS (KBr): 2949, 2931, 2854, 1765, 1715, 1607, 1361, 1266, 1203, 1170, 1118, 1095, 1080, 972, 912, 852, 839, 775, 745, and 699 cm$^{-1}$.

(3aR,4R,5R,6aS)-4-[3S-(t-Butyldimethylsiloxy)-5-phenyl-1E-pentenyl]-5-(4-phenylbenzoyloxy)-hexahydro-2H-cyclopenta[b]furan-2-one MTBE solvate was characterized by $^1$H NMR (CDCl$_3$), powder x-ray diffractometry, IR DRIFTS (KBr) spectroscopy, DSC and TGA as set forth above and in FIGS. 9, 10, 11, 12 and 13.

Example 11

(3aR,4R,5R,6aS)-4-[3R-Hydroxy-4-[3-(trifluoromethyl)phenoxy]-1E-butenyl]-5-(4-phenylbenzoyloxy)-hexahydro-2H-cyclopenta[b]furan-2-one

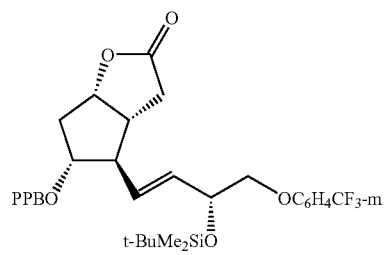

deprotection

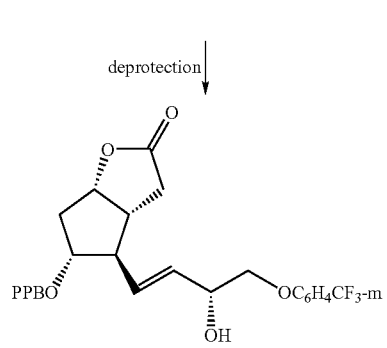

A mixture of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one (0.67 g, 1.0 mmol), 1 M solution of Bu$_4$NF in THF (1.2 mL, 1.2 mmol) and THF (4 mL) was stirred for 1 h at rt, treated with water (20 mL) and extracted with MTBE (2×20 mL). The combined organic layers were washed with brine, dried over Na$_2$SO$_4$ and concentrated in vacuo. The residue was purified by column chromatography on silica gel (eluting with CH$_2$Cl$_2$/MeOH 25:1) to give 0.51 g (92%) of (3aR,4R,5R,6aS)-4-[3R-hydroxy-4-[3-(trifluoromethyl)phenoxy]-1E-butenyl]-5-(4-phenylbenzoyloxy)-hexahydro-2H-cyclopenta[b]furan-2-one with 99.7% purity by HPLC: $[\alpha]_D^{20}$ –104.0° (c 1.0, CHCl$_3$); m/z 575.3 (M+Na$^+$); $^1$H NMR (CDCl$_3$) δ 8.03 (d, J=8 Hz, 2H), 7.60 (m, 4H), 7.45 (m, 4H), 7.18 (d, J=8 Hz, 1H), 7.09 (s, 1H), 6.98 (dd, J=8 Hz, J=2 Hz, 1H), 5.78 (m, 2H), 5.29 (m, 1H), 5.05 (m, 1H), 4.52 (m, 1H), 3.90 (m, 2H), 2.85 (m, 3H), 2.56 (m, 3H), 2.30 (m, 1H).

Example 12

(3aR,4R,5R,6aS)-4-[3S-Hydroxy-5-phenyl-1E-pentenyl]-5-(4-phenylbenzoyloxy)-hexahydro-2H-cyclopenta[b]furan-2-one

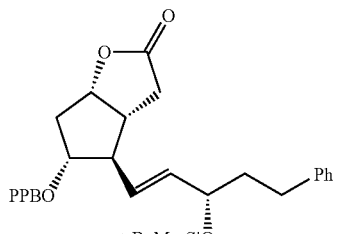

deprotection ↓

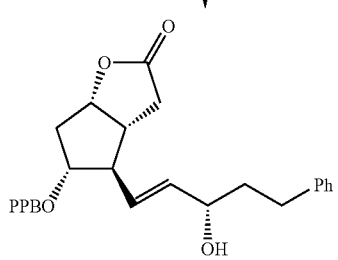

A mixture of (3aR,4R,5R,6aS)-4-[3S-(t-butyldimethylsiloxy)-5-phenyl-1E-butenyl]-5-(4-phenylbenzoyloxy)-hexahydro-2H-cyclopenta[b]furan-2-one (0.69 g, 1.0 mmol), 1 M solution of Bu₄NF in THF (1.2 mL, 1.2 mmol) and THF (4 mL) was stirred for 3 h at rt and treated with water (20 mL). The obtained mixture was extracted with MTBE. The combined organic extracts were dried over Na₂SO₄, filtered and concentrated in vacuo. The residue was crystallized from MeOH to give (3aR,4R,5R,6aS)-4-[3S-hydroxy-5-phenyl-1E-pentenyl]-5-(4-phenylbenzoyloxy)-hexahydro-2H-cyclopenta[b]furan-2-one as white crystals with mp 126–128° C.: ¹H NMR (CDCl₃) is in agreement with the structure.

Example 13

(3aR,4R,5R,6aS)-4-[3S-Hydroxy-4-[3-(trifluoromethyl)phenoxy]-1E-butenyl]-5-(4-phenylbenzoyloxy)-hexahydro-2H-cyclopenta[b]furan-2-one

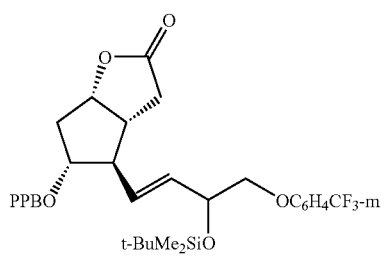

deprotection ↓

-continued

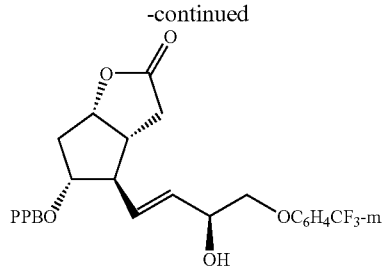

Cleavage of silyl-protective group of (3aR,4R,5R,6aS)-4-[3R- and 3S-(t-butyldimethylsiloxy)-4-[3-(trifluoromethyl)phenoxy]-1E-butenyl]-5-(4-phenylbenzoyloxy)-hexahydro-2H-cyclopenta[b]furan-2-ones about 1:1 3R/3S-isomer mixture following by column chromatography purification on silica gel gives (3aR,4R,5R,6aS)-4-[3S-hydroxy-4-[3-(trifluoromethyl)phenoxy]-1E-butenyl]-5-(4-phenylbenzoyloxy)-hexahydro-2H-cyclopenta[b]furan-2-one. ¹H NMR (CDCl₃) δ: 8.03 (d, J=8 Hz, 2H); 7.60 (m, 4H); 7.45 (m, 4H); 7.18 (d, J=8 Hz, 1H); 7.09 (s, 1H); 7.00 (dd, J=8 Hz, J=2 Hz 1H); 5.77 (m, 2H); 5.28 (m, 1H); 5.07 (m, 1H); 4.52 (m, 1H); 3.87 (m, 2H); 2.85 (m, 3H); 2.56 (m, 3H); 2.30 (m, 1H).

Example 14

(3aR,4R,5R,6aS)-4-[3R-hydroxy-5-phenyl-1E-pentenyl]-5-(4-phenylbenzoyloxy)-hexahydro-2H-cyclopenta[b]furan-2-ones

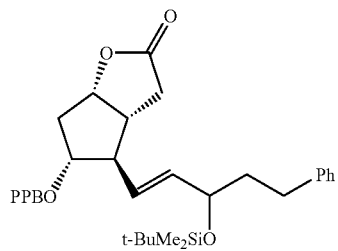

deprotection ↓

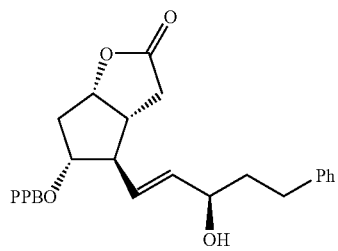

Cleavage of silyl-protective group of (3aR,4R,5R,6aS)-4-[3R- and 3S-(t-butyldimethylsiloxy)-5-phenyl-1E-pentenyl]-5-(4-phenylbenzoyloxy)-hexahydro-2H-cyclopenta[b]furan-2-ones about 1:1 3R/3S-isomer mixture following by column chromatography purification on silica gel gives (3aR,4R,5R,6aS)-4-[3R-hydroxy-5-phenyl-1E-pentenyl]-5-(4-phenylbenzoyloxy)-hexahydro-2H-cyclopenta[b]furan-2-one as white crystals with mp 81–83° C. (Et$_2$O/hexane): [α]$^{D20}$ –124.5° (c 1, MeCN); $^1$H NMR (CDCl$_3$) δ: 7.08–8.05 (m, 14H); 5.51–5.74 (m, 2H); 5.21–5.30 (m, 1H); 5.02–5.07 (m, 1H); 4.09–4.13 (m, 1H); 2.46–2.92 (m, 7H); 2.18–2.28 (m, 1H); 1.66–1.86 (m, 3H). $^{13}$C (CDCl$_3$) δ: 31.6; 34.8; 37.6; 38.7; 42.7; 54.1; 71.6; 79.0; 83.1; 125.9; 127.1; 127.2; 128.2; 128.3; 128.8; 128.9; 130.1; 136.2; 139.9; 141.5; 146.1; 165.9; 176.2.

Example 15

(3aR,4R,5R,6aS)-4-[3-Oxo-4-[3-(trifluoromethyl)phenoxy]-1E-butenyl]-5-(4-phenylbenzoyloxy)-hexahydro-2H-cyclopenta[b]furan-2-one

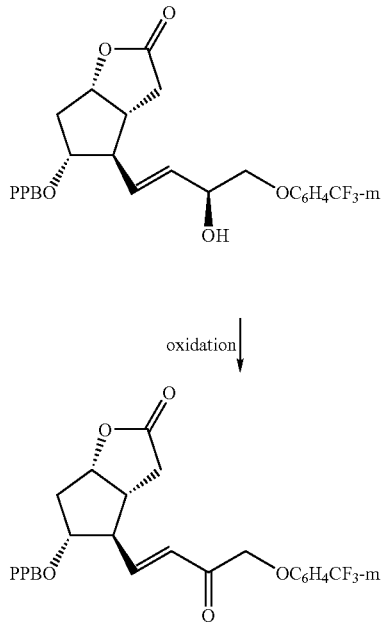

oxidation ↓

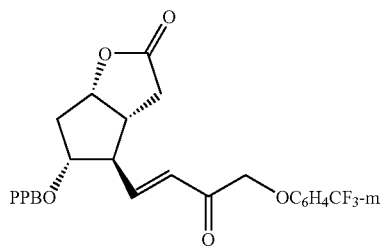

5% aq. NaOCl (60 mL) was added dropwise to a stirred mixture of (3aR,4R,5R,6aS)-4-[3S-hydroxy-4-[3-(trifluoromethyl)phenoxy]-1E-butenyl]-5-(4-phenylbenzoyloxy)-hexahydro-2H-cyclopenta[b]furan-2-one (0.55 g, 1.0 mmol), TEMPO (3 mg, 0.02 mmol), NaBr (10 mg, 0.1 mmol), NaHCO$_3$ (0.25 g, 3.0 mmol), CH$_2$Cl$_2$ (3 mL) and water (3 mL) at rt and the mixture was stirred for 1 h at rt. The aqueous layer was separated and extracted with CH$_2$Cl$_2$. The combined organic layer was dried over Na$_2$SO$_4$, passed through short silica gel column and concentrated in vacuo. The residue was crystallized from MeOH to give 0.44 g (80%) of (3aR,4R,5R,6aS)-4-[3-oxo-4-[3-(trifluoromethyl)phenoxy]-1E-butenyl]-5-(4-phenylbenzoyloxy)-hexahydro-2H-cyclopenta[b]furan-2-one.

Example 16

(3aR,4R,5R,6aS)-4-[3-Oxo-5-phenyl-1E-pentenyl]-5-(4-phenylbenzoyloxy)-hexahydro-2H-cyclopenta[b]furan-2-one

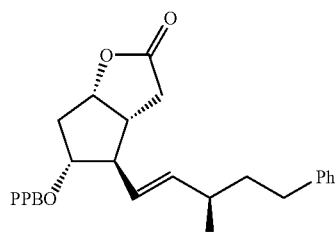

oxidation ↓

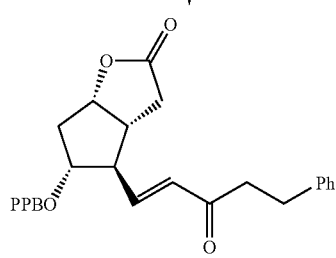

5% aq. NaOCl (40 mL, TLC monitoring) was added dropwise to a stirred mixture of (3aR,4R,5R,6aS)-4-[3R-hydroxy-5-phenyl-1E-pentenyl]-5-(4-phenylbenzoyloxy)-hexahydro-2H-cyclopenta[b]furan-2-one (0.53 g, 1.1 mmol), TEMPO (4 mg, 0.025 mmol), NaBr (12 mg, 0.12 mmol), NaHCO$_3$ (0.3 g, 3.6 mmol), CH$_2$Cl$_2$ (3 mL) and water (3 mL) at rt and the mixture was stirred for 1 h. The aqueous layer was separated and extracted with CH$_2$Cl$_2$ (3 mL). The combined organic layer was dried over Na$_2$SO$_4$ and filtered trough short silica gel column. The residue was concentrated in vacuo and crystallized from MeOH (5 mL) to give 0.37 g (70%) of (3aR,4R,5R,6aS)-4-[3-oxo-5-phenyl-1E-pentenyl]-5-(4-phenylbenzoyloxy)-hexahydro-2H-cyclopenta[b]furan-2-one Example 17

(3aR,4R,5R,6aS)-4-[3R-(t-Butyldimethylsiloxy)-5-phenylpentyl]-5-(4-phenylbenzoyloxy)-hexahydro-2H-cyclopenta[b]furan-2-one

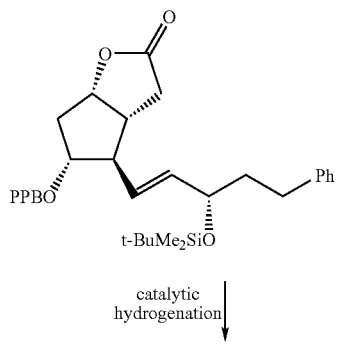

catalytic hydrogenation ↓

-continued

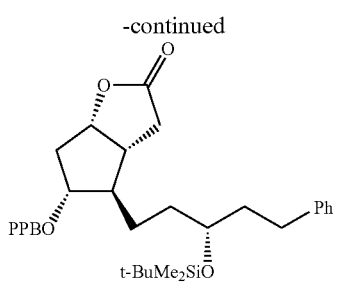

A mixture of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one as MTBE solvate (11.9 g, 17.4 mmol), 10% Pd/C (0.60 g) and toluene (100 mL) was stirred under hydrogen atmosphere at 85 psi overnight at rt, filtered and concentrated in vacuo to give 10.4 g of (3aR,4R,5R,6aS)-4-[3R-(t-butyldimethylsiloxy)-5-phenylpentyl]-5-(4-phenylbenzoyloxy)-hexahydro-2H-cyclopenta[b]furan-2-one as colorless oil with 98.2% purity by HPLC: $[\alpha]^{20}_D$ –84° (c 1.0, MeCN); $^1$H NMR (CDCl$_3$) δ 8.18 (d, J=8 Hz, 2H), 7.63 (m, 4H), 7.46 (m, 3H), 7.22 (m, 5H), 5.22 (m, 1H), 5.05 (m, 1H), 3.72 (m, 1H), 2.90 (m, 1H), 2.63 (m, 4H), 2.32 (m, 3H), 2.08 (m, 1H), 1.69 (m, 5H), 0.87 (s, 9H), –0.01 (d, J=6 Hz, 6H).

Figure 14:
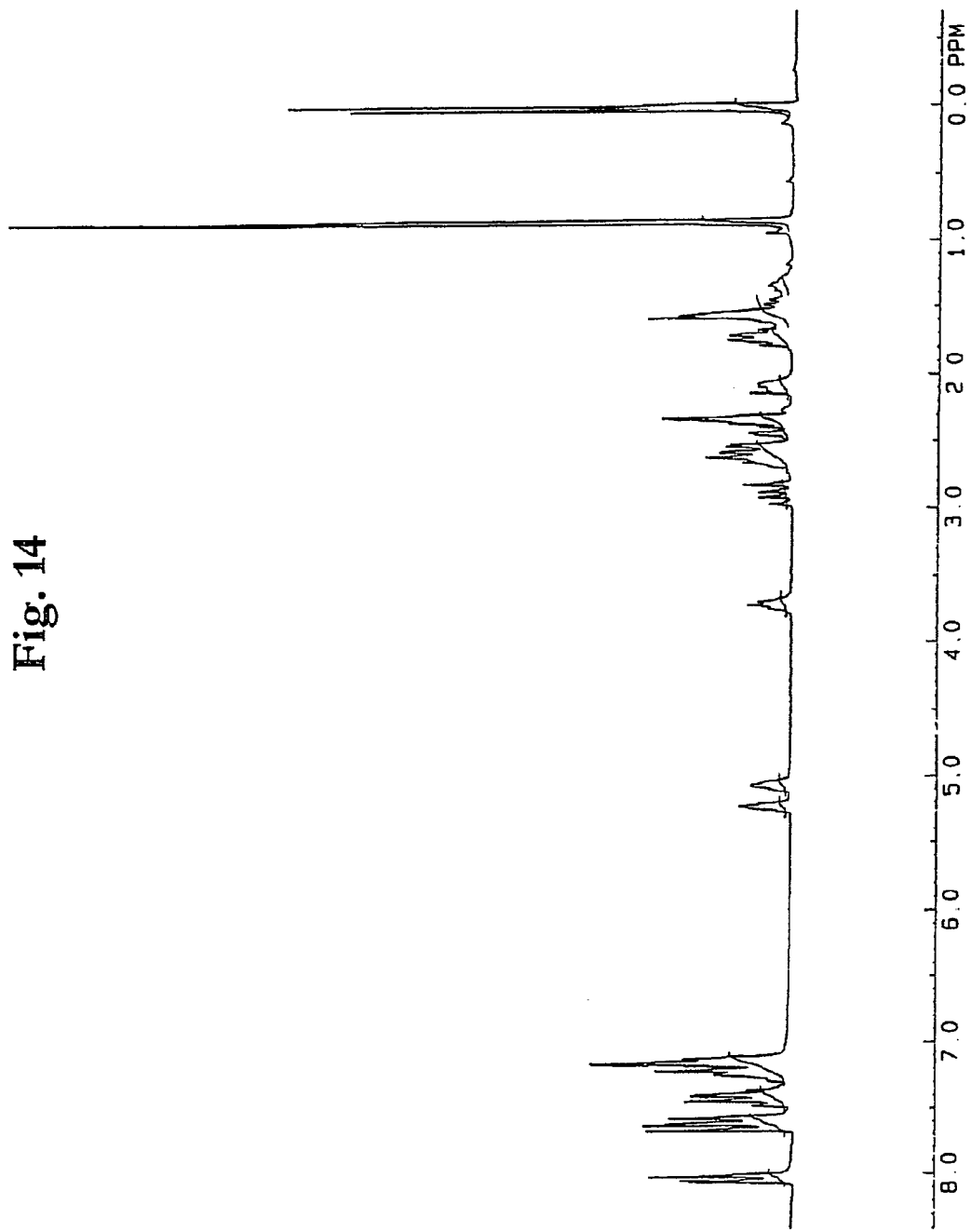
FIG. 14 shows the $^1$H nuclear magnetic resonance (NMR) spectrum of (3aR,4R,5R,6aS)-4-[3R-(t-butyldimethylsiloxy)-5-phenylpentyl]-5-(4-phenylbenzoyloxy)-hexahydro-2H-cyclopenta[b]furan-2-one in CDCl$_3$.

(3aR,4R,5R,6aS)-4-[3R-(t-Butyldimethylsiloxy)-5-phenylpentyl]-5-(4-phenylbenzoyloxy)-hexahydro-2H-cyclopenta[b]furan-2-one was characterized by $^1$H NMR (CDCl$_3$) as set forth above and in FIG. 14.

Example 18

(3aR,4R,5R,6aS)-4-[3R-(t-Butyldimethylsiloxy)-4-[3-(trifluoromethyl)phenoxy]-1E-butenyl]-5-hydroxy-hexahydro-2H-cyclopenta[b]furan-2-ol

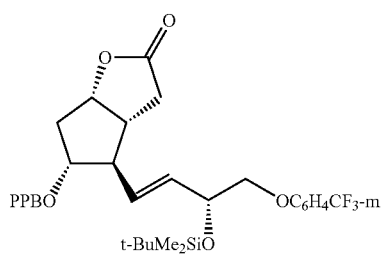

i-Bu$_2$AlH (20% solution in toluene, 55 mL, 66.0 mmol) was added dropwise during 2 h to a stirred solution of (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one (13.4 g, 20.0 mmol) in toluene (100 mL) at –20 to –25° C. The mixture was stirred for 1 h at the same temperature and MeOH (50 mL) was added dropwise over 0.5 h. The mixture was stirred for 0.5 h at rt. The precipitate was filtered off and washed on the filter with MeOH (100 mL). The combined filtrate was concentrated in vacuo. The residue (14.3 g) was separated by column chromatography on silica gel. 4-PhC$_6$H$_4$CH$_2$OH was eluted with CH$_2$Cl$_2$. Oily (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol (9.32 g) was eluted with CH$_2$Cl$_2$/MeOH 25:1 and crystallized from hexane (50 mL) to give 9.0 g (92%) of (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol as white crystals with 99.9% purity by HPLC: mp 112–114° C.; $[\alpha]_D^{20}$ –23.3° (c 1.0, MeOH) m/z 511.2 (M+Na$^+$); $^1$H NMR (CDCl$_3$) δ 7.35 (t, J=8.0 Hz, 1H), 7.21 (d, J=8.0 Hz, 1H), 7.07 (s, 1H), 7.03 (d, J=8.0 Hz, 1H), 5.61 (m, 2H), 4.53 (m, 1H), 3.88 (m, 3H), 2.09 (m, 8H), 0.88 (s, 9H), 0.63 (s, 6H).

The x-ray powder diffraction pattern of crystalline (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol has characteristic peaks expressed in degrees 2θ at approximately 7.0, 11.6, 12.7, 13.1, 13.4, 14.9, 16.3, 16.5, 16.7, 17.4, 17.9, 19.2, 19.4, 20.1, 20.3, 20.5, 21.1, 22.3, 22.6, 23.5, 24.0, 25.6, 26.3 and 28.8.

IR DRIFTS (KBr): 3632, 3301, 2951, 2929, 2860, 1615, 1588, 1491, 1448, 1330, 1294, 1229, 1163, 1126, 1041, 978, 881, 834, 791, 777, 700, 659 and 603 cm$^{-1}$.

Figure 6:
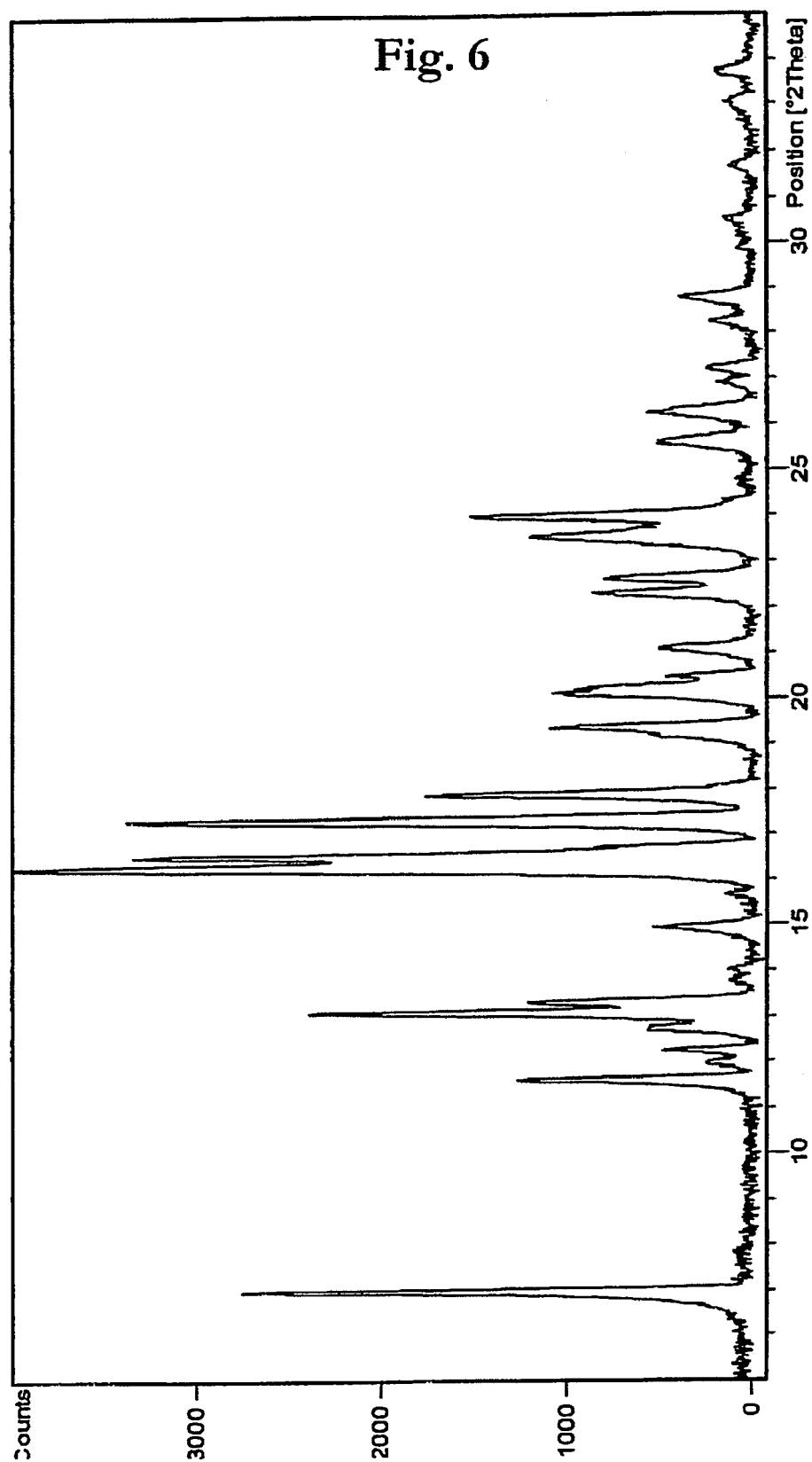
FIG. 6 shows a characteristic x-ray powder diffraction pattern of (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol, according to embodiments of the present invention. Vertical axis: intensity (counts per second); Horizontal axis: 2θ (degrees).
Figure 7:
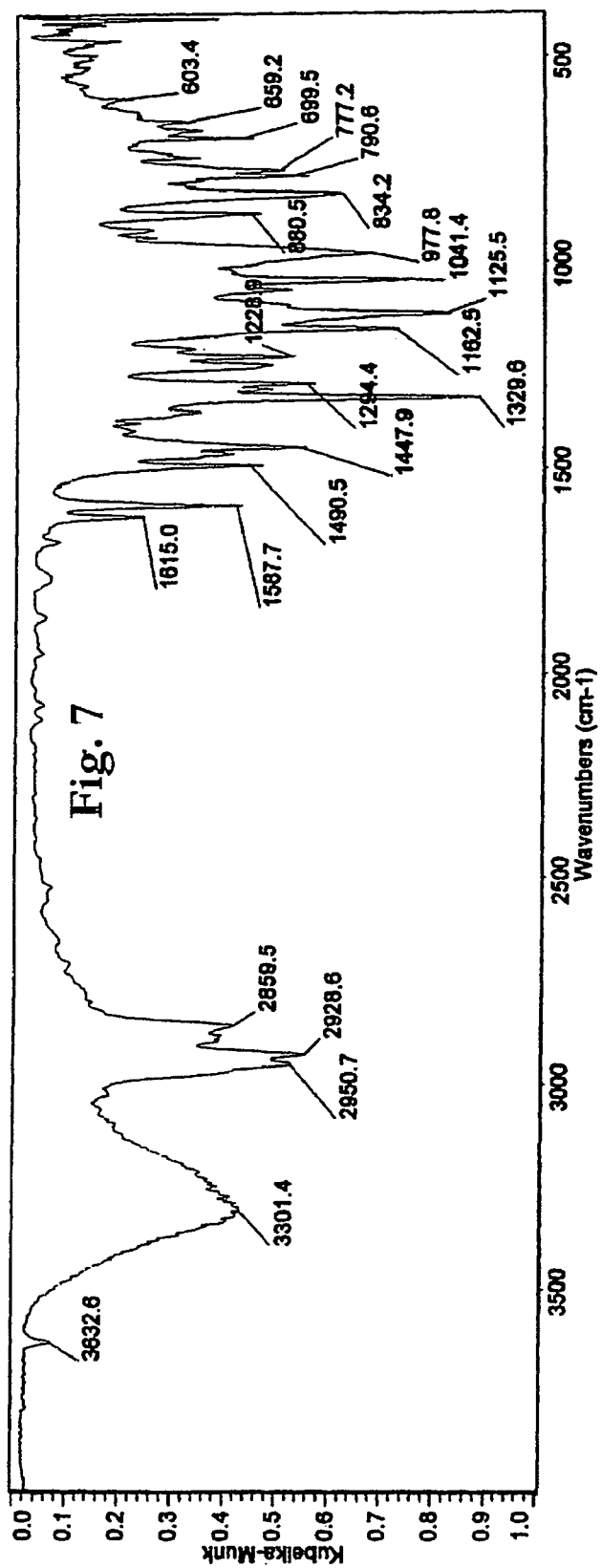
FIG. 7 shows the infrared spectrum (diffuse reflectance, DRIFTS) of (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol in potassium bromide, according to embodiments of the invention.
Figure 8:
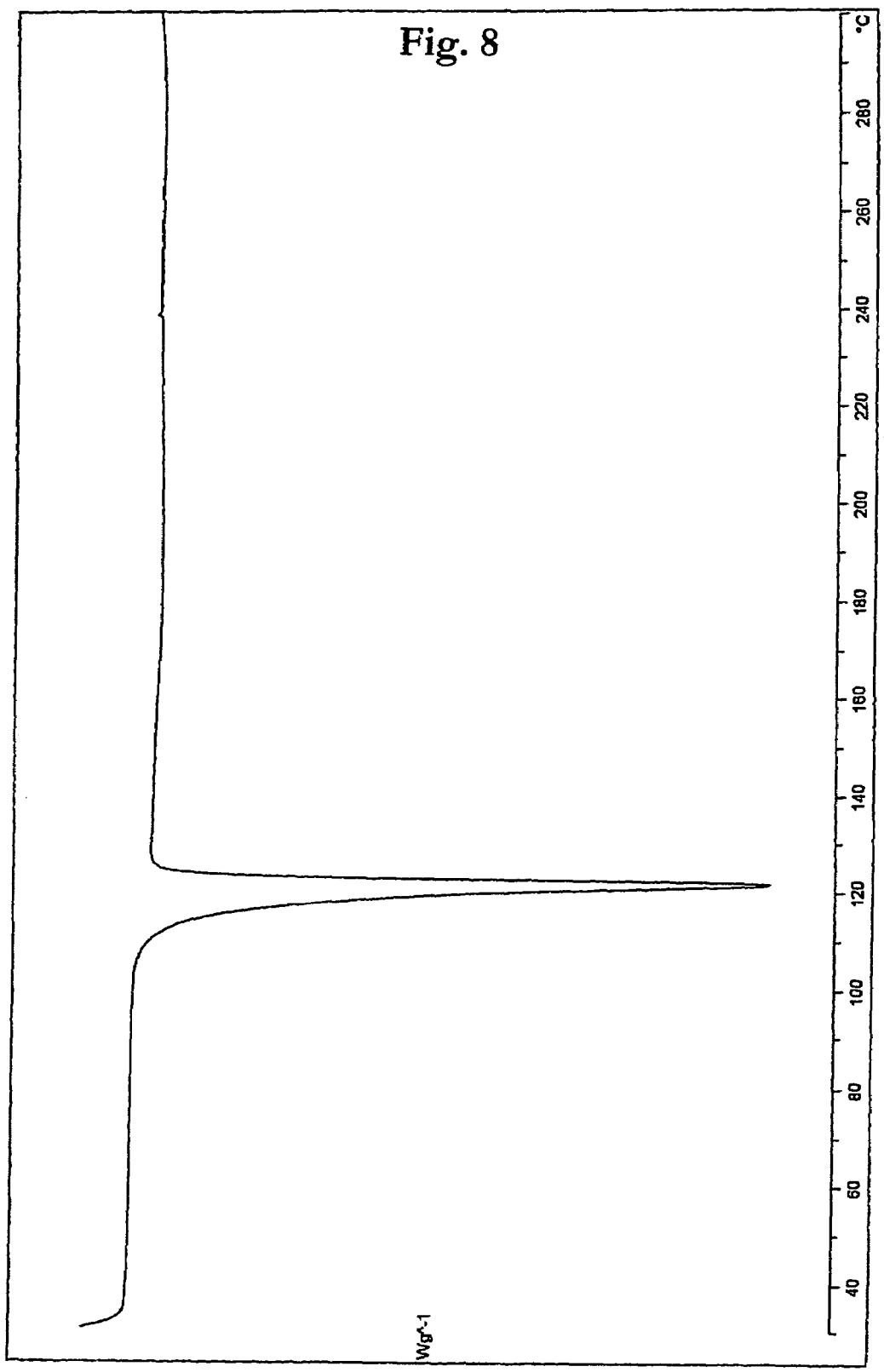
FIG. 8 shows the differential scanning calorimetry (DSC) curve of (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol, according to embodiments of the invention.
Figure 9:
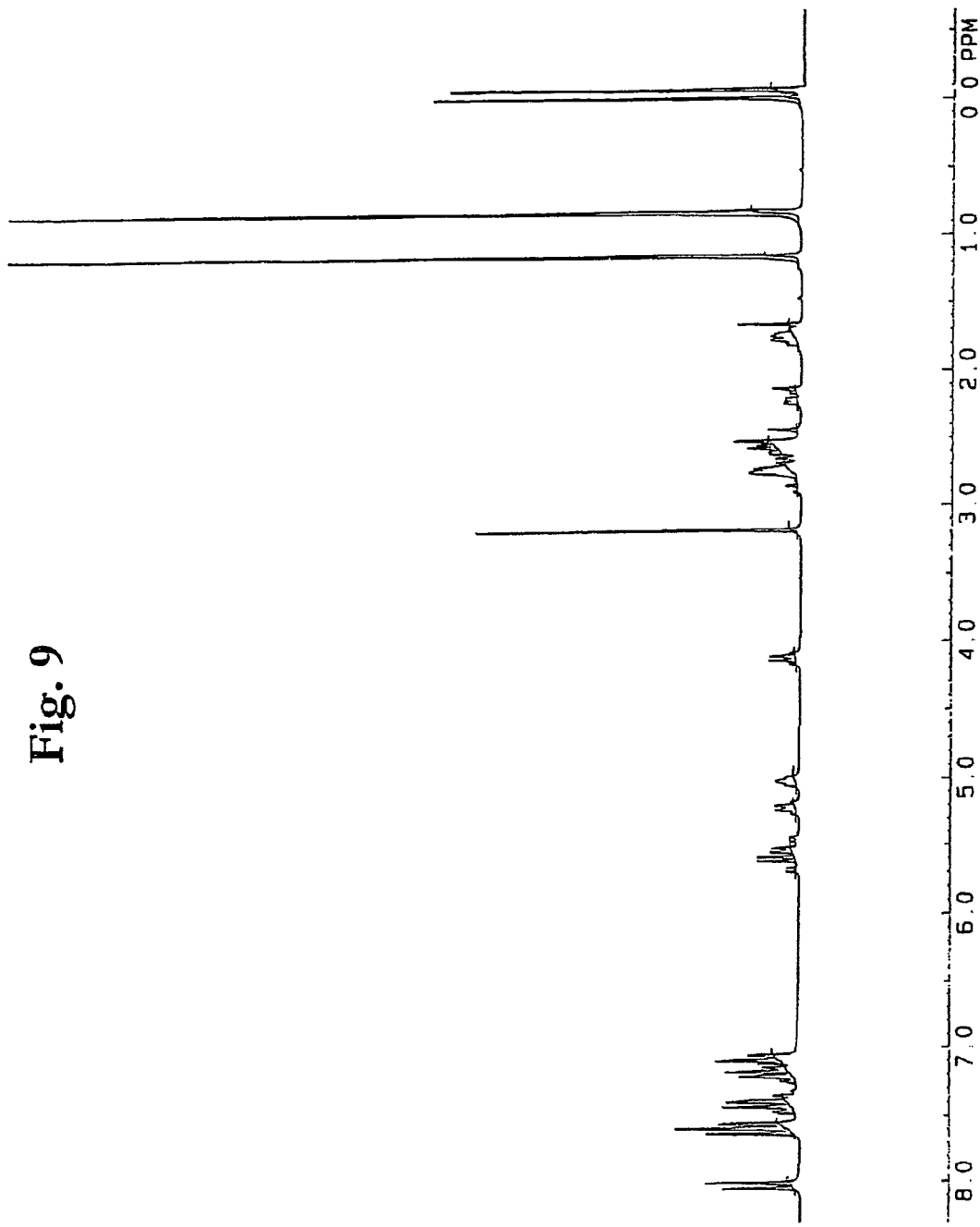
FIG. 9 shows the $^1$H nuclear magnetic resonance (NMR) spectrum of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate in CDCl$_3$.
Figure 10:
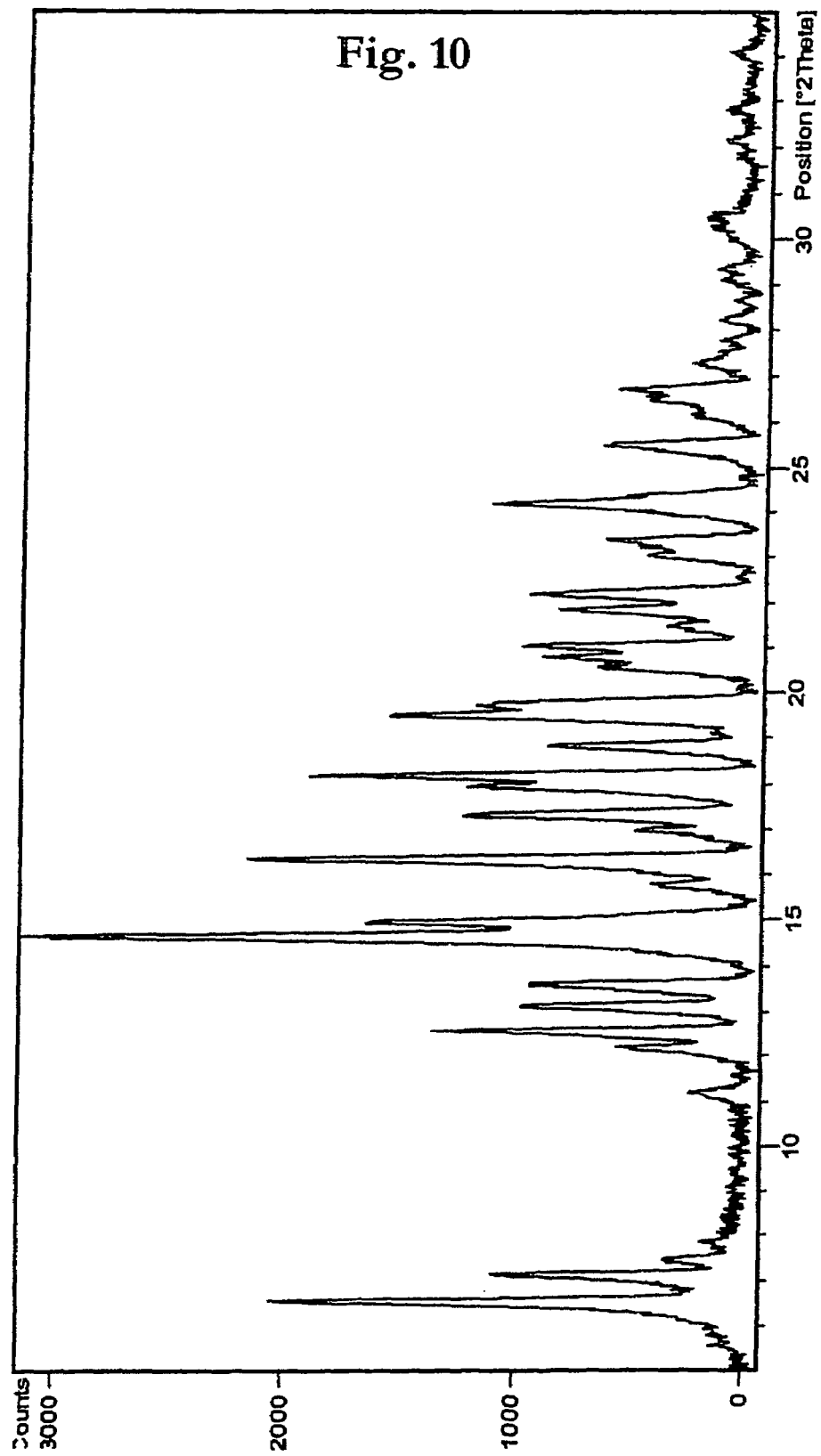
FIG. 10 shows a characteristic x-ray powder diffraction pattern of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate, according to embodiments of the present invention. Vertical axis: intensity (counts per second); Horizontal axis: 2θ (degrees).
Figure 11:
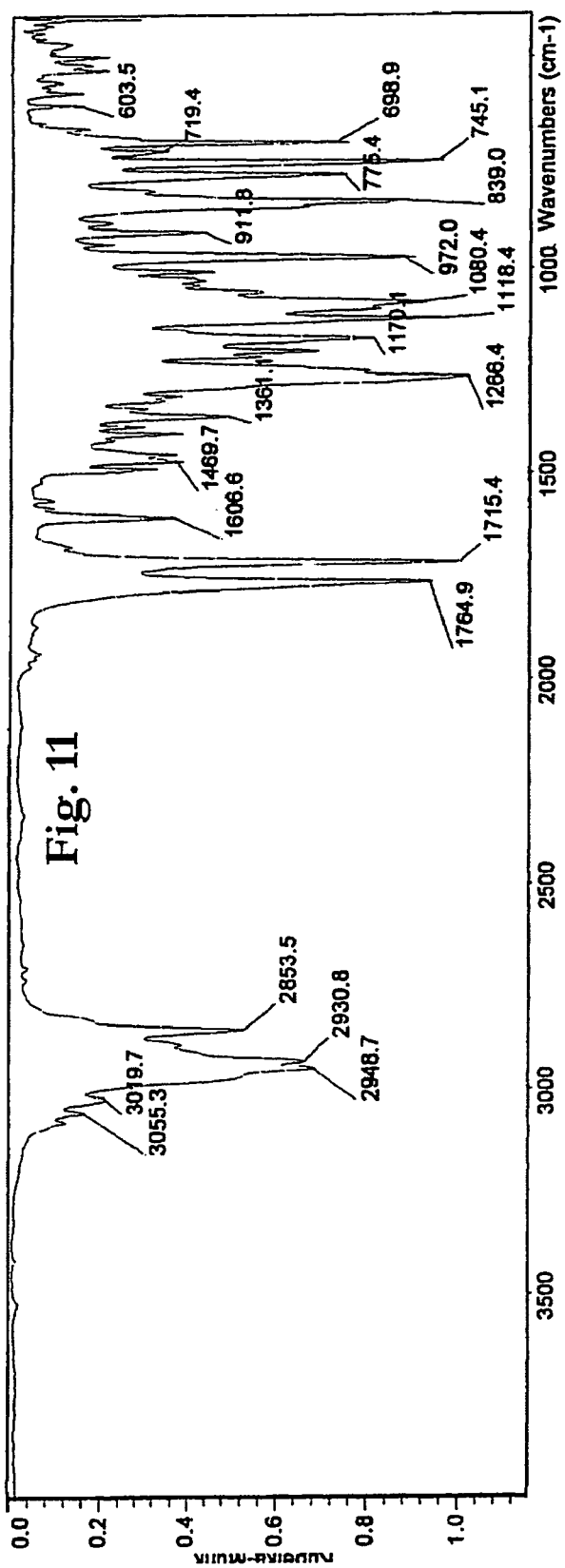
FIG. 11 shows the infrared spectrum (diffuse reflectance, DRIFTS) of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate in potassium bromide, according to embodiments of the invention.
Figure 12:
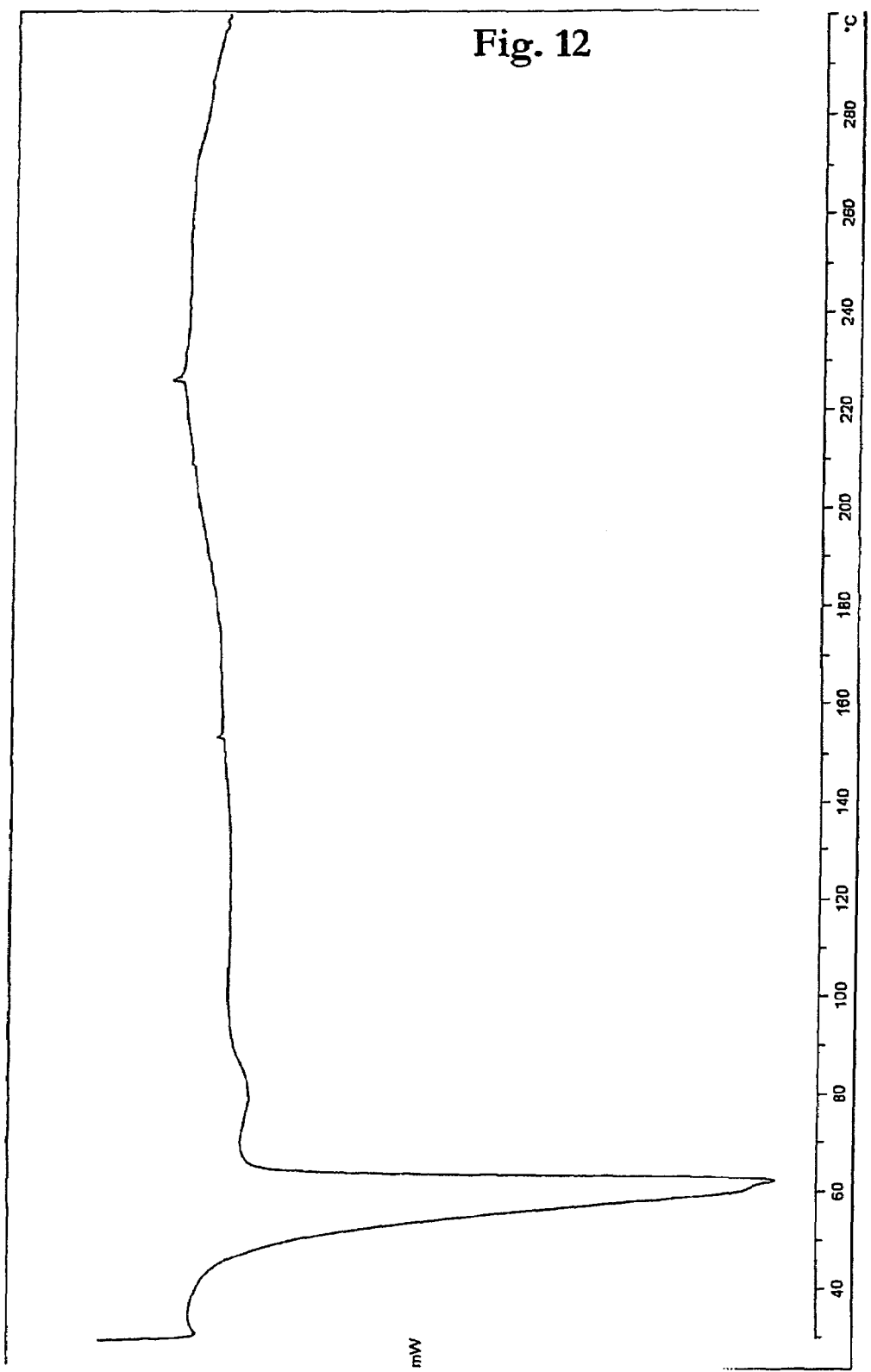
FIG. 12 shows the differential scanning calorimetry (DSC) curve of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate, according to embodiments of the invention.
Figure 13:
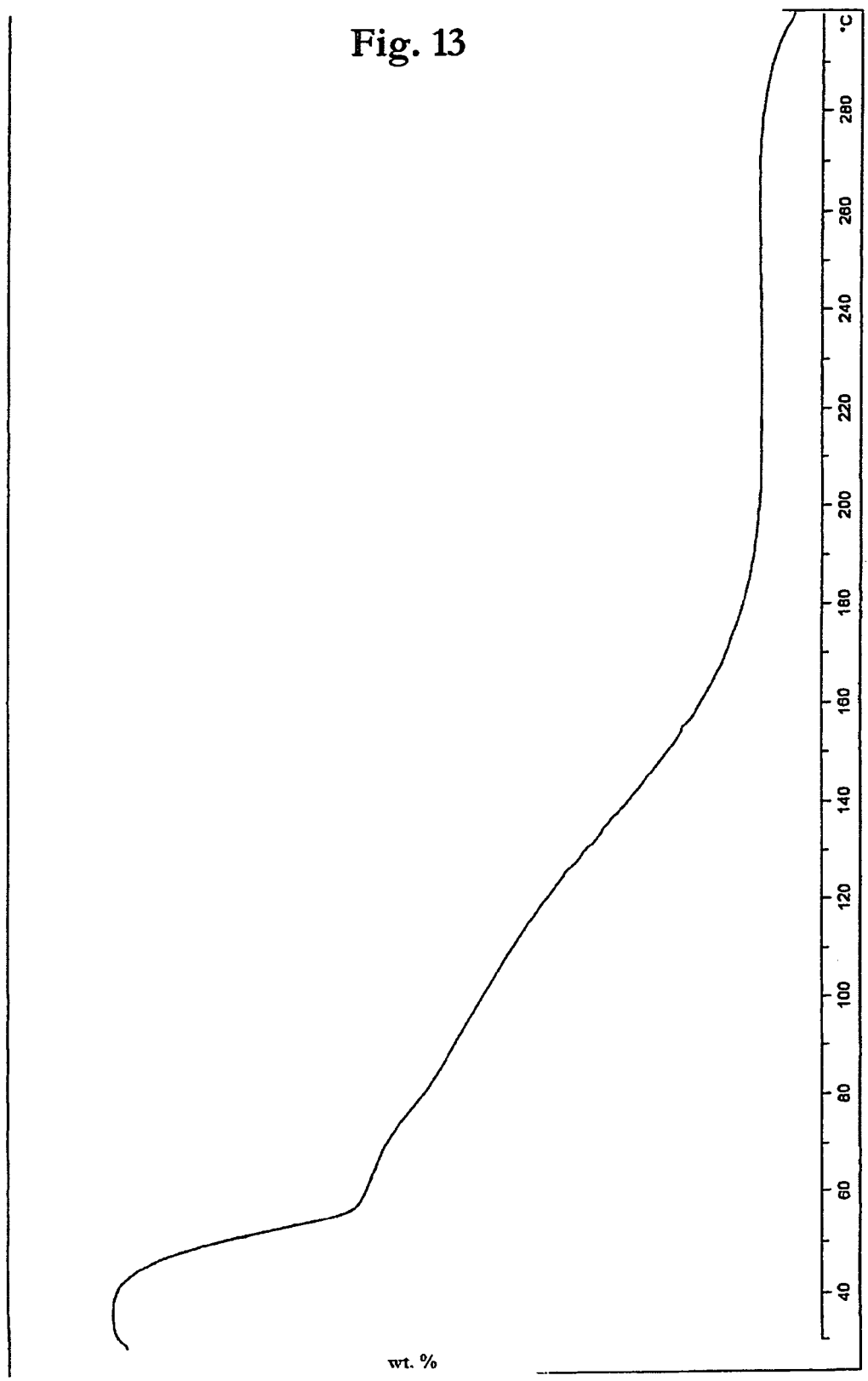
FIG. 13 shows the thermograviometric (TGA) curve of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate, according to embodiments of the invention.

(3aR,4R,5R,6aS)-4-[3R-(t-Butyldimethylsiloxy)-4-[3-(trifluoromethyl)phenoxy]-1E-butenyl]-5-hydroxy-hexahydro-2H-cyclopenta[b]furan-2-ol was characterized by powder x-ray diffractometry, IR DRIFTS (KBr) spectroscopy and DSC as set forth above and in FIGS. 6, 7 and 8.

Example 19

(3aR,4R,5R,6aS)-4-[3R-(t-Butyldimethylsiloxy)-5-phenylpentyl]-5-hydroxy-hexahydro-2H-cyclopenta]b]furan-2-ol

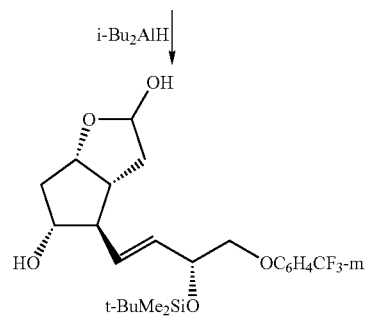

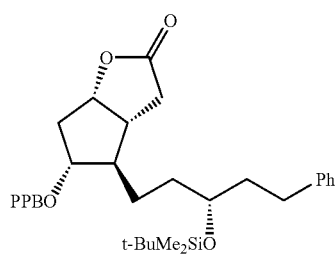

-continued

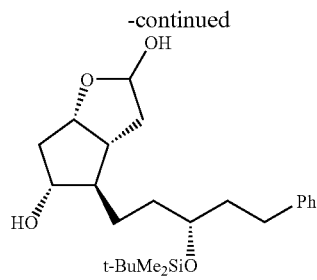

i-Bu$_2$AlH (20% solution in toluene, 49 mL, 59.4 mmol) was added dropwise during 1 h to a stirred solution of (3aR,4R,5R,6aS)-4-[3R-(t-butyldimethylsiloxy)-5-phenyl-pentyl]-5-(4-phenylbenzoyloxy)-hexahydro-2H-cyclopenta[b]furan-2-one (10.8 g, 18.0 mmol) in toluene (100 mL) at −20 to −25° C. The mixture was stirred for 1 h at the same temperature and MeOH (50 mL) was added dropwise over 0.5 h. The mixture was stirred for 1 h at rt. The precipitate was filtered off and washed on the filter with MeOH (100 mL). The combined filtrate was concentrated in vacuo. The residue was separated by column chromatography on silica gel. 4-PhC$_6$H$_4$CH$_2$OH was eluted with CH$_2$Cl$_2$. Oily (3aR, 4R,5R,6aS)-4-[3R-(t-butyldimethylsiloxy)-5-phenylpentyl]-5-hydroxy-hexahydro-2H-cyclopenta[b]furan-2-ol was eluted with CH$_2$Cl$_2$/MeOH 25:1 and crystallized from hexane (30 mL) to give 5.3 g (70%) of (3aR,4R,5R,6aS)-4-[3R-(t-butyldimethylsiloxy)-5-phenylpentyl]-5-hydroxy-hexahydro-2H-cyclopenta[b]furan-2-ol as white solid with 97% purity by HPLC: mp 88–90° C.; $^1$H NMR (CDCl$_3$) δ 7.15 (m, 5H), 5.55 (m, 1H), 4.62 (m, 1H), 3.88 (m, 1H), 3.68 (m, 1H), 2.54 (m, 2H), 2.05 (m, 11H), 1.18 (m, 1H), 0.87 (s, 9H), 0.01 (d, J=3 Hz, 6H).

IR DRIFTS (KBr): 3296, 3021, 2923, 2852, 1600, 1492, 1472, 1458, 1451, 1438, 1373, 1359, 1254, 1067, 1038, 992, 963, 925, 839, 774, 745, 700 and 519 cm$^{-1}$.

Figure 15:
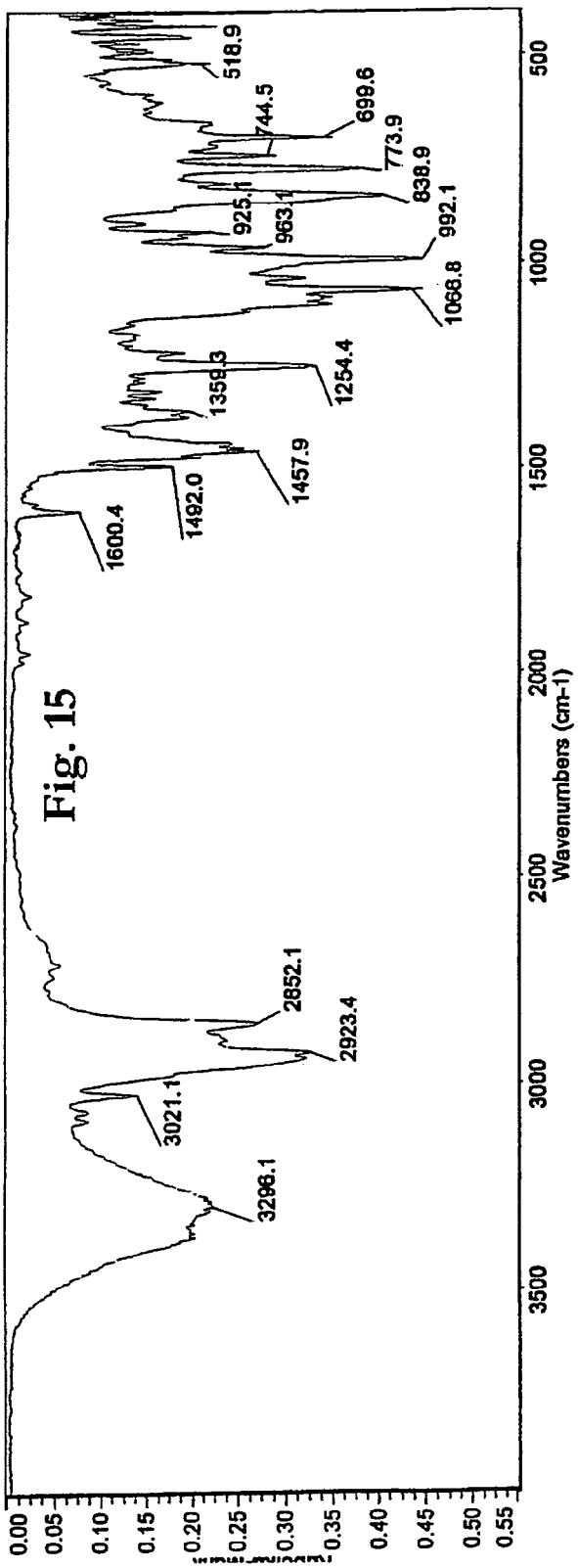
FIG. 15 shows the infrared spectrum (diffuse reflectance, DRIFTS) of (3aR,4R,5R,6aS)-4-[3R-(t-butyldimethylsiloxy)-5-phenylpentyl]-5-hydroxy-hexahydro-2H-cyclopenta[b]furan-2-ol in potassium bromide, according to embodiments of the invention.
Figure 16:
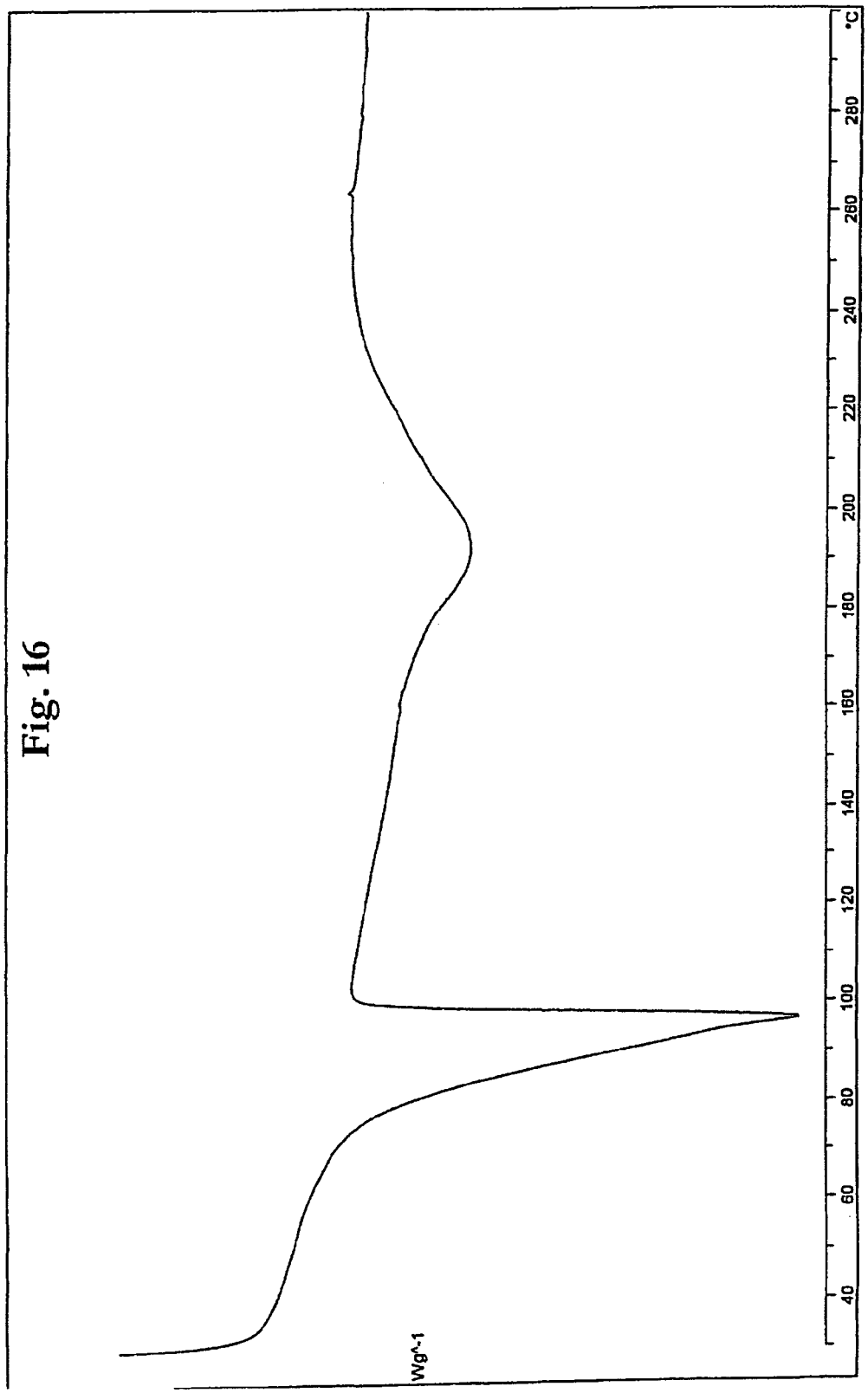
FIG. 16 shows the differential scanning calorimetry (DSC) curve of (3aR,4R,5R,6aS)-4-[3R-(t-butyldimethylsiloxy)-5-phenylpentyl]-5-hydroxy-hexahydro-2H-cyclopenta[b]furan-2-ol, according to embodiments of the invention.
Figure 17:
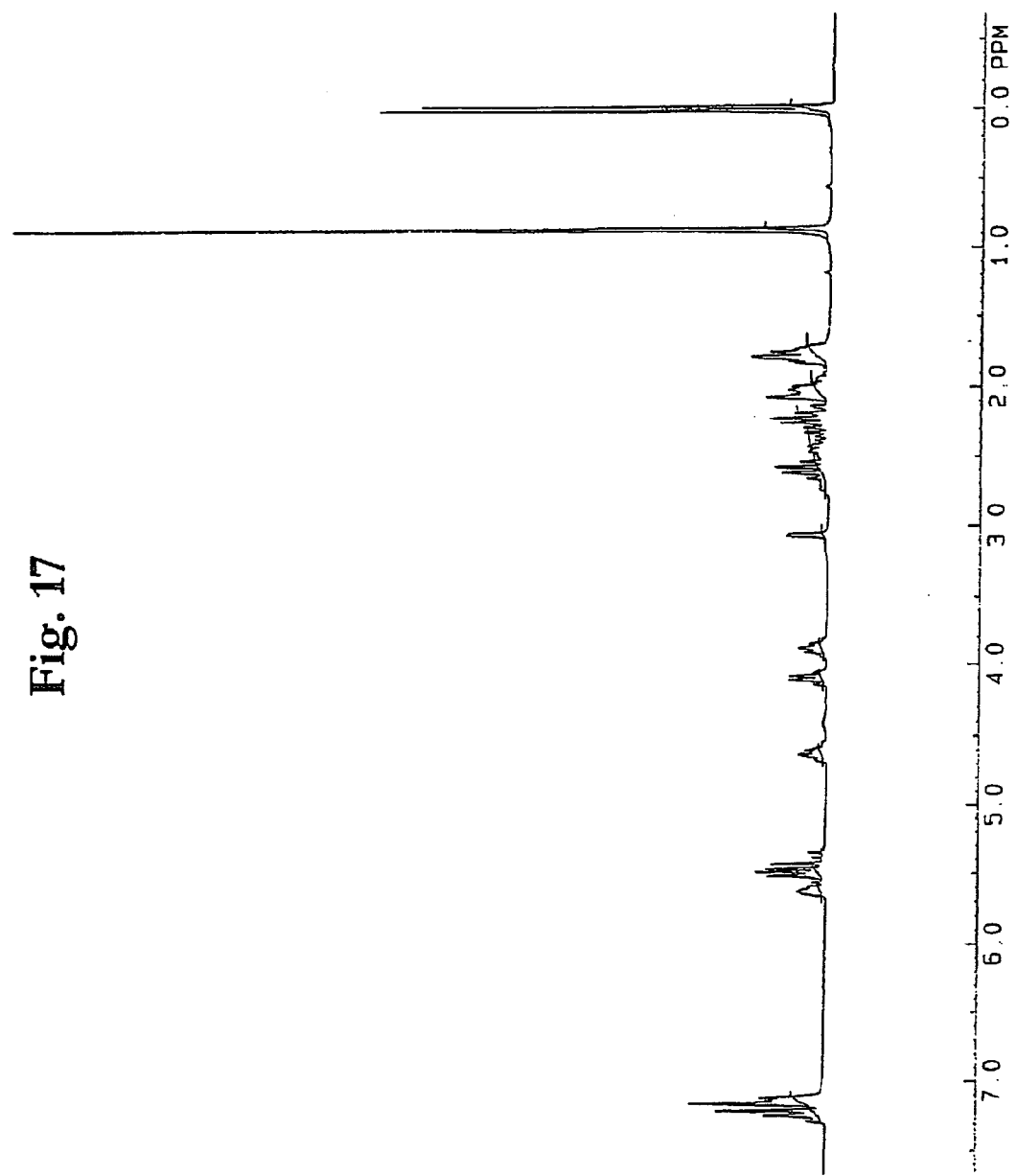
FIG. 17 shows the $^1$H nuclear magnetic resonance (NMR) spectrum of (3aR,4R,5R,6aS)-4-[3S-(t-butyldimethylsiloxy)-5-phenyl-1E-pentenyl]-5-hydroxy-hexahydro-2H-cyclopenta[b]furan-2-ol in CDCl$_3$.
Figure 18:
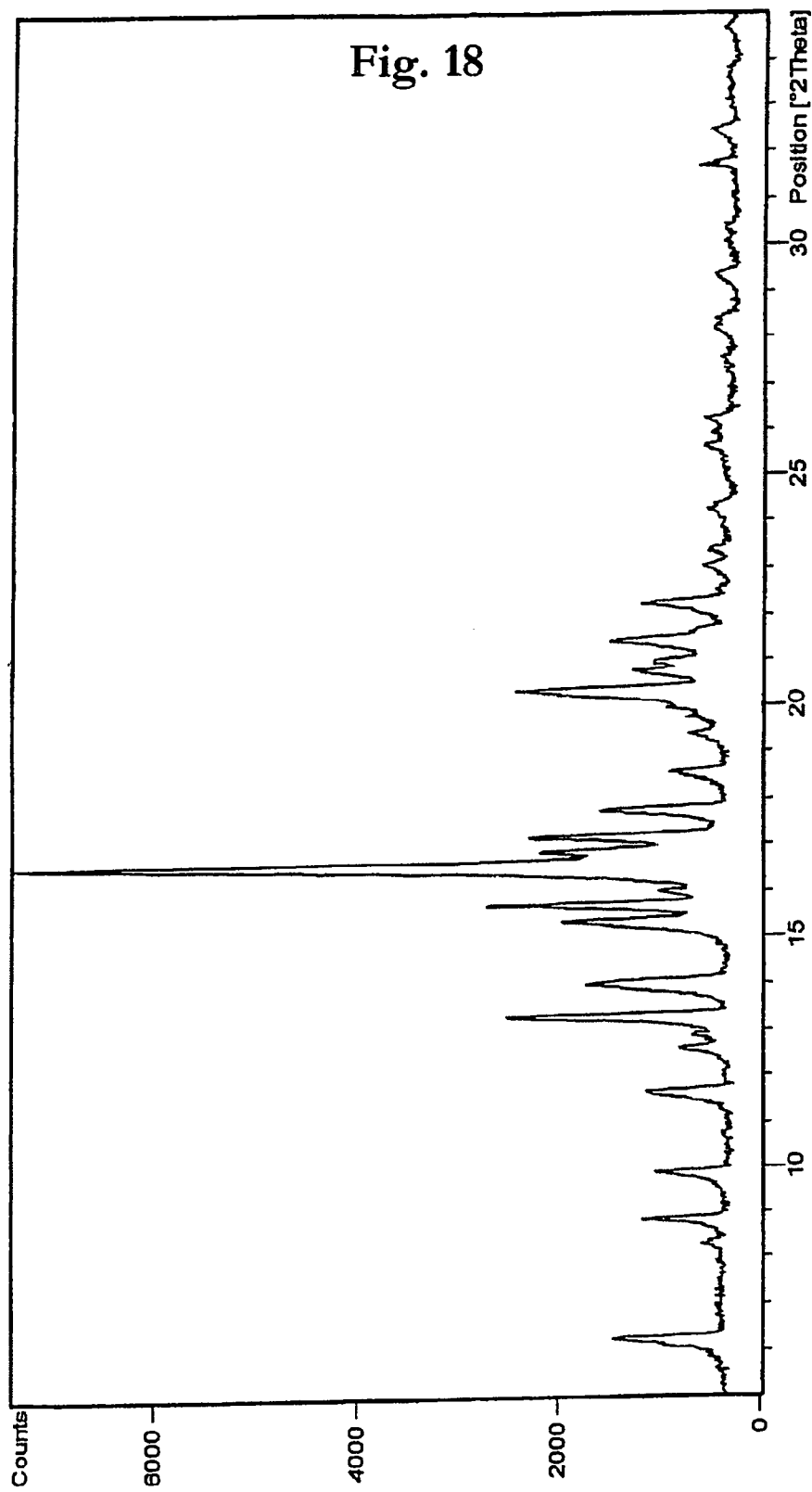
FIG. 18 shows a characteristic x-ray powder diffraction pattern of (3aR,4R,5R,6aS)-4-[3S-(t-butyldimethylsiloxy)-5-phenyl-1E-pentenyl]-5-hydroxy-hexahydro-2H-cyclopenta[b]furan-2-ol, according to embodiments of the present invention. Vertical axis: intensity (counts per second); Horizontal axis: 2θ (degrees).
Figure 19:
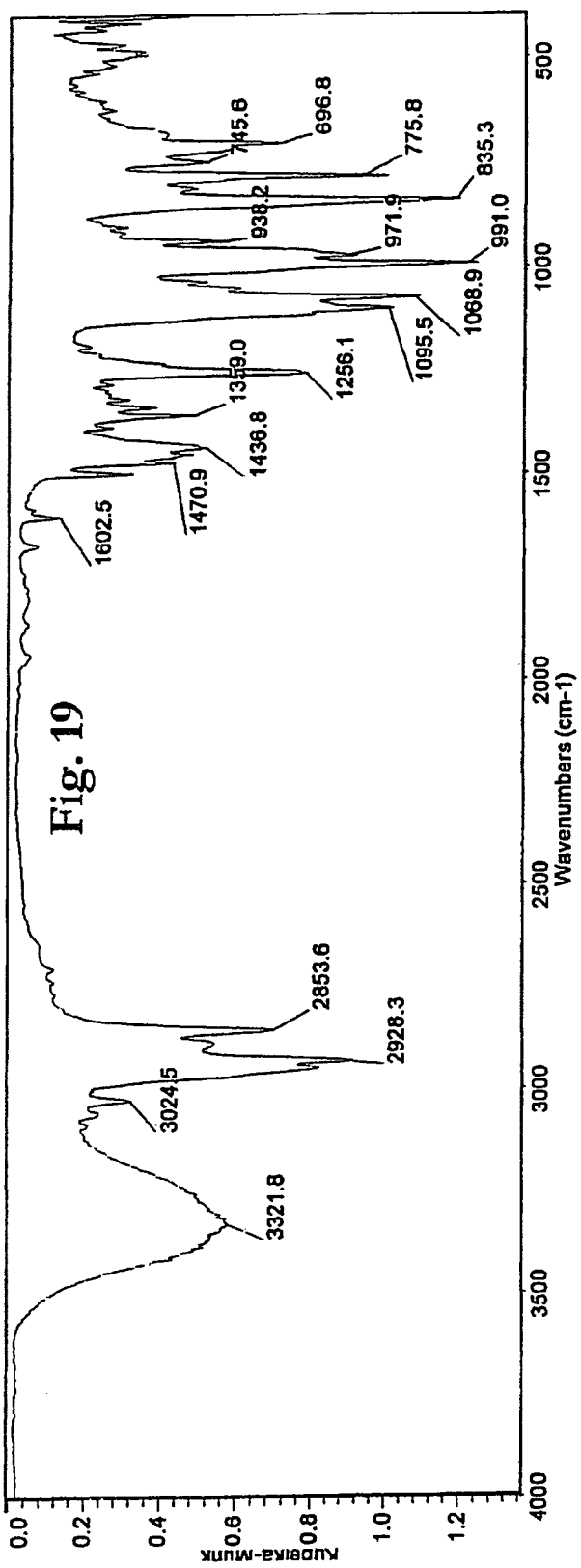
FIG. 19 shows the infrared spectrum (diffuse reflectance, DRIFTS) of (3aR,4R,5R,6aS)-4-[3S-(t-butyldimethylsiloxy)-5-phenyl-1E-pentenyl]-5-hydroxy-hexahydro-2H-cyclopenta[b]furan-2-ol in potassium bromide, according to embodiments of the invention.
Figure 20:
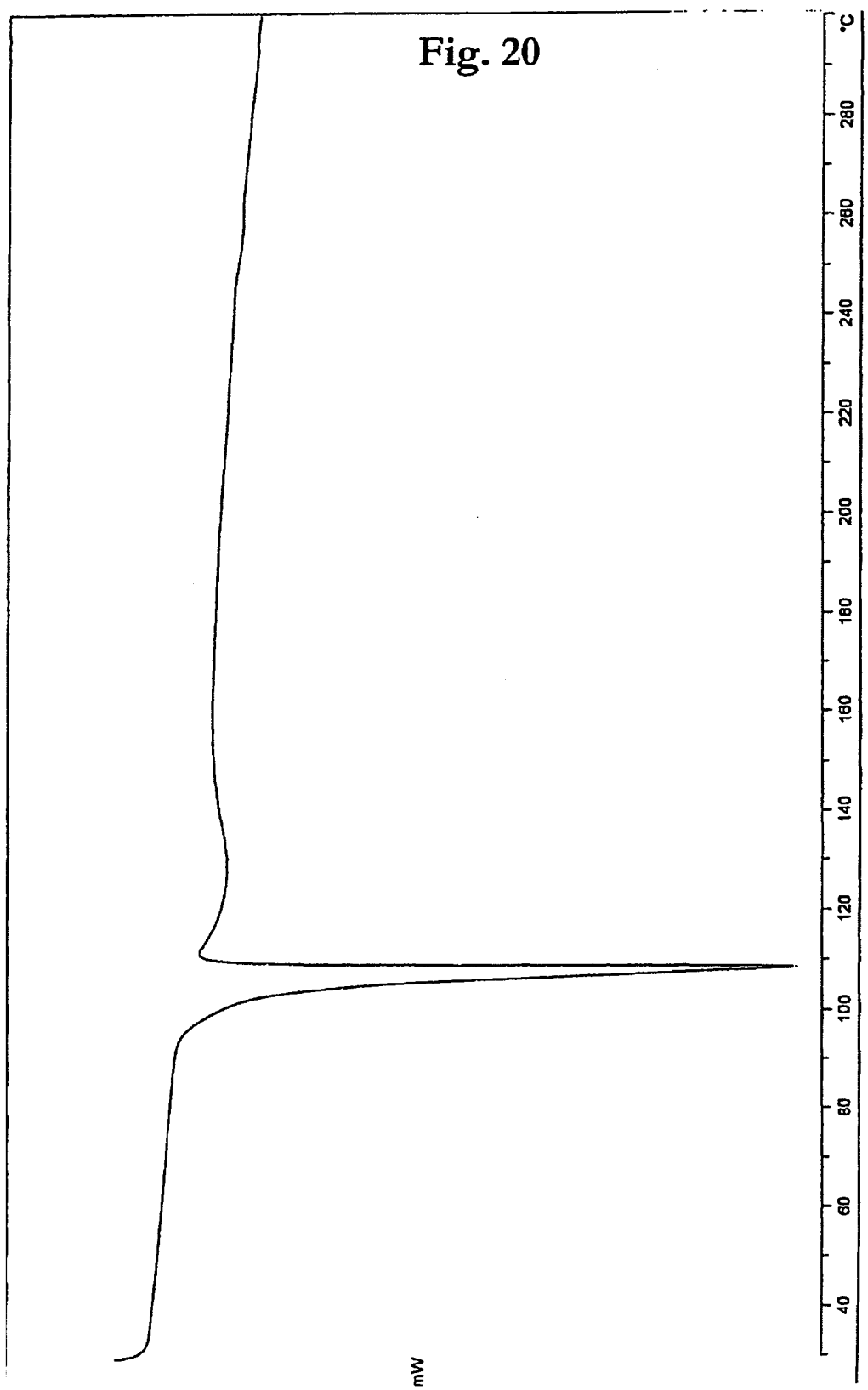
FIG. 20 shows the differential scanning calorimetry (DSC) curve of (3aR,4R,5R,6aS)-4-[3S-(t-butyldimethylsiloxy)-5-phenyl-1E-pentenyl]-5-hydroxy-hexahydro-2H-cyclopenta[b]furan-2-ol, according to embodiments of the invention.
Figure 21:
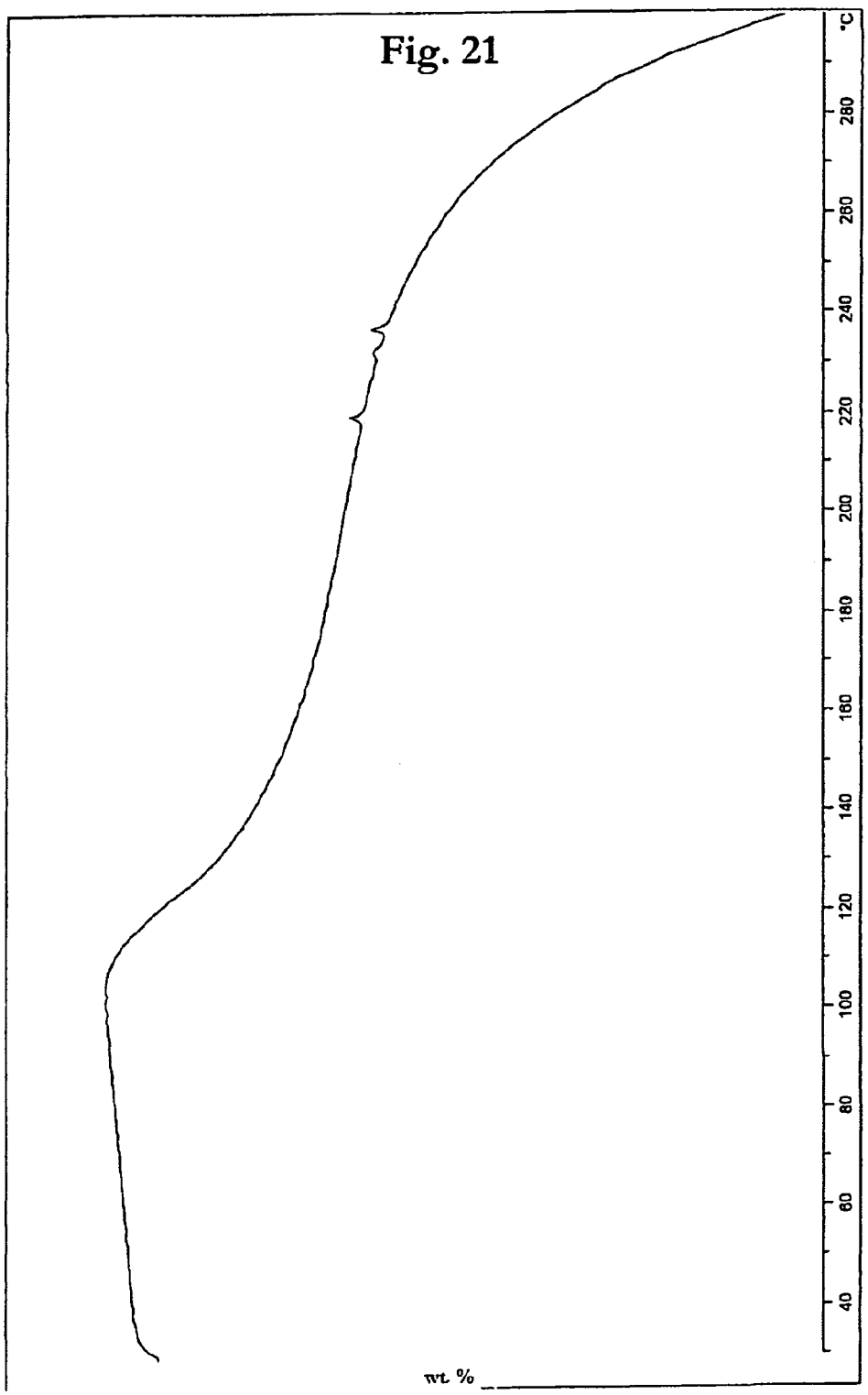
FIG. 21 shows the thermograviometric (TGA) curve of (3aR,4R,5R,6aS)-4-[3S-(t-butyldimethylsiloxy)-5-phenyl-1E-pentenyl]-5-hydroxy-hexahydro-2H-cyclopenta[b]furan-2-ol, according to embodiments of the invention.
Figure 22:
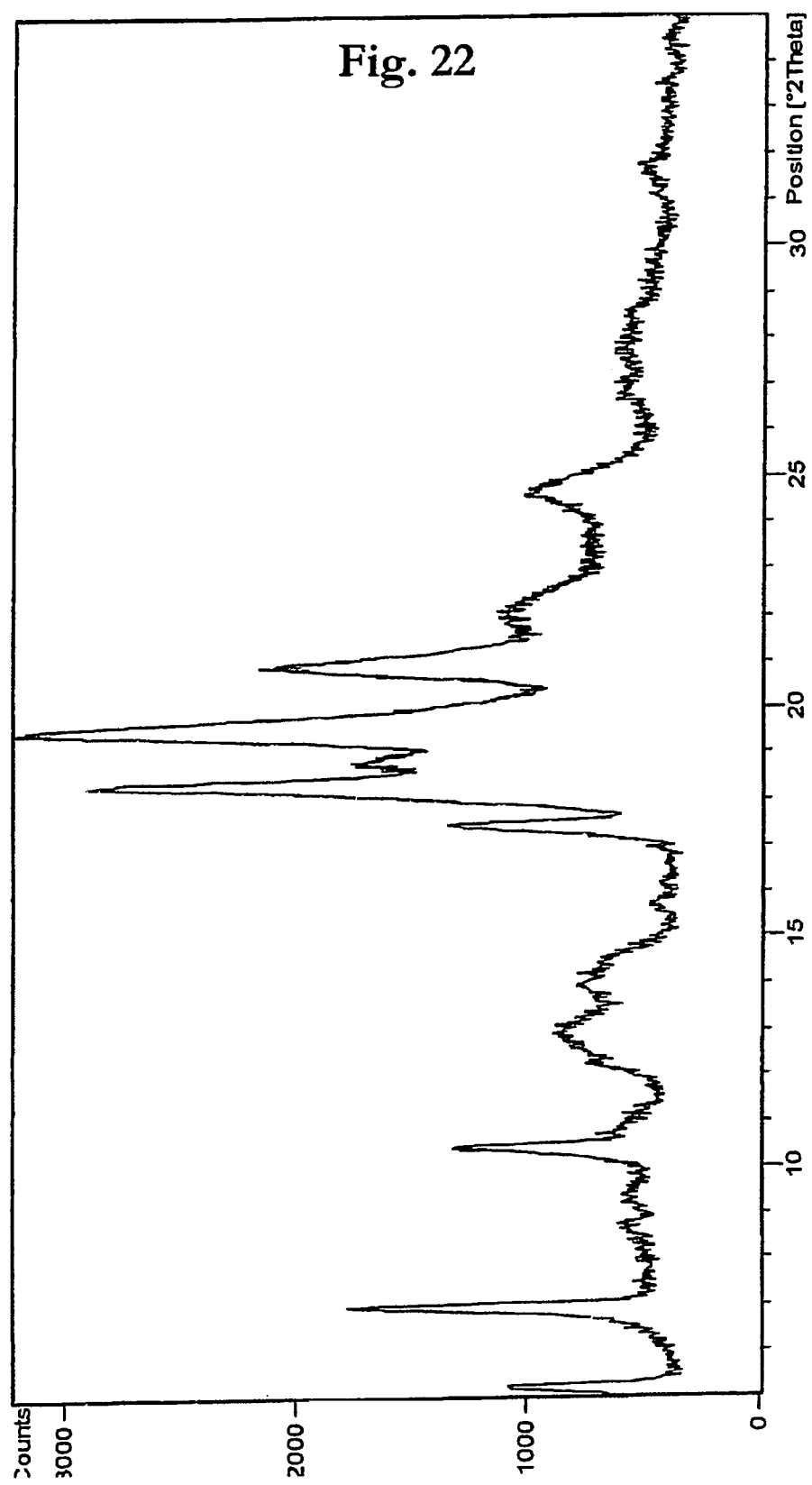
FIG. 22 shows a characteristic x-ray powder diffraction pattern of bimatoprost, according to embodiments of the present invention. Vertical axis: intensity (counts per second); Horizontal axis: 2θ (degrees).
Figure 23:
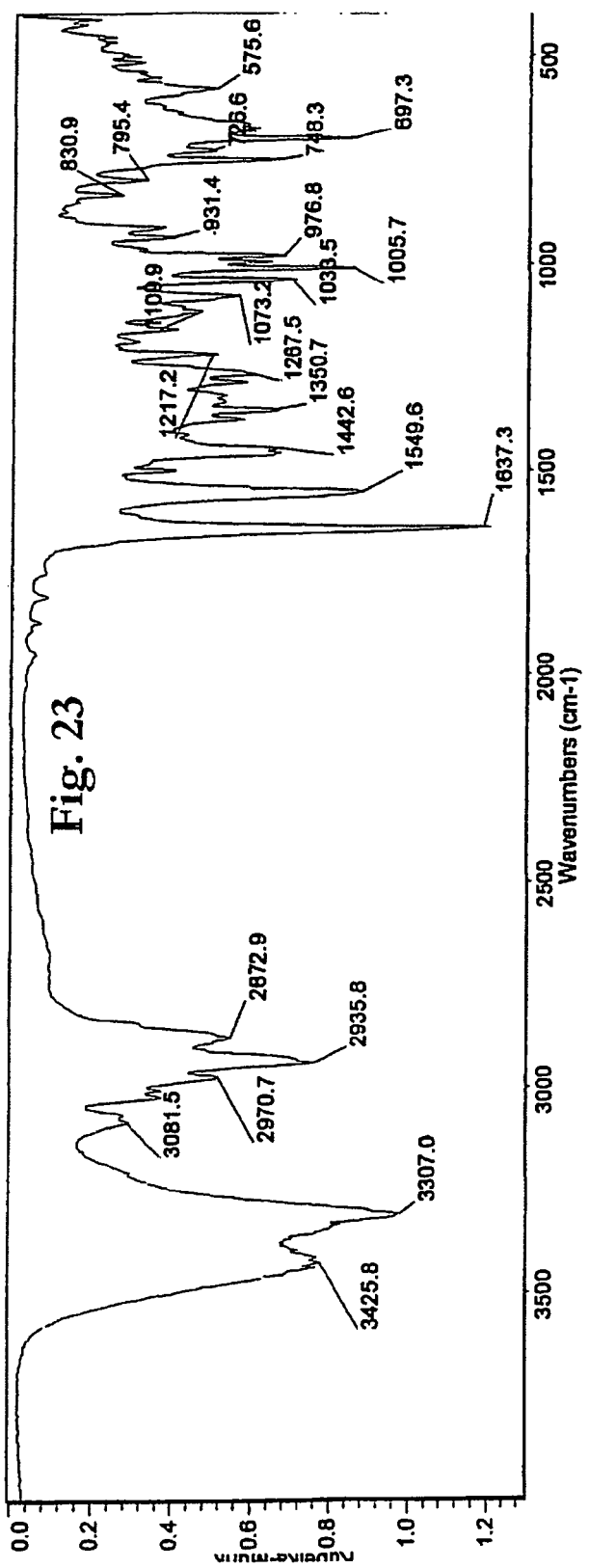
FIG. 23 shows the infrared spectrum (diffuse reflectance, DRIFTS) of bimatoprost in potassium bromide, according to embodiments of the invention.
Figure 24:
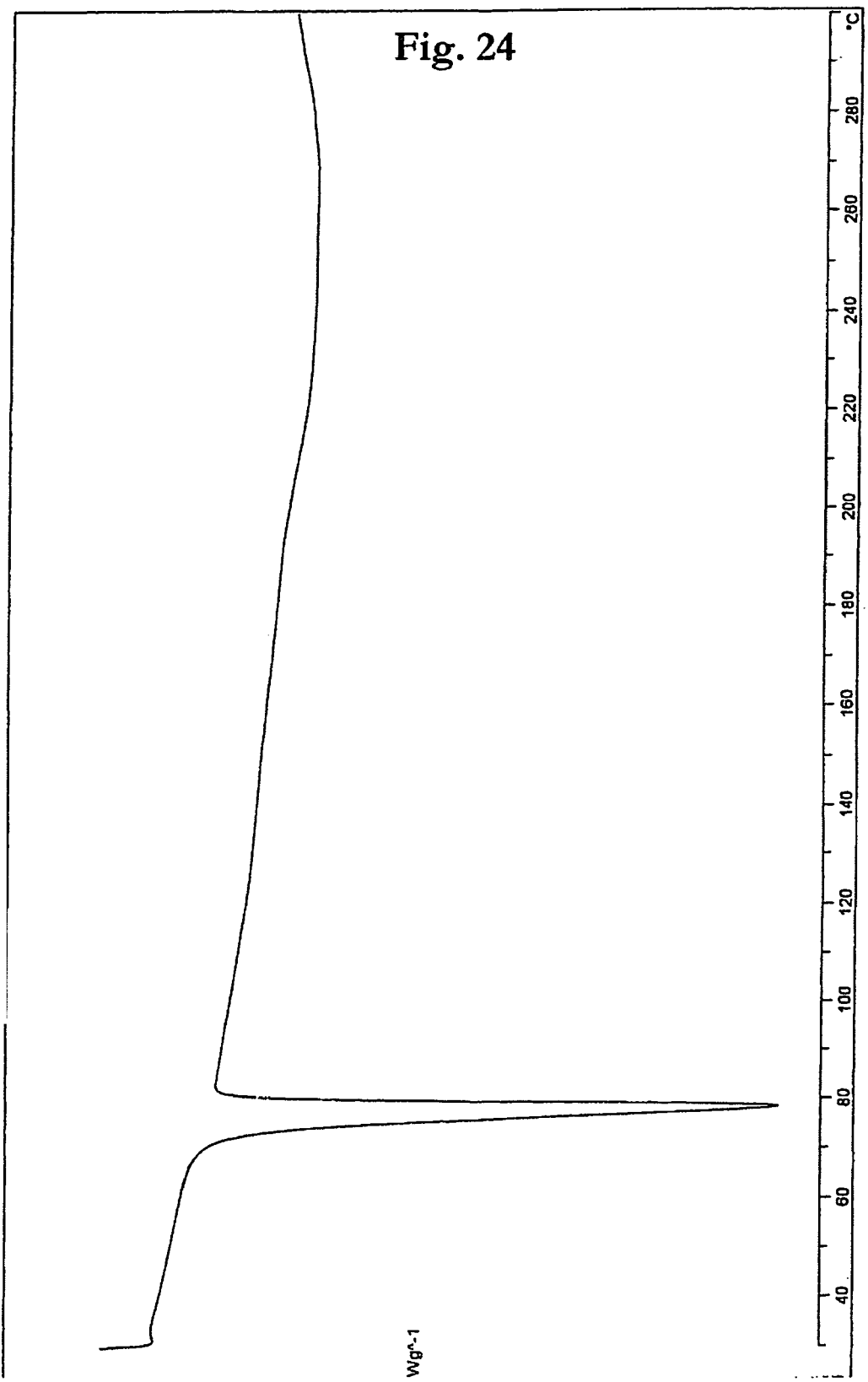
FIG. 24 shows the differential scanning calorimetry (DSC) curve of bimatoprost, according to embodiments of the invention.
Figure 25:
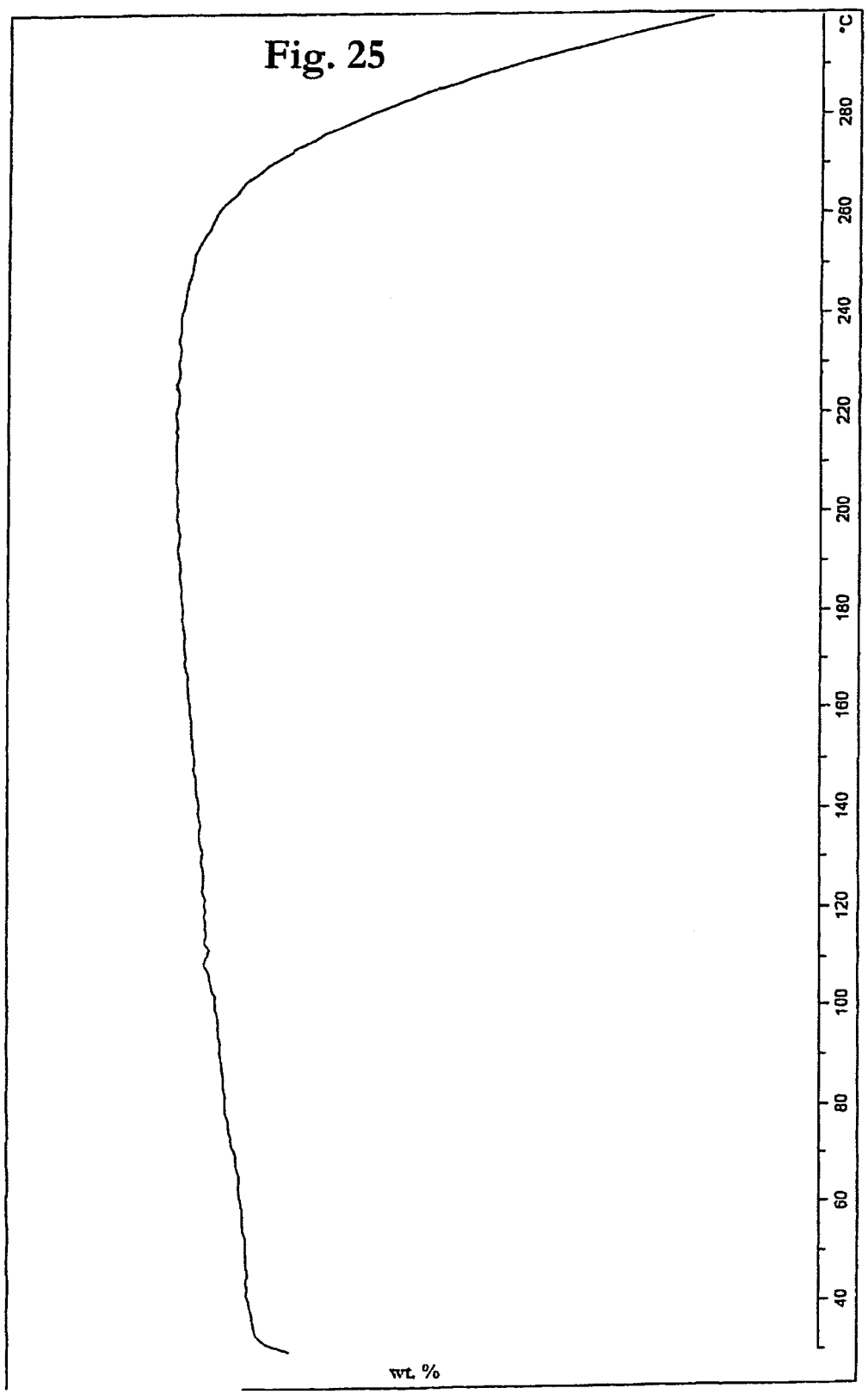
FIG. 25 shows the thermograviometric (TGA) curve of bimatoprost, according to embodiments of the invention.

(3aR,4R,5R,6aS)-4-[3R-(t-Butyldimethylsiloxy)-5-phenylpentyl]-5-hydroxy-hexahydro-2H-cyclopenta[b]furan-2-ol was characterized by IR DRIFTS (KBr) spectroscopy and DSC as set forth above and in FIGS. 15 and 16.

Example 20

(3aR,4R,5R,6aS)-4-[3S-(t-Butyldimethylsiloxy)-5-phenyl-1E-pentenyl]-5-hydroxy-hexahydro-2H-cyclopenta[b]furan-2-ol

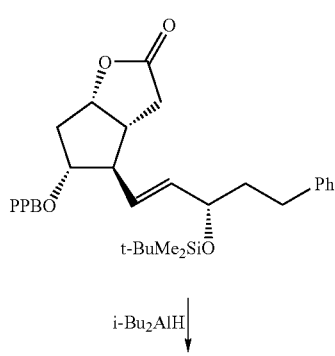

-continued

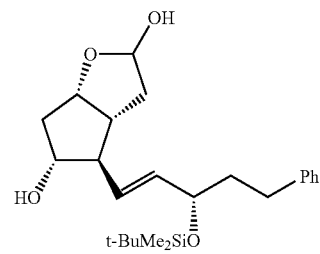

i-Bu$_2$AlH (20% solution in toluene, 54 mL, 66.0 mmol) was added dropwise during 1 h to a stirred solution of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one MTBE solvate (11.9 g, 20.7 mol) in toluene (120 mL) at −20 to −25° C. The mixture was stirred for 1 h at the same temperature, treated with MeOH (15 mL) and stirred for 1 h at rt. The precipitate was filtered off and washed on the filter with MeOH (100 mL). The combined filtrate was concentrated in vacuo. The residue was separated by column chromatography on silica gel. 4-PhC$_6$H$_4$CH$_2$OH was eluted with CH$_2$Cl$_2$. Oily (3aR,4R, 5R,6aS)-4-[3S-(t-butyldimethylsiloxy)-5-phenyl-1E-pentenyl]-5-hydroxy-hexahydro-2H-cyclopenta[b]furan-2-ol was eluted with 25:1 mixture CH$_2$Cl$_2$/MeOH and crystallized from hexane (60 mL) to give 5.8 g (79%) of (3aR,4R,5R, 6aS)-4-[3S-(t-butyldimethylsiloxy)-5-phenyl-1E-pentenyl]-5-hydroxy-hexahydro-2H-cyclopenta[b]furan-2-ol with 98% purity by HPLC: mp 91–94° C. $^1$H NMR (CDCl$_3$): 7.15 (m, 5H), 5.51 (m, 3H), 4.62 (m, 1H), 4.08 (m, 1H), 3.88 (m, 1H), 2.18 (m, 10H), 0.87 (s, 9H), 0.01 (d, J=3 Hz, 6H).

The x-ray powder diffraction pattern of crystalline (3aR, 4R,5R,6aS)-4-[3S-(t-butyldimethylsiloxy)-5-phenyl-1E-pentenyl]-5-hydroxy-hexahydro-2H-cyclopenta[b]furan-2-ol has characteristic peaks expressed in degrees 2θ at approximately 6.2, 8.8, 11.6, 13.2, 14.0, 15.3, 15.7, 16.5, 16.8, 17.2, 17.7, 20.3, 20.7, 21.4 and 22.2.

IR DRIFTS (KBr): 3322, 2928, 2854, 1603, 1496, 1471, 1452, 1437, 1359, 1256, 1096, 1069, 991, 972, 938, 835, 776, 746, and 697 cm$^{-1}$.

(3aR,4R,5R,6aS)-4-[3S-(t-Butyldimethylsiloxy)-5-phenyl-1E-pentenyl]-5-hydroxy-hexahydro-2H-cyclopenta[b]furan-2-ol was characterized by $^1$H NMR (CDCl$_3$), powder x-ray diffractometry, IR DRIFTS (KBr) spectroscopy, DSC and TGA as set forth above and in FIGS. 17, 18, 19, 20 and 21.

Example 21

(9S,11R,15R)-15-(t-Butyldimethylsiloxy)-9,11-dihydroxy-16-[3-(trifluoromethyl)phenoxy]-17,18,19,20-tetranor-5Z,13E-prostadienoic acid

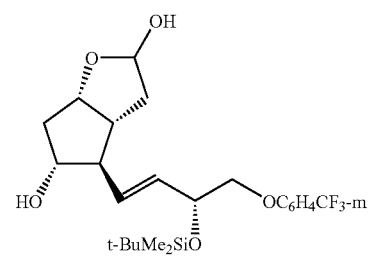

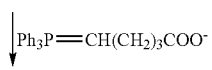

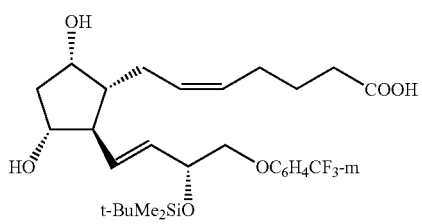

t-BuOK (16.8 g, 150.0 mmol) was added in several portions to a stirred mixture of HOOC(CH$_2$)$_4$PPh$_3$$^+$ Br$^-$ (33.2 g, 75.0 mmol) and THF (120 mL) at 0 to 5° C. The mixture was stirred for 1 h at rt. A solution of (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol (7.3 g, 15.0 mmol) in THF (50 mL) was added dropwise over 1 h to the stirred mixture at −25° C. The mixture was stirred at the same temperature for 6 h, heated to rt and poured into ice water (200 g). The mixture was washed with MTBE (4×100 mL). The aqueous layer was adjusted to pH 4–5 with 10% aq. citric acid. The precipitate was filtered off and washed on the filter with MTBE (200 mL). The organic filtrate was washed with water (200 mL), dried over Na$_2$SO$_4$, filtered and concentrated in vacuo. The residue (10.5 g) was purified by column chromatography on silica gel (100 g, eluent EtOAc) to give 7.3 g (85%) of (9S,11R,15R)-15-(t-butyldimethylsiloxy)-9,11-dihydroxy-16-[3-(trifluoromethyl)phenoxy]-17,18,19,20-tetranor-5Z,13E-prostadienoic acid as light yellow oil: 98.5% purity by HPLC (contained 3.0% of 5E-isomer); m/z 571.3 (M—H$^+$); $^1$H NMR (CDCl$_3$) δ 7.35 (t, J=8.0 Hz, 1H), 7.16 (d, J=8.0 Hz, 1H), 7.07 (s, 1H), 7.03 (d, J=8.0 Hz, 1H), 5.62 (m, 2H), 5.35 (m, 2H), 4.50 (m, 1H), 4.20–3.86 (m, 7H), 2.20 (m, 9H), 1.62 (m, 4H), 0.88 (s, 9H), 0.74 (s, 6H). (9S,11R,15R)-15-(t-Butyldimethylsiloxy)-9,11-dihydroxy-16-[3-(trifluoromethyl)phenoxy]-17,18,19,20-tetranor-5Z,13E-prostadienoic acid was characterized by $^1$H NMR spectroscopy as set forth above and in FIG. 6.

Example 22

(9S,11R, 15R)-15-(t-Butyldimethylsiloxy)-9,11-dihydroxy-17-phenyl-18,19,20-trinor-5Z-prostenoic acid

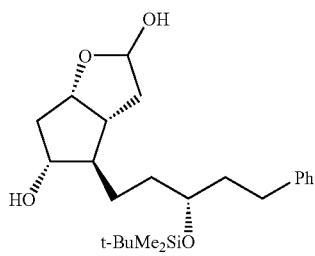

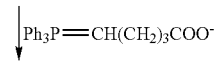

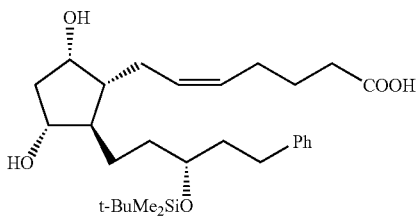

t-BuOK (8.4 g, 75.0 mmol) was added in several portions to a stirred mixture of HOOC(CH$_2$)$_4$PPh$_3$$^+$ Br$^-$ (16.6 g, 37.5 mmol) and THF (80 mL) at 0 to 5° C. The mixture was stirred for 1 h at rt. A solution of (3aR,4R,5R,6aS)-4-[3R-(t-butyldimethylsiloxy)-5-phenylpentyl]-5-hydroxy-hexahydro-2H-cyclopenta[b]furan-2-ol (3.15 g, 7.5 mmol) in THF (30 mL) was added dropwise over 1 h to the mixture at −25° C. The obtained mixture was stirred overnight at the same temperature, heated to rt and poured into ice water (100 g). The mixture was washed with MTBE (4×100 mL). The aqueous layer was adjusted to pH 4–5 with 10% aq. citric acid. The precipitate was filtered off and washed on the filter with MTBE (200 mL). The organic filtrate was washed with water (8×50 mL), dried over Na$_2$SO$_4$, filtered and concentrated in vacuo. The residue was purified on silica gel (110 g, eluent CH$_2$Cl$_2$, than a mixture CH$_2$Cl$_2$/MeOH 25:1) to give 3.35 g (89%) of (9S,11R,15R)-15-(t-butyldimethylsiloxy)-9,11-dihydroxy-17-phenyl-18,19,20-trinor-5Z-prostenoic acid as light yellow oil with 91% purity by HPLC: $^1$H NMR (CDCl$_3$) δ 7.23 (m, 5H), 5.34 (m, 3H), 4.14 (m, 1H), 3.89 (m, 1H), 3.70 (m, 1H), 2.58 (m, 2H), 1.83 (m, 15H), 0.87 (s, 9H), 0.02 (d, J=3 Hz, 6H).

Example 23

(9S, 11R, 15S)-15-(t-Butyldimethylsiloxy)-9,11-dihydroxy-17-phenyl-18,19,20-trinor-5Z,13E-prostadienoic acid

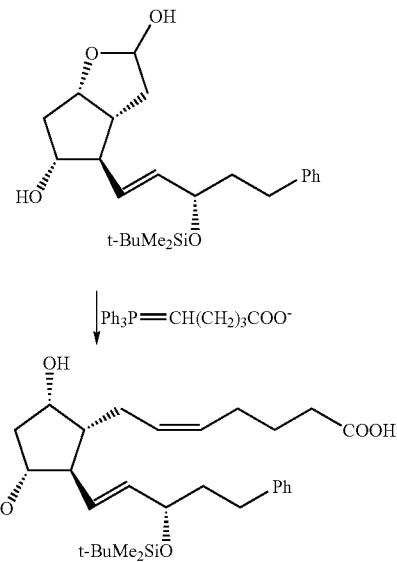

t-BuOK (10.8 g, 96.0 mmol) was added in several portions to a stirred mixture of HOOC(CH$_2$)$_4$PPh$_3^+$ Br$^-$ (21.3 g, 48.0 mmol) and THF (80 mL) at 0 to 5° C. The mixture was stirred for 1 h at rt. A solution of (3aR,4R,5R,6aS)-4-[3S-(t-butyldimethylsiloxy)-5-phenyl-1E-pentenyl]-5-hydroxy-hexahydro-2H-cyclopenta[b]furan-2-ol (5.0 g, 12.0 mmol) in THF (30 mL) was added dropwise over 1 h to the stirred mixture at −25° C. The mixture was stirred at the same temperature overnight, heated to rt and poured into ice water (100 g). The mixture was washed with MTBE (4×100 mL). The aqueous layer was adjusted to pH 4–5 with 10% aq. citric acid. The precipitate was filtered off and washed on the filter with MTBE (200 mL). The organic filtrate was washed with water (8×50 mL), dried over Na$_2$SO$_4$, filtered and concentrated in vacuo. The residue was purified by column chromatography on silica gel (CH$_2$Cl$_2$/MeOH 100:0 to 100:4) to give 5.2 g (87%) of (9S,11R,15S)-15-(t-butyldimethylsiloxy)-9,11-dihydroxy-17-phenyl-18,19,20-trinor-5Z,13E-prostadienoic acid as light yellow oil. $^1$H NMR spectra complain with the structure.

Example 24

(9S,11R,15R)-9,11,15-trihydroxy-16-[3-(trifluoromethyl)phenoxy]-17,18,19,20-tetranor-5Z,13E-prostadienoic acid

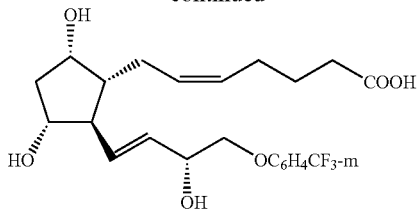

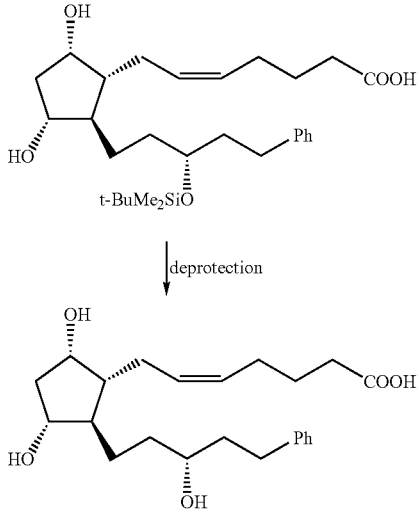

2 N HCl (10 mL) was added dropwise to the stirred solution of (9S,11R,15R)-15-(t-butyldimethylsiloxy)-9,11-dihydroxy-16-[3-(trifluoromethyl)phenoxy]-17,18,19,20-tetranor-5Z,13E-prostadienoic acid (2.01 g, 3.5 mmol) in IPA (30 mL) at rt. The mixture was stirred for 3 h at rt and treated with 7% NaHCO$_3$ (100 mL). The obtained mixture was washed with MTBE (3×20 mL), adjusted to pH 4–5 with 10% aq. citric acid and extracted with MTBE (3×20 mL). The combined organic extract was washed with brine, dried over Na$_2$SO$_4$ and concentrated in vacuo. The residue was purified by column chromatography on silica gel (eluting with CH$_2$Cl$_2$/MeOH 25:1) to give 1.26 g (78%) of (9S,11R,15R)-9,11,15-trihydroxy-16-[3-(trifluoromethyl)phenoxy]-17,18,19,20-tetranor-5Z,13E-prostadienoic acid as light yellow oil with 96% (+3.1% of 5E-isomer) purity by HPLC: m/z 457.1 (M—H$^+$). $^1$H NMR spectra complain with the structure.

Example 25

(9S,11R,15R)-9,11,15-trihydroxy-17-phenyl-18,19,20-trinor-5Z-prostenoic acid

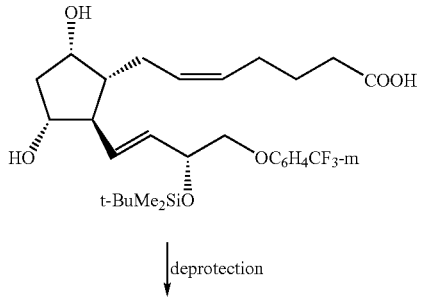

2 N HCl (5 mL) was added dropwise to a stirred solution of (9S,11R,15R)-15-(t-butyldimethylsiloxy)-9,11-dihydroxy-17-phenyl-18,19,20-trinor-5Z-prostenoic acid (2.52 g, 5.0 mmol) in MeOH (6 mL) at rt. The mixture was stirred for 3 h at rt and treated with 10% NaOH (10 mL). The mixture was stirred for 2 h, treated with water (30 mL) and washed with MTBE (3×30 mL). The aqueous layer was separated, adjusted to pH 3–4 with 10% aq. citric acid and extracted with MTBE (3×30 mL). The combined organic extracts was dried over Na$_2$SO$_4$, filtered and concentrated in vacuo. The residue was purified by column chromatography on silica gel (CH$_2$Cl$_2$/MeOH 100:0 to 100:4) to give 1.46 g (75%) of (9S,11R,15R)-9,11,15-trihydroxy-17-phenyl-18,19,20-trinor-5Z-prostenoic acid as light oil with 98.4% (+1.3% of 5Z-isomers) purity by HPLC. $^1$H NMR spectra complain with the structure.

Example 26

(9S,11R,15S)-9,11,15-Trihydroxy-17-phenyl-18,19,20-trinor-5Z,13E-prostadienoic acid

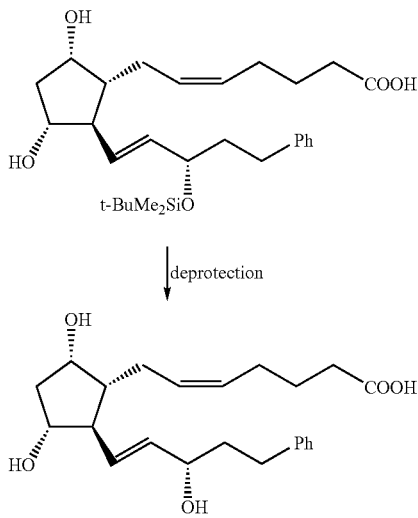

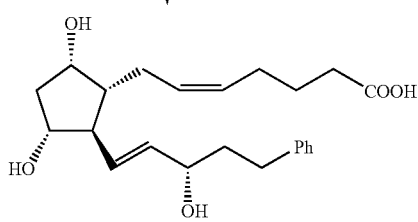

2 N HCl (9 mL) was added dropwise to a stirred solution of (9S,11R,15S)-15-(t-butyldimethylsiloxy)-9,11-dihydroxy-17-phenyl-18,19,20-trinor-5Z,13E-prostadienoic acid (3.8 g, 7.5 mmol) in MeOH (10 mL) at rt. The mixture was stirred for 3 h at the same temperature and treated with 10% NaOH (20 mL). The obtained mixture was stirred for 2 h at rt, treated with water (50 mL) and washed with MTBE (3×30 mL). The aqueous layer was adjusted to pH 3–4 with 10% aq. citric acid and extracted with MTBE (3×30 mL). The combined organic extract was dried over Na$_2$SO$_4$, filtered and concentrated in vacuo. The residue was purified by column chromatography on silica gel (eluting with CH$_2$Cl$_2$, then CH$_2$Cl$_2$/MeOH 25:1) to give 1.6 g (56%) of (9S,11R,15S)-9,11,15-trihydroxy-17-phenyl-18,19,20-trinor-5Z,13E-prostadienoic acid as light oil with 97% (+2.7% of 5E-isomer) purity by HPLC. $^1$H NMR (CDCl$_3$) δ: 7.12–7.27 (m, 5H); 5.33–5.63 (m, 7H); 4.00–4.20 (m, 2H); 3.80–4.00 (m, 1H); 2.50–2.70 (m, 2H); 1.56–2.30 (m, 14H). $^{13}$C NMR (CDCl$_3$) δ: 24.5; 25.3; 26.3; 31.8; 33.0; 38.5; 42.8; 50.1; 55.2; 72.3; 72.5; 77.6; 125.8; 128.4; 129.2; 129.6; 133.1; 134.8; 141.9; 177.4.

Example 27

Travoprost

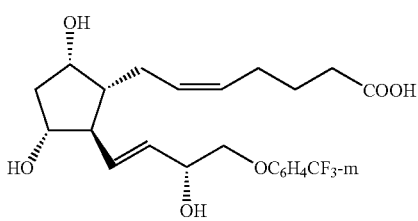

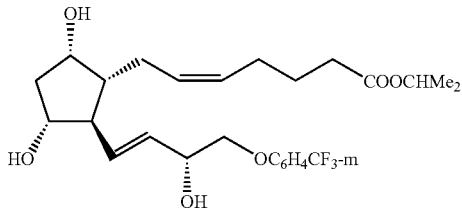

A mixture of (9S,11R,15R)-9,11,15-trihydroxy-16-[3-(trifluoromethyl)phenoxy]-17,18,19,20-tetranor-5Z,13E-prostadienoic acid (1.15 g, 2.5 mmol), Cs$_2$CO$_3$ (1.30 g, 4.0 mmol) and DMF (8 mL) was stirred at rt for 0.5 h. i-PrI (0.85 g, 5.0 mmol) was added dropwise to the stirred mixture. The mixture was stirred overnight at rt, treated with 3% aq. citric acid (40 mL) and extracted with MTBE (3×15 mL). The combined organic extracts were washed with brine, dried over Na$_2$SO$_4$ and concentrated in vacuo. The crude product was purified by column chromatography on silica gel (CH$_2$Cl$_2$/IPA 25:1). The relevant fractions were combined and concentrated in vacuo. The residue was further purified by preparative LC on Phenomenex™ Luna CN silica gel column (heptane/IPA 94–96%: 6–4%) to give travoprost as colorless oil with 99.9% purity by HPLC: [α]$_D^{20}$ +15.0° (c 1.0, CH$_2$Cl$_2$); m/z 523.3 (M+Na$^+$); $^1$H NMR (CDCl$_3$) δ: 7.35 (t, J=8 Hz, 1H), 7.16 (d, J=8 Hz, 1H), 7.11 (s, 1H), 7.05 (d, J=8 Hz, 1H), 5.66 (m, 2H), 5.36 (m, 2H), 4.94 (m, 1H), 4.49 (m, 1H), 4.13 (m, 1H), 3.96 (m, 3H), 3.00 (br s, 3H), 2.34 (m, 1H), 2.17 (m, 4H), 2.04 (m, 3H), 1.72 (m, 1H), 1.63 (m, 2H), 1.49 (m, 1H), 1.15 (d, J=6 Hz, 6H).

5E-Isomer of travoprost was isolated as minor fraction in the chromatography. MS and $^1$H NMR spectra of tie compound agree with proposed structure.

Example 28

Latanoprost

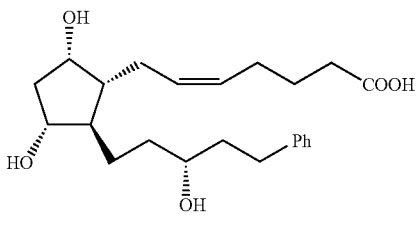

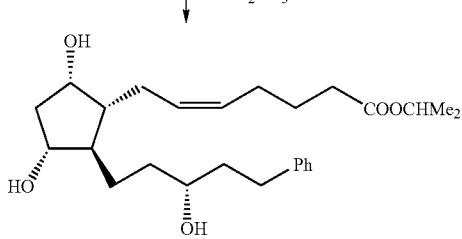

A mixture of (9S,11R,15R)-9,11,15-trihydroxy-17-phenyl-18,19,20-trinor-5Z-prostenoic acid (72.5 g, 0.19 mol), Me$_2$CHI (64.8 g; 0.38 mmol), Cs$_2$CO$_3$ (92.8 g, 0.28 mmol) and DMF (1.1 L) was stirred for 14 h at 25–30° C. (TLC monitoring) and poured into a stirred mixture of 3% aq.

citric acid (760 g) at 0–5° C. The mixture was extracted with MTBE. The combined organic layer was washed with 8% aq. NaHCO₃, dried over Na₂SO₄, filtered and concentrated in vacuo to give 73.2 g (89%) of crude latanoprost containing about 3% of 5E-isomer. The crude product was purified by column chromatography on silica gel (heptane/IPA 97:3 then 80:20). The relevant fractions were combined and concentrated in vacuo. The residue was further purified by preparative LC on Phenomenex™ Luna CN silica gel column (heptane/IPA 97:3) to give 50.4 g (62%) of latanoprost as colorless oil with 99.9% purity by HPLC: $[\alpha]_D^{20}$ +35° (c 1, MeCN).

5E-Isomer of latanoprost was isolated as minor fraction in the chromatography. MS and $^1$H NMR spectra of the compound agree with proposed structure.

Example 29

Methyl (9S,11R,15S)-9,11,15-trihydroxy-17-phenyl-18,19,20-trinor-5Z,13E-prostadienoate

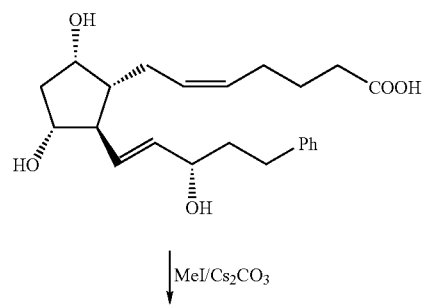

A mixture of (9S,11R,15S)-9,11,15-trihydroxy-17-phenyl-18,19,20-trinor-5Z,13E-prostadienoic acid (2.7 g, 6.9 mmol), MeI (1.48 g, 10.4 mmol), Cs₂CO₃ (3.4 g, 10.4 mmol) and DMF (25 mL) was stirred for 3 h at 0–10° C. (TLC monitoring) and poured into a stirred mixture of 2 M aq. NaHSO₄ (5 mL, 1.0 mmol), ice (100 mL) and ether (50 mL). The organic layer was separated and the aqueous one was extracted with ether (4×100 mL). The combined organic layers were washed with 1 M aq. Na₂S₂O₃ and brine (3×50 mL), dried over Na₂SO₄, filtered and evaporated under reduced pressure to give 2.7 g (96%) of crude product. The crude product was purified by column chromatography on silica gel (hexane/ethyl acetate 1:2 v/v) to give 2.6 g (93%) of methyl (9S,11R,15S)-9,11,15-trihydroxy-17-phenyl-18,19,20-trinor-5Z,13E-prostadienoate. $^1$H NMR (CDCl₃) δ: 7.10–7.25 (m, 5H); 5.33–5.55 (m, 4H); 4.00–4.20 (m, 4H); 3.80–4.00 (m, 2H); 3.58 (s, 3H); 2.60–2.70 (m, 2H); 1.30–230 (m, 14H). $^{13}$C NMR (CDCl₃) δ: 24.6; 25.2; 26.4; 31.6; 33.2; 38.6; 42.7; 49.6; 51.3; 55.2; 71.9; 72.2; 77.2; 125.6; 128.1; 128.2; 129.0; 129.2; 133.3; 135.2; 141.8; 174.1.

Example 30

Bimatoprost

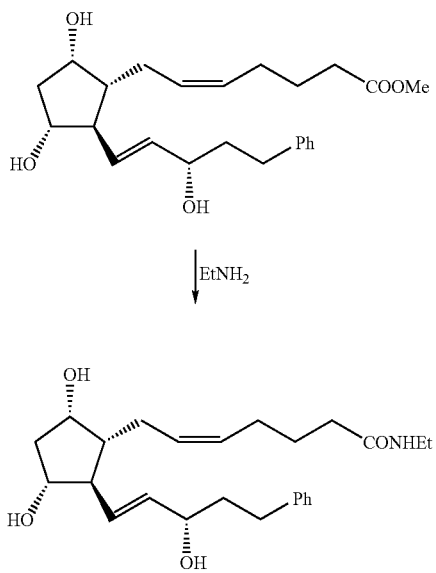

A mixture of methyl (9S,11R,15S)-9,11,15-trihydroxy-17-phenyl-18,19,20-trinor-5Z,13E-prostadienoate (2.5 g, 6.2 mmol) and 70% aq. EtNH₂ (100 mL) was stirred for 60 h at 20–25° C. (TLC monitoring). A solution was concentrated in vacuo to half of a volume, neutralized with 2 M aq. NaHSO₄ and extracted with EtOAc (5×100 mL). The combined organic layers were washed with brine (2×30 mL), dried over Na₂SO₄, filtered and concentrated in vacuo. The residue was treated with ether (20 mL), the precipitate was filtered off and dried under reduced pressure to give 2.1 g (82%) of bimatoprost as white solid. $^1$H NMR (CDCl₃) δ: 7.09–7.27 (m, 5H); 6.12 (t, J=5.5 Hz, 1H); 5.26–5.60 (m, 4H); 3.84–4.05 (m, 4H); 3.10–3.23 (m, 2H); 2.59–2.67 (m, 2H); 1.37–2.36 (m, 15H); 1.05 (t, J=7.3 Hz, 3H). $^{13}$C NMR (CDCl₃) δ: 14.6; 25.3; 25.5; 26.6; 31.7; 34.2; 35.7; 38.6; 42.8; 49.9; 55.2; 72.1; 77.3; 125.6; 128.2; 128.3; 129.1; 129.4; 133.1; 135.0; 141.9; 173.3.

The x-ray powder diffraction pattern of crystalline bimatoprost has characteristic peaks expressed in degrees 2θ at approximately 5.2, 6.9, 10.4, 17.4, 18.3, 18.8, 19.5 and 20.9. IR DRIFTS (KBr): 3426, 3307, 3082, 2971, 2936, 2873, 1637, 1550, 1494, 1452, 1443, 1373, 1351, 1286, 1268, 1217, 1153, 1110, 1073, 1034, 1006, 990, 977, 931, 909, 831, 795, 748, 727, 697 and 576 cm$^{-1}$.

Bimatoprost was characterized by powder x-ray diffractometry, IR DRIFTS (KBr) spectroscopy, DSC and TGA as set forth above and in FIGS. 22, 23, 24 and 25.

What is claimed:

1. A process for the preparation of alkyl 5Z-prostenoates of formula [1]

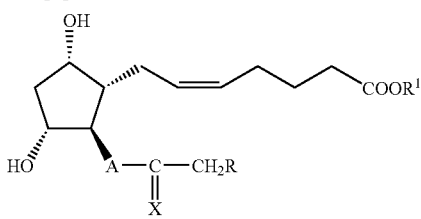

wherein R is 3-CF$_3$C$_6$H$_4$O—, 3-ClC$_6$H$_4$O—, PhO—, Bn—, Bu—, Me(CH$_2$)$_5$—; A is —CH$_2$CH$_2$— or —CH=CH—; X is X$^1$, O or (α-OH, H); X$^1$ is (α-OR$^3$, H), —OCH$_2$CH$_2$O—; (F, F); R$^1$ is C$_1$–C$_{10}$ alkyl group; R$^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down; such process comprising:

(a) contacting Corey aldehyde of formula [7]

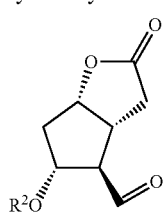

wherein R$^2$ is arylcarbonyl group, with a β-ketophosphonate of formula [8]

wherein R$^4$ is C$_1$–C$_4$ alkyl, Ph or Bn and where R is as defined above, in the presence of an aqueous alkali;

(b) converting the compound of formula [6]

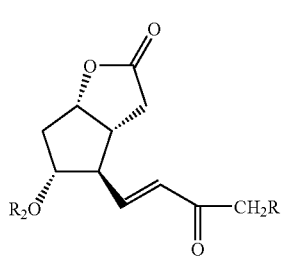

prepared at the step (a), to compound of formula [5]

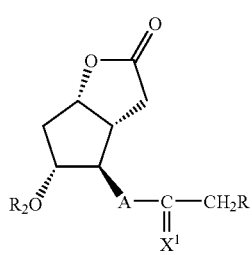

wherein X$^1$ is (α-OR$^4$, H), —OCH$_2$CH$_2$O—, (F, F); A, R, R$^2$ and R$^4$ are as defined above;

(c) reducing the compound [5] with diisobutylaluminum hydride at a temperature range from −30 to 0° C. to give the compound [4]

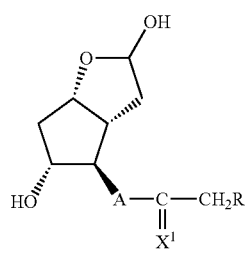

wherein A, R and X$^1$ are as defined above;

(d) reacting compound [4] with a metal salt of 5-(triphenylphosphoranylidene)pentanoic acid, to obtain the 5Z-prostenoic acid of formula [3]

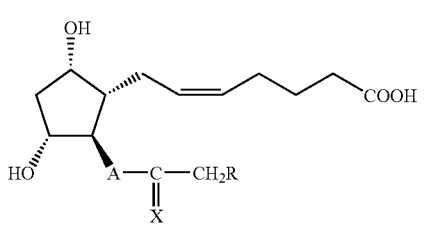

wherein A, R and X are as defined above;

(e) converting 5Z-prostenoic acid [3] to cesium 5Z-prostenoate of formula [2]

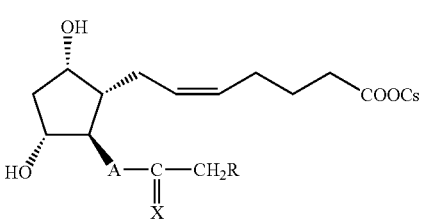

wherein A, R and X are as defined above; and (f) esterifying the cesium 5Z-prostenoate [2] with compound R$^1$Y wherein Y is a leaving group and R$^1$ is as defined above; to give the desired [1].

2. A process for the preparation of alkyl 5Z-prostenoate of formula [1]

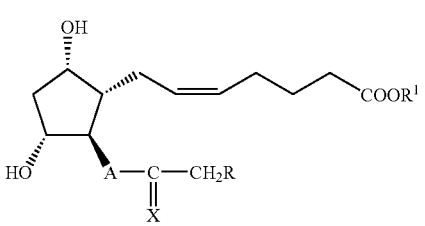

wherein R is 3-CF$_3$C$_6$H$_4$O—, 3-ClC$_6$H$_4$O—, PhO—, Bn—, Bu—, Me(CH$_2$)$_5$—; A is —CH$_2$CH$_2$— or —CH═CH—; X is X$^1$, O or (α-OH, H); X$^1$ is (α-OR$^3$, H), —OCH$_2$CH$_2$O— or (F, F); R$^1$ is C$_1$–C$_{10}$ alkyl group; R$^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down;

such process comprising esterifying the cesium 5Z-prostenoate [2]

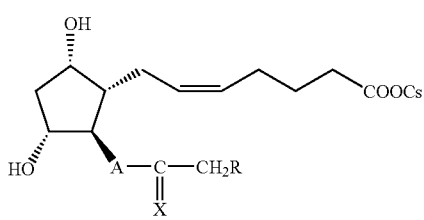

2 wherein A, R and X are as defined above, with compound R$^1$Y wherein Y is a leaving group and R$^1$ is as defined above; to give the desired alkyl 5Z-prostenoate [1].

3. A process for the preparation of lactol of formula [4]

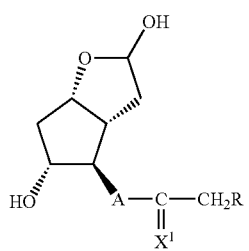

4

R is 3-CF$_3$C$_6$H$_4$O—, 3-ClC$_6$H$_4$O—, PhO—, Bn—, Bu—, Me(CH$_2$)$_5$—; A is —CH$_2$CH$_2$— or —CH═CH—;

X$^1$ is (α-OR$^3$, H), —OCH$_2$CH$_2$O— or (F, F); R$^3$ is selected from the group consisting of trialkylsilyl, dialkylarylsilyl, 1-alkoxyalkyl, unsubstituted and alkyl-substituted tetrahydro-2H-pyran-2-yl and tetrahydrofuran-2-yl group; α is down;

such process comprising reducing the compound [5]

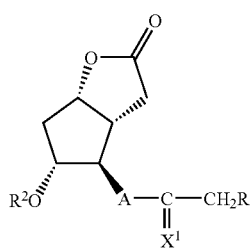

5 wherein X$^1$, A, R and R$^2$ are as defined above;

with diisobutylaluminum hydride at a temperature range from −30 to 0° C. to give the compound [4].

4. A process for the preparation of compound of formula [6]

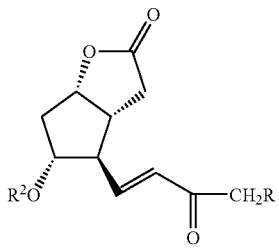

6 wherein R is 3-CF$_3$C$_6$H$_4$O—, 3-ClC$_6$H$_4$O—, PhO—, Bn—, Bu—, Me(CH$_2$)$_5$—; R$^2$ is arylcarbonyl group;

such process comprising contacting Corey aldehyde of formula [7]

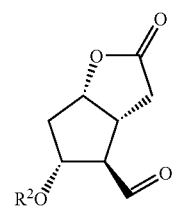

7 wherein R$^2$ is as defined above, with a β-ketophosphonate of formula [8]

RCH$_2$COCH$_2$PO(OR$^4$)$_2$   8 wherein R$^4$ is C$_1$–C$_4$ alkyl, Ph or Bn and where R is as defined above, in the presence of an aqueous alkali.

5. A process for the preparation of compound

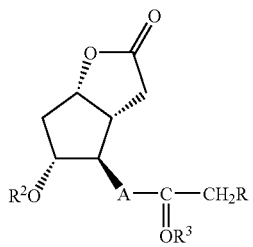

5

[X$^1$=(α-OR$^3$, H)]

wherein R is 3-CF$_3$C$_6$H$_4$O—, 3-ClC$_6$H$_4$O—, PhO—, Bn—, Bu—, Me(CH$_2$)$_5$—; A is —CH═CH— or —CH$_2$CH$_2$—; R$^2$ is arylcarbonyl group; R$^3$ is selected from the group consisting of trialkylsilyl, dialkylarylsilyl, 1-alkoxyalkyl, unsubstituted and alkyl-substituted tetrahydro-2H-pyran-2-yl or tetrahydrofuran-2-yl group;

such process comprising:
stereoselective reduction of the carbonyl group of the compound [6]

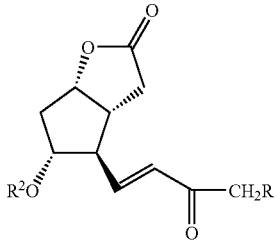

6 wherein R and R² are as defined above,
to yield a mixture of compounds of formulae [5-1] and [9-1]

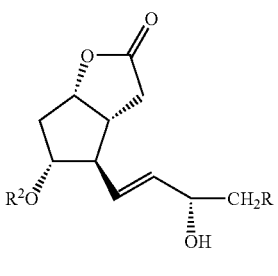

5-1

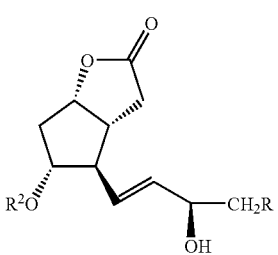

9-1 wherein R and R² are as defined above, and where [5-1] is the predominant isomer, which are subsequently converted into a mixture of compounds of formulae [5] [A=—CH=CH—; X¹=(α-OR³, H)]

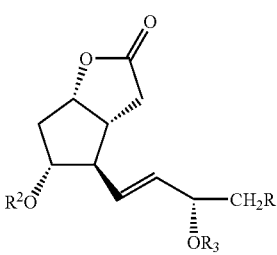

5

[A=—CH=CH—; X¹=(α-OR³, H)]
and [9-2]

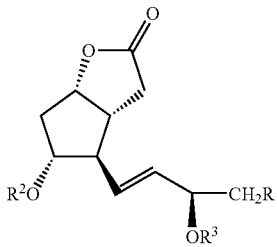

9-2 followed by isolation of the compound [5] [A=—CH=CH—; X¹=(α-OR³, H)] from the mixture and, if desired, hydrogenation of the compound [5] [A=—CH=CH—; X¹=(α-OR³, H)] in the presence of catalyst to give compound of formula [5] [A=—CH₂CH₂—; X¹=(α-OR³, H)]

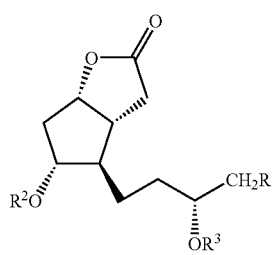

5

[A=—CH₂CH₂—; X¹=(α-OR³, H)]
wherein R, R² and R³ are as defined above.

6. A process according to claim 4 which process comprising the steps of converting compound [9-2] into compound [9-1], oxidizing the hydroxyl group of the compound [9-1] to yield the compound [6] and recycling the compound [6] to the beginning of the process.

7. A process according to any one of claims 1 and 2 wherein R¹ is methyl or isopropyl.

8. A process according to any one of claims 1 and 2 wherein Y is bromide or iodide.

9. A process according to any one of claims 1–5 wherein R² is benzoyl, p-toluoyl, p-chlorobenzoyl, p-bromobenzoyl or p-phenylbenzoyl (PPB).

10. A process according to any one of claims 1, 2, 4 and 5 wherein R³ is tetrahydro-2H-pyran-2-yl or t-butyldimethylsilyl group.

11. A process according to claim 5 wherein said stereoselective reduction of the carbonyl group of the compound [6] is carried out by (−)-B-chlorodiisopinocampheylborane.

12. A process according to claim 5, which further comprises purifying the compound of formula 5 [X=(α-OR³, H)] by re-crystallization.

13. A process for the preparation of compound of formula [5] [A=—CH₂CH₂—; X=(α-OR³, H)]

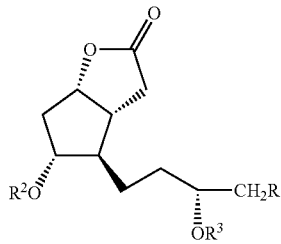

[A=—CH₂CH₂—; X=(α-OR³, H)]

wherein R is 3-CF₃C₆H₄O—, 3-ClC₆H₄O—, PhO—, Bn—, Bu—, Me(CH₂)₅—; R² is arylcarbonyl group; R³ is selected from the group consisting of trialkylsilyl, dialkylarylsilyl, 1-alkoxyalkyl, unsubstituted and alkyl-substituted tetrahydro-2H-pyran-2-yl or tetrahydrofuran-2-yl group;

which process comprising catalytic hydrogenation of compound of formula [5] [A=—CH=CH—; X=(α-OR³, H)]

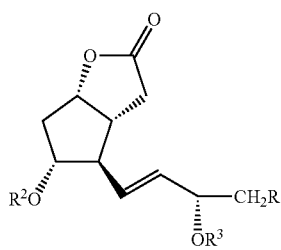

[A=—CH=CH—; X=(α-OR³, H)]

14. A process according to claim 13 wherein said catalyst comprises palladium, platinum or nickel.

15. A process according to claim 13 wherein said catalyst is palladium on carbon.

16. (3aR,4R,5R,6aS)-4-[3S-(t-Butyldimethylsiloxy)-5-phenyl-1E-pentenyl]-5-(4-phenylbenzoyloxy)-hexahydro-2H-cyclopenta[b]furan-2-one of the formula

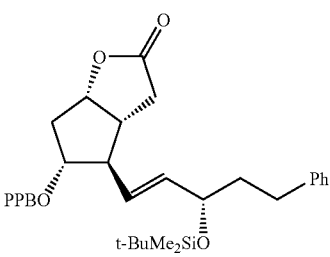

17. Crystalline MTBE solvate of (3aR,4R,5R,6aS)-4-[3S-(t-butyldimethylsiloxy)-5-phenyl-1E-pentenyl]-5-(4-phenylbenzoyloxy)-hexahydro-2H-cyclopenta[b]furan-2-one.

18. Crystalline (3aR,4R,5R,6aS)-4-[3R-(t-butyldimethylsiloxy)-4-[3-(trifluoromethyl)phenoxy]-1E-butenyl]-5-(4-phenylbenzoyloxy)-hexahydro-2H-cyclopenta[b]furan-2-one of the formula

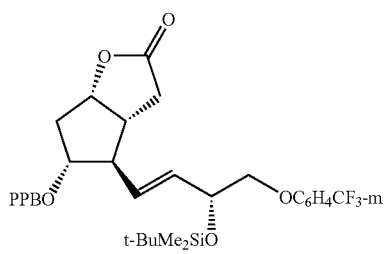

19. Crystalline (3aR,4R,5R,6aS)-4-[3R-(t-butyldimethylsiloxy)-4-[3-(trifluoromethyl)phenoxy]-1E-butenyl]-5-hydroxy-hexahydro-2H-cyclopenta[b]furan-2-ol of the formula

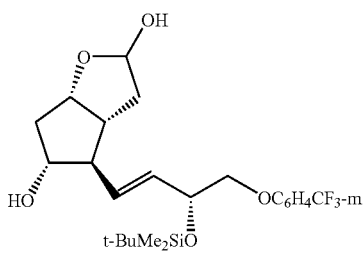

20. (3aR,4R,5R,6aS)-4-[3S-(t-Butyldimethylsiloxy)-5-phenyl-1E-pentenyl]-5-hydroxy-hexahydro-2H-cyclopenta[b]furan-2-ol of the formula

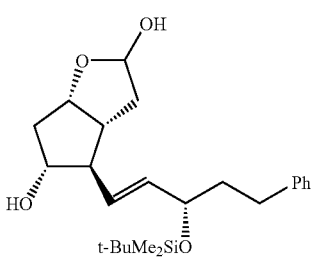

21. Crystalline (3aR,4R,5R,6aS)-4-[3S-(t-butyldimethylsiloxy)-5-phenyl-1E-pentenyl]-5-hydroxy-hexahydro-2H-cyclopenta[b]furan-2-ol.

22. Crystalline (3aR,4R,5R,6aS)-4-[3R-(t-butyldimethylsiloxy)-5-phenylpentyl]-5-hydroxy-hexahydro-2H-cyclopenta[b]furan-2-ol.

* * * * *

UNITED STATES PATENT AND TRADEMARK OFFICE
CERTIFICATE OF CORRECTION

PATENT NO. : 7,166,730 B2  Page 1 of 1
APPLICATION NO. : 11/125164
DATED : January 23, 2007
INVENTOR(S) : Arie Gutman et al.

It is certified that error appears in the above-identified patent and that said Letters Patent is hereby corrected as shown below:

In column 51, line 66 should read:

wherein $X^1$ is (á-OR$^3$, H), -OCH$_2$CH$_2$O-, (F, F); A, R,

In column 54, claim 5 the represented structure of the following formula should be:

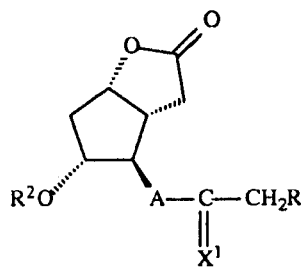

Signed and Sealed this

Ninth Day of February, 2010

David J. Kappos
*Director of the United States Patent and Trademark Office*